(12) United States Patent
Nguyen et al.

(10) Patent No.: US 11,723,955 B1
(45) Date of Patent: Aug. 15, 2023

(54) VEGFR FUSION PROTEIN PHARMACEUTICAL COMPOSITION

(71) Applicant: Allgenesis Biotherapeutics Inc., Taipei (TW)

(72) Inventors: Tan Nguyen, Fullerton, CA (US); Pei-Tzu Wu, Taipei (TW); Yung-Sheng Chang, Taipei (TW); Madhu Cherukury, Irvine, CA (US)

(73) Assignee: Allgenesis Biotherapeutics Inc., Taipei (TW)

( * ) Notice: Subject to any disclaimer, the term of this patent is extended or adjusted under 35 U.S.C. 154(b) by 0 days.

(21) Appl. No.: 17/663,260

(22) Filed: May 13, 2022

(51) Int. Cl.
| | |
|---|---|
| *C07K 14/705* | (2006.01) |
| *C07K 14/71* | (2006.01) |
| *C07K 19/00* | (2006.01) |
| *A61K 9/08* | (2006.01) |
| *A61K 38/17* | (2006.01) |
| *A61K 47/18* | (2017.01) |
| *A61K 47/26* | (2006.01) |
| *A61K 47/02* | (2006.01) |
| *A61K 47/10* | (2017.01) |
| *A61K 47/12* | (2006.01) |
| *A61K 9/00* | (2006.01) |

(52) U.S. Cl.
CPC .......... *A61K 38/179* (2013.01); *A61K 9/0019* (2013.01); *A61K 9/0048* (2013.01); *A61K 9/08* (2013.01); *A61K 47/02* (2013.01); *A61K 47/10* (2013.01); *A61K 47/12* (2013.01); *A61K 47/183* (2013.01); *A61K 47/26* (2013.01); *C07K 2319/30* (2013.01)

(58) Field of Classification Search
CPC ............ A61K 2300/00; A61K 39/3955; A61K 38/00; A61K 9/19; A61K 2039/545; A61K 38/17; A61K 38/1709; A61K 39/001135; A61K 39/395; A61K 39/001103; A61K 38/177; A61K 38/179; C07K 16/22; C07K 16/241; C07K 19/00; C07K 16/2863; C07K 14/71
See application file for complete search history.

(56) References Cited

U.S. PATENT DOCUMENTS

| | | | |
|---|---|---|---|
| 4,946,778 A | 8/1990 | Ladner et al. | |
| 5,094,941 A | 3/1992 | Hart | |
| 5,260,203 A | 11/1993 | Ladner et al. | |
| 5,874,542 A | 2/1999 | Rockwell et al. | |
| 6,160,099 A | 12/2000 | Jonak et al. | |
| 7,750,138 B2 | 7/2010 | Fang et al. | |
| 7,943,728 B2 | 5/2011 | Chuang et al. | |
| 8,323,634 B2 * | 12/2012 | Bock ...................... | A61P 43/00 530/413 |
| 8,350,010 B2 | 1/2013 | Chuntharapai et al. | |
| 9,044,436 B2 | 6/2015 | Chuang et al. | |
| 9,265,827 B2 | 2/2016 | Wiegand et al. | |
| 9,969,791 B2 | 5/2018 | Chuang et al. | |
| 9,988,611 B2 | 6/2018 | Her et al. | |
| 10,508,137 B2 | 12/2019 | Chuang | |
| 10,576,128 B2 * | 3/2020 | Sigi ...................... | A61K 9/0051 |
| 11,192,927 B2 * | 12/2021 | Wu ...................... | C07K 14/71 |
| 11,299,531 B2 * | 4/2022 | Zen ...................... | A61P 9/00 |
| 2003/0027751 A1 | 2/2003 | Kovesdi et al. | |
| 2003/0064053 A1 | 4/2003 | Liu et al. | |
| 2006/0040325 A1 | 2/2006 | Wu et al. | |
| 2006/0177443 A1 | 8/2006 | Fanslow, III et al. | |
| 2006/0234347 A1 | 10/2006 | Harding et al. | |
| 2008/0188413 A1 | 8/2008 | Chuang et al. | |
| 2008/0207502 A1 | 8/2008 | Rastelli et al. | |
| 2013/0303733 A1 | 11/2013 | Barbas | |
| 2014/0213769 A1 | 7/2014 | Hong et al. | |
| 2015/0079084 A1 | 3/2015 | Her et al. | |
| 2015/0266942 A1 | 9/2015 | Tian | |
| 2015/0266945 A1 | 9/2015 | Lai et al. | |
| 2017/0267731 A1 | 9/2017 | Chuang | |
| 2017/0369552 A1 * | 12/2017 | Zen ...................... | A61P 27/02 |
| 2018/0170979 A1 * | 6/2018 | Wu ...................... | A61P 9/10 |
| 2019/0016817 A1 * | 1/2019 | Taddei .................. | C07K 16/22 |
| 2019/0194271 A1 * | 6/2019 | Wu ...................... | A61P 9/10 |
| 2019/0343918 A1 * | 11/2019 | Graham .............. | A61K 9/0048 |
| 2020/0181121 A1 | 6/2020 | Mei et al. | |
| 2020/0181122 A1 | 6/2020 | Zhang et al. | |
| 2020/0181214 A1 * | 6/2020 | Wu ...................... | A61K 38/00 |

FOREIGN PATENT DOCUMENTS

| | | | |
|---|---|---|---|
| WO | 8801649 A1 | 3/1998 | |
| WO | 2007134876 A2 | 11/2007 | |
| WO | 2014160507 A1 | 10/2014 | |
| WO | 2015200905 A2 | 12/2015 | |
| WO | 2016029131 A1 | 2/2016 | |
| WO | 2017001990 A1 | 1/2017 | |
| WO | WO-2019099921 A2 * | 5/2019 | |

OTHER PUBLICATIONS

Bhattacharya et al. Impact of genetic variation on three dimensional structure and function of proteins. PLoS ONE 12(3): e0171355, 2017.*
Bork, P. Powers and pitfalls in sequence analysis: the 70% hurdle. Genome Res 10: 398-400, 2000.*
Bork, P. Go hunting in sequence databases but watch out for the traps. Trends in Genetics 12(10): 425-427, 1996.*
Brenner. S.E. Errors in genome annotation. Trends in Genetics 15:132-133, 1999.*
Doerks et al. Protein annotation: detective work for function prediction. Trends in Genetics 14:248-250, 1998.*
Fenton et al. Rheostat positions: a new classification of protein positions relevant to pharmacogenomics. Medicinal Chem Res 29: 1133-1146, 2020.*

(Continued)

*Primary Examiner* — Bridget E Bunner
(74) *Attorney, Agent, or Firm* — Ice Miller LLP

(57) ABSTRACT

The present invention relates to a biologic that inhibits angiogenesis. In particular, the present invention relates to fusion proteins that inhibit the integrin activated pathway and one other angiogenic factor-activated pathway as well as formulation compositions of such fusion proteins, as well as methods for producing and using the same.

7 Claims, 15 Drawing Sheets

Specification includes a Sequence Listing.

(56) References Cited

OTHER PUBLICATIONS

Giannos et al. Formulation stabilization and disaggregation of bevacizumab, ranibizumab and aflibercept in dilute solutions. Pharm Res 35: 78, 2018.*
Guo et al. Protein tolerance to random amino acid change. Proc Natl Acad Sci USA 101(25): 9205-9210, 2004.*
Holash et al. VEGF-Trap: a VEGF blocker with potent antitumor effects. Proc Natl Acad Sci USA 99(17): 11393-11398, 2002.*
Ngo et al. "Computational complexity, protein structure prediction, and the Levinthal paradox" in The Protein Folding Problem and Tertiary Structure Prediction, pp. 492-495, 1994.*
Skolnick et al. From genes to protein structure and function: novel applications of computational approaches in the genomic era. Trends Biotechnol 18(1):34-39 2000.*
Smith et al. The challenges of genome sequence annotation or "the devil is in the details". Nature Biotechnol 15: 1222-1223, 1997.*
Tokuriki et al. Stability effects of mutations and protein evolvability. Curr Opin Structural Biol 19: 596-604, 2009.*
Wang, W. Instability, stabilization, and formulation of liquid protein pharmaceuticals. Int J Pharmaceutics 185: 129-188, 1999.*
Wells, J.A. Additivity of mutational effects in proteins. Biochemistry 29(37): 8509-8517, 1990.*
Jain, Rakesh K.,"Molecular Regulation of Vessel Maturation," Nature Medicine; vol. 9, issue 6 (Jun. 2003) pp. 385-693.
Major, Terry C., et al., "Inhibition of Cell Growth: Effects of the Tyrosine Kinase Inhibitor CGP 53716," The Journal of Pharmacology and Experimental Therapeutics; vol. 283, issue 1, (1997) pp. 402-410.
Staunton, Donald E., et al., "Targeting Integrin Structure and Function in Disease," Advances in Immunology; vol. 91 (2006) pp. 111-157.
McLane, Mary Anne et al. "Viper Venom Disintegrins and Related Molecules," Proceedings of the Society for Experimental Biology and Medicine; vol. 219 (1998) pp. 109-119.
Niewiarowski, S. et al., "Disintegrins and Other Naturally Occurring Antagonists of Platelet Fibrinogen Receptors," Semin Hematol; vol. 31, issue 4 (Oct. 1994) Abstract Only.
Calvete, Juan J., "Structure-Function Correlations of Snake Venom Disintegrins," Current Pharmaceutical Design; vol. 11, issue 7 (2005) pp. 829-835.
Blobel, Carl P. et al., "Structure, Function and Evolutionary Relationship of Proteins Containing a Disintegrin Domain," Current Opinion in Cell Biology; vol. 4, issue 5 (1992) pp. 760-765.
Swenson, Stephen et al., "Anti-Angiogenesis and RGD-Containing Snake Venom Disintegrins," Current Pharmaceutical Design; vol. 13 (2007) pp. 2860-2871.
Folkman, Judah et al. "Angiogenic Factors," Science; vol. 235 (Jan. 23, 1987) pp. 442-447.
Carmeliet, Peter et al. "Molecular mechanisms and clinical applications of angiogenesis," Nature; vol. 473 (May 19, 2011) pp. 298-307.
Polverini, P.J. "The Pathophysiology of Angiogenesis," Critical Reviews in Oral Biology & Medicine; vol. 6, issue 3 (1995) pp. 230-247.
Perrotta, Paola et al. "Pharmacological strategies to inhibit intraplaque angiogenesis in atherosclerosis," Vascular Pharmacology; vol. 112 (2019) pp. 72-78.
Ebenezer, Daniel et al. "Risk of Scar in the Comparison of Age-related Macular Degeneration Treatments Trials," Ophthalmology; vol. 121, issue 3 (Mar. 2014) pp. 656-666.
Patsenker, E. et al. "Pharmacological Inhibition of Integrin Alphav Beta3 Aggravates Experimental Liver Fibrosis and Suppresses Hepatic Angiogenesis," Hepatology; vol. 50, issue 5 (Nov. 2009) pp. 1501-1511.
Xu, Junyan et al. "Vascular wall extracellular matrix proteins and vascular diseases," Biochimica et Biophysica Acta; vol. 1842, issue 11 (2014) pp. 2106-2119.

Sullivan, Laura A. et al. "The VEGF family in cancer and antibody-based strategies for their inhibition," MAbs; vol. 2, issue 2 (Mar./Apr. 2010) pp. 165-175.
Willet, Christopher G. et al. "Direct evidence that the VEGF-specific antibody bevacizumab has antivascular effects in human rectal cancer," Nature Medicine; vol. 10, issue 2 (Feb. 2004) pp. 145-147.
Papadopoulos, Nicholas et al. "Binding and neutralization of vascular endothelial growth factor (VEGF) and related ligands by VEGF Trap, ranibizumab and bevacizumab," Angiogenesis; vol. 15, issue 2(2012) pp. 171-185.
Aiello, Lloyd Paul et al. "Suppression of retinal neovascularization in vivo by inhibition of vascular endothelial growth factor (VEGF) using soluble VEGF-receptor chimeric proteins," The Proceedings of the National Academy of Sciences; vol. 92, issue 23 (Nov. 1995) pp. 10457-10461.
Somanath, Payaningal R. et al. "Integrin and Growth Factor Receptor Alliance in Angiogenesis," Cell Biochemistry and Biophysics; vol. 53, issue 2 (2009) pp. 53-64.
Eliceiri, Brian P. "Integrin and Growth Factor Receptor Crosstalk," Circulation Research; vol. 89, issue 12 (2001) pp. 1104-1110.
Avraamides, Christie J. et al. "Integrins in angiogenesis and lymphangiogenesis," Nature Reviews Cancer; vol. 8, issue 8 (Aug. 2008) pp. 604-617.
Desgrosellier, Jay S. et al. "Integrins in cancer: biological implications and therapeutic opportunities," Nature Reviews Cancer; vol. 10, issue 1 (Jan. 2010) pp. 9-22.
McLane, Mary Anne et al. "Disintegrins in health and disease," Frontiers in Bioscience; vol. 13 (May 1, 2008) pp. 6617-6637.
Scarborough, Robert M. et al. "Characterization of the Integrin Specificities of Disintegrins Isolated from American Pit Viper Venoms," The Journal of Biological Chemistry; vol. 268, issue 2 (Jan. 1993) pp. 1058-1065.
Rahman, Salman et al. "Modulation of RGD sequence motifs regulates disintegrin recognition of $\alpha11b\beta3$ and $\alpha5\beta1$ integrin complexes," Biochemical Journal; vol. 335, issue 2 (1998) pp. 247-257.
Cunningham, Brian C. et al. "High-Resolution Epitope Mapping of hGH-Receptor Interactions by Alanine-Scanning Mutagenesis," Science; vol. 244, issue 4908 (Jun. 1989) pp. 1081-1085.
Elshabrawy, Hatem A. et al. "The Pathogenic Role of Angiogenesis in Rheumatoid Arthritis," Angiogenesis; vol. 18, issue 4 (Oct. 2015) pp. 433-448.
Lee, Alice et al., "Abstract 2327: Anti-angiogenic activity of a CovX bi-functional antibody conjugate targeting both activin-receptor like kinase type 1 (ALK-1) and vascular endothelial growth factor (VEGF)." Cancer Research, vol. 72, supplement 8 (Apr. 2012) 2327.
Dorrell, Michael et al., "Combination angiostatic therapy completely inhibits ocular and tumor angiogenesis," Proceedings of the National Academy of Sciences; vol. 104, No. 3 (Jan. 16, 2007) pp. 967-972.
Yao-Tsung Chang abstract (Doctoral Thesis. Structure-activity relationships of the RGD loop, linker region, and C-terminus of Rhodostomin mutants in the recognition of integrins., Jan. 1, 2014) (Year: 2014) (13 pages).
Shiu, Jia-Hau et al. "Effect of P to A Mutation of the N-Terminal Residue Adjacent to the Rgd Motif on Rhodostomin: Importance of Dynamics in Integrin Recognition," PLoS ONE, vol. 7, issue 1 (2012) e28833.
Chen, Chiu-Yueh et al. "Effect of D To E mutation of the RGD motif in rhodostomin on its activity, structure, and dynamics: Importance of the interactions between the D residue and integrin." Proteins, vol. 76 (2009) pp. 808-821.
Kolvunen, Eridd et al., "Phage Libraries Displaying Cyclic Peptides with Different Ring Sizes: Ligand Specificities of the ROD-Directed Integrins," Bio/Technology, vol. 13 (Mar. 13, 1995) pp. 265-270.
Lu, Xinjie et al. "Preferential antagonism of the interactions of the integrin alpha lib beta 3 with immobilized glycoprotein ligands by snake-venom RGD (Arg-Gly-Asp) proteins," The Biochemical Journal, vol. 304 (Dec. 1994) pp. 929-936.
Kuntz, Irwin D. "Structure-Based Strategies for Drug Design and Discovery." Science, vol. 257 (Aug. 21, 1992) pp. 1078-1082.

(56) References Cited

OTHER PUBLICATIONS

Miller, David W. et al. "Ligand binding to proteins: The binding landscape model." Protein Science, vol. 6 (received date Mar. 18, 1997) pp. 2166-2179.

Koivunen, Erkki et al., "Identification of Receptor Ligands with Phage Display Peptide Libraries," Journal of Nuclear Medicine, vol. 40, issue 5 (May 1999) pp. 883-888.

Emerson, Vaughn M., et al. "Current and emerging therapies for the treatment of age-related macular degeneration,". Clinical Ophthalmology, vol. 2, issue 2 (2008) pp. 377-388.

Huang, T. F., et al. "Viper Venom Components Affecting Angiogenesis." Haemostasis, vol. 31 (2001) pp. 192-206.

International Preliminary Report on Palatability (Form PCT/IB/373) for International Patent Application No. PCT/B2016/053794 issued from the International Bureau of WIPO, dated Jan. 2, 2018, 9 pages.

Patel, Samir, "Combination Therapy for Age-Related Macular Degeneration," Retina, The Journal of Retinal and Vitreous Diseases, vol. 29, No. 6, (2009) pp. S45-S48.

Jing, Yawu et al., "Abstract 1385: Fusion Protein containing RGD-endostatin and human Fc of IgG4 improves anti-angiogenic and anti-tumor activity," Cancer Research, vol. 70, (2010) Abstract.

Wu, Jueheng et al., "Dual Function of RGD-Modified VEGI-192 for Breast Cancer Treatment," Bioconjugate Chemistry, vol. 23 (2012) pp. 786-804.

International Search Report (Form PCT/ISA/210) for International Patent Application No. PCT/IB2016/053794, issued from the International Searching Authority, dated Dec. 16, 2016, 12 pages.

Kluza, Ewelina et al. "Synergistic Targeting of $\alpha v\beta 3$ Integrin and Galectin-1 with Heteromultivalent Paramagnetic Liposomes for Combined MR Imaging and Treatment of Angiogenesis," Nano Letters, vol. 10 (2010) pp. 52-58.

Kwan, Byron et al. "Tumor vasculature targeting for improving solid tumor delivery of cancer therapeutics," Protein Society, vol. 21, supplement 1, Abstract No. 155 (Aug. 2012).

Peiru, Jiang, Design of Integrin $\alpha 5\beta 1$-specific Disintegrin Using Rhodostomin as the Scaffold. National Cheng Kung University. Institute of Biochemistry and Molecular Biology. Doctoral thesis, Jul. 21, 2009. Abstract.

\* cited by examiner

• Histidine buffer

SEQUENCE LISTING

```
<160> NUMBER OF SEQ ID NOS: 70

<210> SEQ ID NO 1
<211> LENGTH: 68
<212> TYPE: PRT
<213> ORGANISM: Unknown
<220> FEATURE:
<223> OTHER INFORMATION: Rhodostomin

<400> SEQUENCE: 1

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Pro
        35                  40                  45

Arg Gly Asp Met Pro Asp Asp Arg Cys Thr Gly Gln Ser Ala Asp Cys
    50                  55                  60

Pro Arg Tyr His
65

<210> SEQ ID NO 2
<211> LENGTH: 68
<212> TYPE: PRT
<213> ORGANISM: Artificial Sequence
<220> FEATURE:
<221> NAME/KEY: VARIANT
<222> LOCATION: 39, 40, 41, 42, 43, 46, 47, 48, 50, 52, 53, 65, 66, 67,
      68
<223> OTHER INFORMATION: Xaa = Any Amino Acid
<220> FEATURE:
<223> OTHER INFORMATION: Rhodostomin mutant

<400> SEQUENCE: 2

Gly Lys Glu Cys Asp Cys Ser Ser Pro Glu Asn Pro Cys Cys Asp Ala
1               5                   10                  15
```

```
Ala Thr Cys Lys Leu Arg Pro Gly Ala Gln Cys Gly Glu Gly Leu Cys
            20                  25                  30

Cys Glu Gln Cys Lys Phe Xaa Xaa Xaa Xaa Ile Cys Xaa Xaa
        35                  40                  45

Arg Xaa Asp Xaa Xaa Asp Asp Arg Cys Thr Gly Gln Ser Ala Asp Cys
    50                  55                  60

Xaa Xaa Xaa Xaa
65

<210> SEQ ID NO 3
<211> LENGTH: 70
<212> TYPE: PRT
<213> ORGANISM: Unknown
<220> FEATURE:
<223> OTHER INFORMATION: Rhodostomin mutant

<400> SEQUENCE: 3

Gly Glu Glu Cys Asp Cys Gly Ser Pro Ser Asn Pro Cys Cys Asp Ala
1               5                   10                  15

Ala Thr Cys Lys Leu Arg Pro Gly Ala Gln Cys Ala Asp Gly Leu Cys
            20                  25                  30

Cys Asp Gln Cys Arg Phe Lys Lys Lys Arg Thr Ile Cys Arg Ile Ala
        35                  40                  45

Arg Gly Asp Phe Pro Asp Arg Cys Thr Gly Gln Ser Ala Asp Cys
    50                  55                  60

Pro Arg Trp Asn Gly Leu
65                  70

<210> SEQ ID NO 4
<211> LENGTH: 49
<212> TYPE: PRT
<213> ORGANISM: Unknown
<220> FEATURE:
<223> OTHER INFORMATION: Echistatin

<400> SEQUENCE: 4

Gln Cys Glu Ser Gly Pro Cys Cys Arg Asn Cys Lys Phe Leu Lys Glu
1               5                   10                  15

Gly Thr Ile Cys Lys Arg Ala Arg Gly Asp Asp Met Asp Asp Tyr Cys
            20                  25                  30

Asn Gly Lys Thr Cys Asp Cys Pro Arg Asn Pro His Lys Gly Pro Ala
        35                  40                  45

Thr

<210> SEQ ID NO 5
<211> LENGTH: 73
<212> TYPE: PRT
<213> ORGANISM: Unknown
<220> FEATURE:
<223> OTHER INFORMATION: Trimucrin

<400> SEQUENCE: 5

Glu Ala Gly Glu Glu Cys Asp Cys Gly Ser Pro Glu Asn Pro Cys Cys
1               5                   10                  15

Asp Ala Ala Thr Cys Lys Leu Arg Pro Gly Ala Gln Cys Ala Glu Gly
            20                  25                  30

Leu Cys Cys Asp Gln Cys Arg Phe Lys Lys Lys Arg Thr Ile Cys Arg
        35                  40                  45

Arg Ala Arg Gly Asp Asn Pro Asp Asp Arg Cys Thr Gly Gln Ser Ala
    50                  55                  60
```

```
Asp Cys Pro Arg Asn Gly Leu Tyr Gly
65                  70

<210> SEQ ID NO 6
<211> LENGTH: 73
<212> TYPE: PRT
<213> ORGANISM: Unknown
<220> FEATURE:
<223> OTHER INFORMATION: Elegantin

<400> SEQUENCE: 6

Glu Ala Gly Glu Glu Cys Asp Cys Gly Ser Pro Glu Asn Pro Cys Cys
1               5                   10                  15

Asp Ala Ala Thr Cys Lys Leu Arg Pro Gly Ala Gln Cys Ala Asp Gly
            20                  25                  30

Leu Cys Cys Asp Gln Cys Arg Phe Lys Lys Arg Thr Ile Cys Arg
        35                  40                  45

Arg Ala Arg Gly Asp Asn Pro Asp Asp Arg Cys Thr Gly Gln Ser Ala
    50                  55                  60

Asp Cys Pro Arg Asn Gly Leu Tyr Ser
65                  70

<210> SEQ ID NO 7
<211> LENGTH: 62
<212> TYPE: PRT
<213> ORGANISM: Unknown
<220> FEATURE:
<223> OTHER INFORMATION: Trigramin

<400> SEQUENCE: 7

Glu Ala Gly Glu Asp Cys Asp Cys Gly Ser Pro Ser Asn Pro Cys Cys
1               5                   10                  15

Asp Ala Ala Thr Cys Lys Leu Ile Pro Gly Ala Gln Cys Gly Glu Gly
            20                  25                  30

Leu Cys Cys Asp Gln Cys Ser Phe Ile Glu Gly Thr Val Cys Arg
        35                  40                  45

Ile Ala Arg Gly Asp Asp Leu Asp Asp Tyr Cys Asn Gly Arg
    50                  55                  60

<210> SEQ ID NO 8
<211> LENGTH: 100
<212> TYPE: PRT
<213> ORGANISM: Artificial Sequence
<220> FEATURE:
<223> OTHER INFORMATION: VEGFR1 extracellular domain D2

<400> SEQUENCE: 8

Gly Arg Pro Phe Val Glu Met Tyr Ser Glu Ile Pro Glu Ile Ile His
1               5                   10                  15

Met Thr Glu Gly Arg Glu Leu Val Ile Pro Cys Arg Val Thr Ser Pro
            20                  25                  30

Asn Ile Thr Val Thr Leu Lys Lys Phe Pro Leu Asp Thr Leu Ile Pro
        35                  40                  45

Asp Gly Lys Arg Ile Ile Trp Asp Ser Arg Lys Gly Phe Ile Ile Ser
    50                  55                  60

Asn Ala Thr Tyr Lys Glu Ile Gly Leu Leu Thr Cys Glu Ala Thr Val
65                  70                  75                  80

Asn Gly His Leu Tyr Lys Thr Asn Tyr Leu Thr His Arg Gln Thr Asn
                85                  90                  95
```

Thr Ile Ile Asp
            100

<210> SEQ ID NO 9
<211> LENGTH: 102
<212> TYPE: PRT
<213> ORGANISM: Artificial Sequence
<220> FEATURE:
<223> OTHER INFORMATION: VEGFR2 extracellular domain D3

<400> SEQUENCE: 9

Val Val Leu Ser Pro Ser His Gly Ile Glu Leu Ser Val Gly Glu Lys
1               5                   10                  15

Leu Val Leu Asn Cys Thr Ala Arg Thr Glu Leu Asn Val Gly Ile Asp
            20                  25                  30

Phe Asn Trp Glu Tyr Pro Ser Ser Lys His Gln His Lys Lys Leu Val
        35                  40                  45

Asn Arg Asp Leu Lys Thr Gln Ser Gly Ser Glu Met Lys Lys Phe Leu
    50                  55                  60

Ser Thr Leu Thr Ile Asp Gly Val Thr Arg Ser Asp Gln Gly Leu Tyr
65                  70                  75                  80

Thr Cys Ala Ala Ser Ser Gly Leu Met Thr Lys Lys Asn Ser Thr Phe
                85                  90                  95

Val Arg Val His Glu Lys
            100

<210> SEQ ID NO 10
<211> LENGTH: 202
<212> TYPE: PRT
<213> ORGANISM: Artificial Sequence
<220> FEATURE:
<223> OTHER INFORMATION: VEGFR1 extracellular domain D2/VEGFR2
      extracellular domain D3

<400> SEQUENCE: 10

Gly Arg Pro Phe Val Glu Met Tyr Ser Glu Ile Pro Glu Ile Ile His
1               5                   10                  15

Met Thr Glu Gly Arg Glu Leu Val Ile Pro Cys Arg Val Thr Ser Pro
            20                  25                  30

Asn Ile Thr Val Thr Leu Lys Lys Phe Pro Leu Asp Thr Leu Ile Pro
        35                  40                  45

Asp Gly Lys Arg Ile Ile Trp Asp Ser Arg Lys Gly Phe Ile Ile Ser
    50                  55                  60

Asn Ala Thr Tyr Lys Glu Ile Gly Leu Leu Thr Cys Glu Ala Thr Val
65                  70                  75                  80

Asn Gly His Leu Tyr Lys Thr Asn Tyr Leu Thr His Arg Gln Thr Asn
                85                  90                  95

Thr Ile Ile Asp Val Val Leu Ser Pro Ser His Gly Ile Glu Leu Ser
            100                 105                 110

Val Gly Glu Lys Leu Val Leu Asn Cys Thr Ala Arg Thr Glu Leu Asn
        115                 120                 125

Val Gly Ile Asp Phe Asn Trp Glu Tyr Pro Ser Ser Lys His Gln His
    130                 135                 140

Lys Lys Leu Val Asn Arg Asp Leu Lys Thr Gln Ser Gly Ser Glu Met
145                 150                 155                 160

Lys Lys Phe Leu Ser Thr Leu Thr Ile Asp Gly Val Thr Arg Ser Asp
                165                 170                 175

Gln Gly Leu Tyr Thr Cys Ala Ala Ser Ser Gly Leu Met Thr Lys Lys

```
                    180                 185                 190
Asn Ser Thr Phe Val Arg Val His Glu Lys
            195                 200

<210> SEQ ID NO 11
<211> LENGTH: 299
<212> TYPE: PRT
<213> ORGANISM: Artificial Sequence
<220> FEATURE:
<223> OTHER INFORMATION: PDGFR-beta extracellular domains D1-D3

<400> SEQUENCE: 11

Gln Gly Leu Val Val Thr Pro Pro Gly Pro Glu Leu Val Leu Asn Val
1               5                   10                  15

Ser Ser Thr Phe Val Leu Thr Cys Ser Gly Ser Ala Pro Val Val Trp
            20                  25                  30

Glu Arg Met Ser Gln Glu Pro Pro Gln Glu Met Ala Lys Ala Gln Asp
        35                  40                  45

Gly Thr Phe Ser Ser Val Leu Thr Leu Thr Asn Leu Thr Gly Leu Asp
    50                  55                  60

Thr Gly Glu Tyr Phe Cys Thr His Asn Asp Ser Arg Gly Leu Glu Thr
65                  70                  75                  80

Asp Glu Arg Lys Arg Leu Tyr Ile Phe Val Pro Asp Pro Thr Val Gly
                85                  90                  95

Phe Leu Pro Asn Asp Ala Glu Glu Leu Phe Ile Phe Leu Thr Glu Ile
            100                 105                 110

Thr Glu Ile Thr Ile Pro Cys Arg Val Thr Asp Pro Gln Leu Val Val
        115                 120                 125

Thr Leu His Glu Lys Lys Gly Asp Val Ala Leu Pro Val Pro Tyr Asp
    130                 135                 140

His Gln Arg Gly Phe Phe Gly Ile Phe Glu Asp Arg Ser Tyr Ile Cys
145                 150                 155                 160

Lys Thr Thr Ile Gly Asp Arg Glu Val Asp Ser Asp Ala Tyr Tyr Val
                165                 170                 175

Tyr Arg Leu Gln Val Ser Ser Ile Asn Val Ser Val Asn Ala Val Gln
            180                 185                 190

Thr Val Val Arg Gln Gly Glu Asn Ile Thr Leu Met Cys Ile Val Ile
        195                 200                 205

Gly Asn Glu Val Val Asn Phe Glu Trp Thr Tyr Pro Arg Lys Glu Ser
    210                 215                 220

Gly Arg Leu Val Glu Pro Val Thr Asp Phe Leu Leu Asp Met Pro Tyr
225                 230                 235                 240

His Ile Arg Ser Ile Leu His Ile Pro Ser Ala Glu Leu Glu Asp Ser
                245                 250                 255

Gly Thr Tyr Thr Cys Asn Val Thr Glu Ser Val Asn Asp His Gln Asp
            260                 265                 270

Glu Lys Ala Ile Asn Ile Thr Val Val Glu Ser Gly Tyr Val Arg Leu
        275                 280                 285

Leu Gly Glu Val Gly Thr Leu Gln Phe Ala Glu
    290                 295

<210> SEQ ID NO 12
<211> LENGTH: 70
<212> TYPE: PRT
<213> ORGANISM: Artificial Sequence
<220> FEATURE:
<223> OTHER INFORMATION: Rhodostomin variant KG-WN
```

<400> SEQUENCE: 12

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Ala Arg Thr Ile Cys Ala Arg Gly
        35                  40                  45

Arg Gly Asp Asn Pro Asp Asp Arg Cys Thr Gly Gln Ser Ala Asp Cys
    50                  55                  60

Pro Arg Trp Asn Asp Leu
65                  70

<210> SEQ ID NO 13
<211> LENGTH: 68
<212> TYPE: PRT
<213> ORGANISM: Artificial Sequence
<220> FEATURE:
<223> OTHER INFORMATION: Rhodostomin variant KG

<400> SEQUENCE: 13

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Ala Arg Thr Ile Cys Ala Arg Gly
        35                  40                  45

Arg Gly Asp Asn Pro Asp Asp Arg Cys Thr Gly Gln Ser Ala Asp Cys
    50                  55                  60

Pro Arg Tyr His
65

<210> SEQ ID NO 14
<211> LENGTH: 68
<212> TYPE: PRT
<213> ORGANISM: Artificial Sequence
<220> FEATURE:
<223> OTHER INFORMATION: Rhodostomin variant KA

<400> SEQUENCE: 14

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Ala Arg Thr Ile Cys Ala Arg Ala
        35                  40                  45

Arg Gly Asp Asn Pro Asp Asp Arg Cys Thr Gly Gln Ser Ala Asp Cys
    50                  55                  60

Pro Arg Tyr His
65

<210> SEQ ID NO 15
<211> LENGTH: 517
<212> TYPE: PRT
<213> ORGANISM: Artificial Sequence
<220> FEATURE:
<223> OTHER INFORMATION: Fusion of VEGFR1 D2/VEGFR2 D3 and Rhodostomin
      variant KG-WN

<400> SEQUENCE: 15

-continued

```
Gly Arg Pro Phe Val Glu Met Tyr Ser Glu Ile Pro Glu Ile Ile His
1               5                   10                  15

Met Thr Glu Gly Arg Glu Leu Val Ile Pro Cys Arg Val Thr Ser Pro
            20                  25                  30

Asn Ile Thr Val Thr Leu Lys Lys Phe Pro Leu Asp Thr Leu Ile Pro
                35                  40                  45

Asp Gly Lys Arg Ile Ile Trp Asp Ser Arg Lys Gly Phe Ile Ile Ser
    50                  55                  60

Asn Ala Thr Tyr Lys Glu Ile Gly Leu Leu Thr Cys Glu Ala Thr Val
65                  70                  75                  80

Asn Gly His Leu Tyr Lys Thr Asn Tyr Leu Thr His Arg Gln Thr Asn
                85                  90                  95

Thr Ile Ile Asp Val Val Leu Ser Pro Ser His Gly Ile Glu Leu Ser
                100                 105                 110

Val Gly Glu Lys Leu Val Leu Asn Cys Thr Ala Arg Thr Glu Leu Asn
            115                 120                 125

Val Gly Ile Asp Phe Asn Trp Glu Tyr Pro Ser Ser Lys His Gln His
    130                 135                 140

Lys Lys Leu Val Asn Arg Asp Leu Lys Thr Gln Ser Gly Ser Glu Met
145                 150                 155                 160

Lys Lys Phe Leu Ser Thr Leu Thr Ile Asp Gly Val Thr Arg Ser Asp
                165                 170                 175

Gln Gly Leu Tyr Thr Cys Ala Ala Ser Ser Gly Leu Met Thr Lys Lys
                180                 185                 190

Asn Ser Thr Phe Val Arg Val His Glu Lys Gly Pro Gly Asp Lys Thr
            195                 200                 205

His Thr Cys Pro Pro Cys Pro Ala Pro Glu Leu Leu Gly Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
                260                 265                 270

Lys Thr Lys Pro Arg Glu Glu Gln Tyr Asn Ser Thr Tyr Arg Val Val
            275                 280                 285

Ser Val Leu Thr Val Leu His Gln Asp Trp Leu Asn Gly Lys Glu Tyr
    290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Asp Glu Leu Thr Lys Asn Gln Val Ser Leu Thr Cys
            340                 345                 350

Leu Val Lys Gly Phe Tyr Pro Ser Asp Ile Ala Val Glu Trp Glu Ser
            355                 360                 365

Asn Gly Gln Pro Glu Asn Asn Tyr Lys Thr Thr Pro Pro Val Leu Asp
    370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly Lys
```

```
            420                 425                 430
Gly Gly Gly Gly Ser Gly Gly Gly Ser Gly Gly Gly Ser Gly
            435                 440                 445

Lys Glu Cys Asp Cys Ser Ser Pro Glu Asn Pro Cys Cys Asp Ala Ala
            450                 455                 460

Thr Cys Lys Leu Arg Pro Gly Ala Gln Cys Gly Glu Gly Leu Cys Cys
465                 470                 475                 480

Glu Gln Cys Lys Phe Lys Lys Ala Arg Thr Ile Cys Ala Arg Gly Arg
                485                 490                 495

Gly Asp Asn Pro Asp Asp Arg Cys Thr Gly Gln Ser Ala Asp Cys Pro
            500                 505                 510

Arg Trp Asn Asp Leu
            515

<210> SEQ ID NO 16
<211> LENGTH: 516
<212> TYPE: PRT
<213> ORGANISM: Artificial Sequence
<220> FEATURE:
<223> OTHER INFORMATION: Fusion of VEGFR1 D2/VEGFR2 D3 and Rhodostomin
      variant KG

<400> SEQUENCE: 16

Ser Gly Gly Arg Pro Phe Val Glu Met Tyr Ser Glu Ile Pro Glu Ile
1               5                   10                  15

Ile His Met Thr Glu Gly Arg Glu Leu Val Ile Pro Cys Arg Val Thr
            20                  25                  30

Ser Pro Asn Ile Thr Val Thr Leu Lys Lys Phe Pro Leu Asp Thr Leu
        35                  40                  45

Ile Pro Asp Gly Lys Arg Ile Ile Trp Asp Ser Arg Lys Gly Phe Ile
    50                  55                  60

Ile Ser Asn Ala Thr Tyr Lys Glu Ile Gly Leu Leu Thr Cys Glu Ala
65                  70                  75                  80

Thr Val Asn Gly His Leu Tyr Lys Thr Asn Tyr Leu Thr His Arg Gln
                85                  90                  95

Thr Asn Thr Ile Ile Asp Val Val Leu Ser Pro Ser His Gly Ile Glu
            100                 105                 110

Leu Ser Val Gly Glu Lys Leu Val Leu Asn Cys Thr Ala Arg Thr Glu
        115                 120                 125

Leu Asn Val Gly Ile Asp Phe Asn Trp Glu Tyr Pro Ser Ser Lys His
    130                 135                 140

Gln His Lys Lys Leu Val Asn Arg Asp Leu Lys Thr Gln Ser Gly Ser
145                 150                 155                 160

Glu Met Lys Lys Phe Leu Ser Thr Leu Thr Ile Asp Gly Val Thr Arg
                165                 170                 175

Ser Asp Gln Gly Leu Tyr Thr Cys Ala Ala Ser Ser Gly Leu Met Thr
            180                 185                 190

Lys Lys Asn Ser Thr Phe Val Arg Val His Glu Lys Gly Pro Gly Asp
        195                 200                 205

Lys Thr His Thr Cys Pro Pro Cys Pro Ala Pro Glu Leu Leu Gly Gly
    210                 215                 220

Pro Ser Val Phe Leu Phe Pro Pro Lys Pro Lys Asp Thr Leu Met Ile
225                 230                 235                 240

Ser Arg Thr Pro Glu Val Thr Cys Val Val Val Asp Val Ser His Glu
                245                 250                 255
```

```
Asp Pro Glu Val Lys Phe Asn Trp Tyr Val Asp Gly Val Glu Val His
            260                 265                 270

Asn Ala Lys Thr Lys Pro Arg Glu Glu Gln Tyr Asn Ser Thr Tyr Arg
        275                 280                 285

Val Val Ser Val Leu Thr Val Leu His Gln Asp Trp Leu Asn Gly Lys
    290                 295                 300

Glu Tyr Lys Cys Lys Val Ser Asn Lys Ala Leu Pro Ala Pro Ile Glu
305                 310                 315                 320

Lys Thr Ile Ser Lys Ala Lys Gly Gln Pro Arg Glu Pro Gln Val Tyr
                325                 330                 335

Thr Leu Pro Pro Ser Arg Asp Glu Leu Thr Lys Asn Gln Val Ser Leu
            340                 345                 350

Thr Cys Leu Val Lys Gly Phe Tyr Pro Ser Asp Ile Ala Val Glu Trp
        355                 360                 365

Glu Ser Asn Gly Gln Pro Glu Asn Asn Tyr Lys Thr Thr Pro Pro Val
    370                 375                 380

Leu Asp Ser Asp Gly Ser Phe Phe Leu Tyr Ser Lys Leu Thr Val Asp
385                 390                 395                 400

Lys Ser Arg Trp Gln Gln Gly Asn Val Phe Ser Cys Ser Val Met His
                405                 410                 415

Glu Ala Leu His Asn His Tyr Thr Gln Lys Ser Leu Ser Leu Ser Pro
            420                 425                 430

Gly Gly Gly Gly Ser Gly Gly Gly Ser Gly Gly Gly Gly Ser
        435                 440                 445

Gly Lys Glu Cys Asp Cys Ser Ser Pro Glu Asn Pro Cys Cys Asp Ala
450                 455                 460

Ala Thr Cys Lys Leu Arg Pro Gly Ala Gln Cys Gly Glu Gly Leu Cys
465                 470                 475                 480

Cys Glu Gln Cys Lys Phe Lys Lys Ala Arg Thr Ile Cys Ala Arg Gly
                485                 490                 495

Arg Gly Asp Asn Pro Asp Asp Arg Cys Thr Gly Gln Ser Ala Asp Cys
            500                 505                 510

Pro Arg Tyr His
        515

<210> SEQ ID NO 17
<211> LENGTH: 515
<212> TYPE: PRT
<213> ORGANISM: Artificial Sequence
<220> FEATURE:
<223> OTHER INFORMATION: Fusion of VEGFR1 D2/VEGFR2 D3 and Rhodostomin
      variant KA

<400> SEQUENCE: 17

Gly Arg Pro Phe Val Glu Met Tyr Ser Glu Ile Pro Glu Ile Ile His
1               5                   10                  15

Met Thr Glu Gly Arg Glu Leu Val Ile Pro Cys Arg Val Thr Ser Pro
            20                  25                  30

Asn Ile Thr Val Thr Leu Lys Lys Phe Pro Leu Asp Thr Leu Ile Pro
        35                  40                  45

Asp Gly Lys Arg Ile Ile Trp Asp Ser Arg Lys Gly Phe Ile Ile Ser
    50                  55                  60

Asn Ala Thr Tyr Lys Glu Ile Gly Leu Leu Thr Cys Glu Ala Thr Val
65                  70                  75                  80

Asn Gly His Leu Tyr Lys Thr Asn Tyr Leu Thr His Arg Gln Thr Asn
                85                  90                  95
```

```
Thr Ile Ile Asp Val Val Leu Ser Pro Ser His Gly Ile Glu Leu Ser
            100                 105                 110

Val Gly Glu Lys Leu Val Leu Asn Cys Thr Ala Arg Thr Glu Leu Asn
        115                 120                 125

Val Gly Ile Asp Phe Asn Trp Glu Tyr Pro Ser Ser Lys His Gln His
    130                 135                 140

Lys Lys Leu Val Asn Arg Asp Leu Lys Thr Gln Ser Gly Ser Glu Met
145                 150                 155                 160

Lys Lys Phe Leu Ser Thr Leu Thr Ile Asp Gly Val Thr Arg Ser Asp
                165                 170                 175

Gln Gly Leu Tyr Thr Cys Ala Ala Ser Ser Gly Leu Met Thr Lys Lys
            180                 185                 190

Asn Ser Thr Phe Val Arg Val His Glu Lys Gly Pro Gly Asp Lys Thr
        195                 200                 205

His Thr Cys Pro Pro Cys Pro Ala Pro Glu Leu Leu Gly Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
    290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Asp Glu Leu Thr Lys Asn Gln Val Ser Leu Thr Cys
            340                 345                 350

Leu Val Lys Gly Phe Tyr Pro Ser Asp Ile Ala Val Glu Trp Glu Ser
        355                 360                 365

Asn Gly Gln Pro Glu Asn Asn Tyr Lys Thr Thr Pro Pro Val Leu Asp
    370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly Lys
            420                 425                 430

Gly Gly Gly Gly Ser Gly Gly Gly Ser Gly Gly Gly Gly Ser Gly
        435                 440                 445

Lys Glu Cys Asp Cys Ser Ser Pro Glu Asn Pro Cys Cys Asp Ala Ala
    450                 455                 460

Thr Cys Lys Leu Arg Pro Gly Ala Gln Cys Gly Glu Gly Leu Cys Cys
465                 470                 475                 480

Glu Gln Cys Lys Phe Lys Lys Ala Arg Thr Ile Cys Ala Arg Ala Arg
                485                 490                 495

Gly Asp Asn Pro Asp Asp Arg Cys Thr Gly Gln Ser Ala Asp Cys Pro
            500                 505                 510
```

Arg Tyr His
        515

<210> SEQ ID NO 18
<211> LENGTH: 514
<212> TYPE: PRT
<213> ORGANISM: Artificial Sequence
<220> FEATURE:
<223> OTHER INFORMATION: Fusion of Eylea and Rhodostomin variant KG

<400> SEQUENCE: 18

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Ala Pro Glu Leu Leu Gly Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
    290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Asp Glu Leu Thr Lys Asn Gln Val Ser Leu Thr Cys
            340                 345                 350

```
Leu Val Lys Gly Phe Tyr Pro Ser Asp Ile Ala Val Glu Trp Glu Ser
            355                 360                 365

Asn Gly Gln Pro Glu Asn Asn Tyr Lys Thr Thr Pro Pro Val Leu Asp
        370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly Gly
            420                 425                 430

Gly Gly Gly Ser Gly Gly Gly Ser Gly Gly Gly Gly Ser Gly Lys
        435                 440                 445

Glu Cys Asp Cys Ser Ser Pro Glu Asn Pro Cys Cys Asp Ala Ala Thr
    450                 455                 460

Cys Lys Leu Arg Pro Gly Ala Gln Cys Gly Glu Gly Leu Cys Cys Glu
465                 470                 475                 480

Gln Cys Lys Phe Lys Lys Ala Arg Thr Ile Cys Ala Arg Gly Arg Gly
                485                 490                 495

Asp Asn Pro Asp Asp Arg Cys Thr Gly Gln Ser Ala Asp Cys Pro Arg
            500                 505                 510

Tyr His

<210> SEQ ID NO 19
<211> LENGTH: 1551
<212> TYPE: DNA
<213> ORGANISM: Artificial Sequence
<220> FEATURE:
<223> OTHER INFORMATION: nucleotide sequence of fusion protein of SEQ ID
      NO: 16

<400> SEQUENCE: 19
agcggcggaa ggcctttcgt cgagatgtac agcgagatcc ccgagatcat tcacatgacc      60
gaaggcaggg agctcgtgat cccttgcagg gtcacatccc ccaacatcac cgtcaccctc     120
aagaagttcc ccctggatac cctcatcccc gacggcaagc ggatcatttg ggatagccgg     180
aagggcttca tcatctccaa cgctacctac aaagaaattg actgctgac ctgcgaggct     240 accgtcaacg gccacctcta taagaccaac tacctgaccc acaggcagac caataccatc     300
atcgatgtgg tcctcagccc cagccacgga atcgaactgt ccgtgggcga aagctggtc     360 ctgaactgta cagccaggac agaactcaac gtgggcatcg acttcaactg ggagtaccct     420
agctccaagc accagcacaa gaagctggtc aaccgggacc tgaagaccca gtccggctcc     480
gaaatgaaga agttcctgtc caccctcacc atcgatggag tcacccggag cgatcaggga     540
ctgtatacct gcgccgcctc ctccggcctg atgacaaaga gaacagcac cttcgtgcgg     600 gtgcacgaga aggccccgg cgacaagaca cacacctgcc ctccctgccc cgccccgag     660 ctgctcggcg gacccagcgt gttcctgttc cccctaagc caaggacac cctcatgatc     720 agcaggaccc ctgaggtgac atgcgtcgtc gtggacgtga gccatgaaga ccccgaggtg     780
aagttcaact ggtatgtgga cggcgtcgag gtgcataacg ccaagaccaa accccgggag     840
gagcaataca acagcacata cagggtggtg tccgtgctga ccgtcctgca ccaggattgg     900
ctgaacggca agagtataa gtgcaaggtg agcaacaaag ccctgccgc tcccatcgag     960 aagacaatct ccaaggccaa gggccaaccc agggagcctc aggtgtacac actgcctcct    1020
tcccgggacg agctgacaaa aaaccaagtg agcctgacct gcctcgtcaa gggcttctac    1080
```

-continued

```
ccttccgata tcgccgtgga gtgggagtcc aacggccagc ctgagaacaa ctacaagacc    1140 accctcccg tgctcgattc cgacggctcc ttcttcctct acagcaagct cacagtggac     1200
aaatcccggt ggcagcaggg caatgtgttc agctgttccg tgatgcacga ggccctccac    1260
aatcactaca cccagaagag cctgtccctg tccccggcg gaggcggcgg ctccggcgga     1320
ggcggctccg gcggcggcgg atccggaaaa gagtgcgatt gcagctcccc cgagaacccc    1380
tgctgcgatg ccgctacatg caaactgcgg cctggagccc agtgtggaga aggcctgtgc    1440
tgcgagcagt gcaagttcaa gaaggcccgg accatttgtg ctaggggccg gggagacaac    1500
cctgacgatc ggtgcaccgg ccaaagcgct gactgtcccc ggtaccactg a             1551
```

<210> SEQ ID NO 20
<211> LENGTH: 19
<212> TYPE: PRT
<213> ORGANISM: Artificial Sequence
<220> FEATURE:
<223> OTHER INFORMATION: A Signal Peptide

<400> SEQUENCE: 20

Met Ala Trp Ala Leu Leu Leu Leu Thr Leu Leu Thr Arg Asp Thr Gly
1               5                   10                  15

Ser Trp Ala

<210> SEQ ID NO 21
<211> LENGTH: 57
<212> TYPE: DNA
<213> ORGANISM: Artificial Sequence
<220> FEATURE:
<223> OTHER INFORMATION: Nucleotide Sequence of a Signal Peptide

<400> SEQUENCE: 21

```
atggcctggg ctctcctgct gctgaccctg ctgacacggg acacaggatc ctgggcc      57
```

<210> SEQ ID NO 22
<211> LENGTH: 26
<212> TYPE: PRT
<213> ORGANISM: Artificial Sequence
<220> FEATURE:
<223> OTHER INFORMATION: Signaling Peptide of Fusion Protein of SEQ ID
      NO: 18

<400> SEQUENCE: 22

Met Val Ser Tyr Trp Asp Thr Gly Val Leu Leu Cys Ala Leu Leu Ser
1               5                   10                  15

Cys Leu Leu Leu Thr Gly Ser Ser Ser Gly
            20                  25

<210> SEQ ID NO 23
<211> LENGTH: 431
<212> TYPE: PRT
<213> ORGANISM: Artificial Sequence
<220> FEATURE:
<223> OTHER INFORMATION: VEGFR1 domain D2/VEGFR2 domain D3 fused to IgG1
      Fc

<400> SEQUENCE: 23

Asp Thr Gly Arg Pro Phe Val Glu Met Tyr Ser Glu Ile Pro Glu Ile
1               5                   10                  15

Ile His Met Thr Glu Gly Arg Glu Leu Val Ile Pro Cys Arg Val Thr
                20                  25                  30

Ser Pro Asn Ile Thr Val Thr Leu Lys Lys Phe Pro Leu Asp Thr Leu
            35                  40                  45

Ile Pro Asp Gly Lys Arg Ile Ile Trp Asp Ser Arg Lys Gly Phe Ile
 50                  55                  60

Ile Ser Asn Ala Thr Tyr Lys Glu Ile Gly Leu Leu Thr Cys Glu Ala
 65                  70                  75                  80

Thr Val Asn Gly His Leu Tyr Lys Thr Asn Tyr Leu Thr His Arg Gln
                 85                  90                  95

Thr Asn Thr Ile Ile Asp Val Val Leu Ser Pro Ser His Gly Ile Glu
                100                 105                 110

Leu Ser Val Gly Glu Lys Leu Val Leu Asn Cys Thr Ala Arg Thr Glu
            115                 120                 125

Leu Asn Val Gly Ile Asp Phe Asn Trp Glu Tyr Pro Ser Ser Lys His
130                 135                 140

Gln His Lys Lys Leu Val Asn Arg Asp Leu Lys Thr Gln Ser Gly Ser
145                 150                 155                 160

Glu Met Lys Lys Phe Leu Ser Thr Leu Thr Ile Asp Gly Val Thr Arg
                165                 170                 175

Ser Asp Gln Gly Leu Tyr Thr Cys Ala Ala Ser Ser Gly Leu Met Thr
                180                 185                 190

Lys Lys Asn Ser Thr Phe Val Arg Val His Glu Lys Asp Lys Thr His
            195                 200                 205

Thr Cys Pro Pro Cys Pro Ala Pro Glu Leu Leu Gly Gly Pro Ser Val
210                 215                 220

Phe Leu Phe Pro Pro Lys Pro Lys Asp Thr Leu Met Ile Ser Arg Thr
225                 230                 235                 240

Pro Glu Val Thr Cys Val Val Val Asp Val Ser His Glu Asp Pro Glu
                245                 250                 255

Val Lys Phe Asn Trp Tyr Val Asp Gly Val Glu Val His Asn Ala Lys
                260                 265                 270

Thr Lys Pro Arg Glu Glu Gln Tyr Asn Ser Thr Tyr Arg Val Val Ser
            275                 280                 285

Val Leu Thr Val Leu His Gln Asp Trp Leu Asn Gly Lys Glu Tyr Lys
290                 295                 300

Cys Lys Val Ser Asn Lys Ala Leu Pro Ala Pro Ile Glu Lys Thr Ile
305                 310                 315                 320

Ser Lys Ala Lys Gly Gln Pro Arg Glu Pro Gln Val Tyr Thr Leu Pro
                325                 330                 335

Pro Ser Arg Asp Glu Leu Thr Lys Asn Gln Val Ser Leu Thr Cys Leu
                340                 345                 350

Val Lys Gly Phe Tyr Pro Ser Asp Ile Ala Val Glu Trp Glu Ser Asn
            355                 360                 365

Gly Gln Pro Glu Asn Asn Tyr Lys Thr Thr Pro Pro Val Leu Asp Ser
370                 375                 380

Asp Gly Ser Phe Phe Leu Tyr Ser Lys Leu Thr Val Asp Lys Ser Arg
385                 390                 395                 400

Trp Gln Gln Gly Asn Val Phe Ser Cys Ser Val Met His Glu Ala Leu
                405                 410                 415

His Asn His Tyr Thr Gln Lys Ser Leu Ser Leu Ser Pro Gly Lys
                420                 425                 430

<210> SEQ ID NO 24
<211> LENGTH: 8
<212> TYPE: PRT
<213> ORGANISM: Artificial Sequence
<220> FEATURE:

```
<223> OTHER INFORMATION: mutant RGD

<400> SEQUENCE: 24

Arg Ile Ala Arg Gly Asp Asn Pro
1               5

<210> SEQ ID NO 25
<211> LENGTH: 8
<212> TYPE: PRT
<213> ORGANISM: Artificial Sequence
<220> FEATURE:
<223> OTHER INFORMATION: mutant RGD

<400> SEQUENCE: 25

Arg Arg Ala Arg Gly Asp Asn Pro
1               5

<210> SEQ ID NO 26
<211> LENGTH: 8
<212> TYPE: PRT
<213> ORGANISM: Artificial Sequence
<220> FEATURE:
<223> OTHER INFORMATION: mutant RGD

<400> SEQUENCE: 26

Ala Arg Gly Arg Gly Asp Asn Pro
1               5

<210> SEQ ID NO 27
<211> LENGTH: 8
<212> TYPE: PRT
<213> ORGANISM: Artificial Sequence
<220> FEATURE:
<223> OTHER INFORMATION: mutant RGD loop sequence

<400> SEQUENCE: 27

Ala Arg Gly Arg Gly Asp Asp Leu
1               5

<210> SEQ ID NO 28
<211> LENGTH: 8
<212> TYPE: PRT
<213> ORGANISM: Artificial Sequence
<220> FEATURE:
<223> OTHER INFORMATION: mutant RGD loop sequence

<400> SEQUENCE: 28

Ala Arg Ala Arg Gly Asp Asn Pro
1               5

<210> SEQ ID NO 29
<211> LENGTH: 7
<212> TYPE: PRT
<213> ORGANISM: Artificial Sequence
<220> FEATURE:
<223> OTHER INFORMATION: mutant linker

<400> SEQUENCE: 29

Lys Lys Lys Arg Thr Ile Cys
1               5

<210> SEQ ID NO 30
<211> LENGTH: 7
<212> TYPE: PRT
<213> ORGANISM: Artificial Sequence
<220> FEATURE:
<223> OTHER INFORMATION: mutant linker
```

```
<400> SEQUENCE: 30

Met Lys Lys Gly Thr Ile Cys
1               5

<210> SEQ ID NO 31
<211> LENGTH: 7
<212> TYPE: PRT
<213> ORGANISM: Artificial Sequence
<220> FEATURE:
<223> OTHER INFORMATION: mutant linker

<400> SEQUENCE: 31

Ile Glu Glu Gly Thr Ile Cys
1               5

<210> SEQ ID NO 32
<211> LENGTH: 7
<212> TYPE: PRT
<213> ORGANISM: Artificial Sequence
<220> FEATURE:
<223> OTHER INFORMATION: mutant linker

<400> SEQUENCE: 32

Lys Gly Ala Gly Lys Ile Cys
1               5

<210> SEQ ID NO 33
<211> LENGTH: 7
<212> TYPE: PRT
<213> ORGANISM: Artificial Sequence
<220> FEATURE:
<223> OTHER INFORMATION: mutant linker

<400> SEQUENCE: 33

Leu Lys Glu Gly Thr Ile Cys
1               5

<210> SEQ ID NO 34
<211> LENGTH: 7
<212> TYPE: PRT
<213> ORGANISM: Artificial Sequence
<220> FEATURE:
<223> OTHER INFORMATION: mutant linker

<400> SEQUENCE: 34

Ala Lys Lys Arg Thr Ile Cys
1               5

<210> SEQ ID NO 35
<211> LENGTH: 7
<212> TYPE: PRT
<213> ORGANISM: Artificial Sequence
<220> FEATURE:
<223> OTHER INFORMATION: mutant linker

<400> SEQUENCE: 35

Lys Ala Lys Arg Thr Ile Cys
1               5

<210> SEQ ID NO 36
<211> LENGTH: 7
<212> TYPE: PRT
<213> ORGANISM: Artificial Sequence
<220> FEATURE:
<223> OTHER INFORMATION: mutant linker
```

```
<400> SEQUENCE: 36

Lys Lys Ala Arg Thr Ile Cys
1               5

<210> SEQ ID NO 37
<211> LENGTH: 7
<212> TYPE: PRT
<213> ORGANISM: Artificial Sequence
<220> FEATURE:
<223> OTHER INFORMATION: mutant linker

<400> SEQUENCE: 37

Lys Lys Lys Ala Thr Ile Cys
1               5

<210> SEQ ID NO 38
<211> LENGTH: 7
<212> TYPE: PRT
<213> ORGANISM: Artificial Sequence
<220> FEATURE:
<223> OTHER INFORMATION: mutant linker

<400> SEQUENCE: 38

Lys Lys Lys Arg Ala Ile Cys
1               5

<210> SEQ ID NO 39
<211> LENGTH: 7
<212> TYPE: PRT
<213> ORGANISM: Artificial Sequence
<220> FEATURE:
<223> OTHER INFORMATION: mutant linker

<400> SEQUENCE: 39

Lys Ala Lys Arg Ala Ile Cys
1               5

<210> SEQ ID NO 40
<211> LENGTH: 7
<212> TYPE: PRT
<213> ORGANISM: Artificial Sequence
<220> FEATURE:
<223> OTHER INFORMATION: mutant linker

<400> SEQUENCE: 40

Ser Lys Ala Gly Thr Ile Cys
1               5

<210> SEQ ID NO 41
<211> LENGTH: 7
<212> TYPE: PRT
<213> ORGANISM: Artificial Sequence
<220> FEATURE:
<223> OTHER INFORMATION: mutant linker

<400> SEQUENCE: 41

Lys Lys Lys Arg Thr Ile Cys
1               5

<210> SEQ ID NO 42
<211> LENGTH: 6
<212> TYPE: PRT
<213> ORGANISM: Artificial Sequence
<220> FEATURE:
<223> OTHER INFORMATION: mutant C-terminus

<400> SEQUENCE: 42
```

```
Pro Arg Trp Asn Asp Leu
1               5

<210> SEQ ID NO 43
<211> LENGTH: 7
<212> TYPE: PRT
<213> ORGANISM: Artificial Sequence
<220> FEATURE:
<223> OTHER INFORMATION: mutant C-terminus

<400> SEQUENCE: 43

Pro Arg Asn Gly Leu Tyr Gly
1               5

<210> SEQ ID NO 44
<211> LENGTH: 5
<212> TYPE: PRT
<213> ORGANISM: Artificial Sequence
<220> FEATURE:
<223> OTHER INFORMATION: mutant C-terminus

<400> SEQUENCE: 44

Pro Gly Leu Tyr Gly
1               5

<210> SEQ ID NO 45
<211> LENGTH: 5
<212> TYPE: PRT
<213> ORGANISM: Artificial Sequence
<220> FEATURE:
<223> OTHER INFORMATION: mutant C-terminus

<400> SEQUENCE: 45

Pro Asp Leu Tyr Gly
1               5

<210> SEQ ID NO 46
<211> LENGTH: 5
<212> TYPE: PRT
<213> ORGANISM: Artificial Sequence
<220> FEATURE:
<223> OTHER INFORMATION: mutant C-terminus

<400> SEQUENCE: 46

Pro Pro Leu Tyr Gly
1               5

<210> SEQ ID NO 47
<211> LENGTH: 5
<212> TYPE: PRT
<213> ORGANISM: Artificial Sequence
<220> FEATURE:
<223> OTHER INFORMATION: mutant C-terminus

<400> SEQUENCE: 47

Pro Arg Leu Tyr Gly
1               5

<210> SEQ ID NO 48
<211> LENGTH: 5
<212> TYPE: PRT
<213> ORGANISM: Artificial Sequence
<220> FEATURE:
<223> OTHER INFORMATION: mutant C-terminus

<400> SEQUENCE: 48
```

Pro Glu Leu Tyr Gly
1               5

<210> SEQ ID NO 49
<211> LENGTH: 5
<212> TYPE: PRT
<213> ORGANISM: Artificial Sequence
<220> FEATURE:
<223> OTHER INFORMATION: mutant C-terminus

<400> SEQUENCE: 49

Pro Tyr Leu Tyr Gly
1               5

<210> SEQ ID NO 50
<211> LENGTH: 5
<212> TYPE: PRT
<213> ORGANISM: Artificial Sequence
<220> FEATURE:
<223> OTHER INFORMATION: Mutant

<400> SEQUENCE: 50

Ser Arg Ala Gly Lys
1               5

<210> SEQ ID NO 51
<211> LENGTH: 5
<212> TYPE: PRT
<213> ORGANISM: Artificial Sequence
<220> FEATURE:
<223> OTHER INFORMATION: Mutant

<400> SEQUENCE: 51

Lys Lys Lys Arg Thr
1               5

<210> SEQ ID NO 52
<211> LENGTH: 5
<212> TYPE: PRT
<213> ORGANISM: Artificial Sequence
<220> FEATURE:
<223> OTHER INFORMATION: Mutant

<400> SEQUENCE: 52

Lys Lys Ala Arg Thr
1               5

<210> SEQ ID NO 53
<211> LENGTH: 5
<212> TYPE: PRT
<213> ORGANISM: Artificial Sequence
<220> FEATURE:
<223> OTHER INFORMATION: Mutant

<400> SEQUENCE: 53

Met Lys Lys Gly Thr
1               5

<210> SEQ ID NO 54
<211> LENGTH: 5
<212> TYPE: PRT
<213> ORGANISM: Artificial Sequence
<220> FEATURE:
<223> OTHER INFORMATION: Mutant

<400> SEQUENCE: 54

Ile Glu Glu Gly Thr

```
1               5

<210> SEQ ID NO 55
<211> LENGTH: 5
<212> TYPE: PRT
<213> ORGANISM: Artificial Sequence
<220> FEATURE:
<223> OTHER INFORMATION: Mutant

<400> SEQUENCE: 55

Leu Lys Glu Gly Thr
1               5

<210> SEQ ID NO 56
<211> LENGTH: 5
<212> TYPE: PRT
<213> ORGANISM: Artificial Sequence
<220> FEATURE:
<223> OTHER INFORMATION: Mutant

<400> SEQUENCE: 56

Ala Lys Lys Arg Thr
1               5

<210> SEQ ID NO 57
<211> LENGTH: 5
<212> TYPE: PRT
<213> ORGANISM: Artificial Sequence
<220> FEATURE:
<223> OTHER INFORMATION: Mutant

<400> SEQUENCE: 57

Lys Ala Lys Arg Thr
1               5

<210> SEQ ID NO 58
<211> LENGTH: 5
<212> TYPE: PRT
<213> ORGANISM: Artificial Sequence
<220> FEATURE:
<223> OTHER INFORMATION: Mutant

<400> SEQUENCE: 58

Lys Lys Ala Arg Thr
1               5

<210> SEQ ID NO 59
<211> LENGTH: 5
<212> TYPE: PRT
<213> ORGANISM: Artificial Sequence
<220> FEATURE:
<223> OTHER INFORMATION: Mutant

<400> SEQUENCE: 59

Lys Lys Lys Ala Thr
1               5

<210> SEQ ID NO 60
<211> LENGTH: 5
<212> TYPE: PRT
<213> ORGANISM: Artificial Sequence
<220> FEATURE:
<223> OTHER INFORMATION: Mutant

<400> SEQUENCE: 60

Lys Lys Lys Arg Ala
1               5
```

```
<210> SEQ ID NO 61
<211> LENGTH: 5
<212> TYPE: PRT
<213> ORGANISM: Artificial Sequence
<220> FEATURE:
<223> OTHER INFORMATION: Mutant

<400> SEQUENCE: 61

Lys Ala Lys Arg Ala
1               5

<210> SEQ ID NO 62
<211> LENGTH: 5
<212> TYPE: PRT
<213> ORGANISM: Artificial Sequence
<220> FEATURE:
<223> OTHER INFORMATION: Mutant

<400> SEQUENCE: 62

Ser Lys Ala Gly Thr
1               5

<210> SEQ ID NO 63
<211> LENGTH: 3
<212> TYPE: PRT
<213> ORGANISM: Artificial Sequence
<220> FEATURE:
<223> OTHER INFORMATION: Mutant

<400> SEQUENCE: 63

Arg Tyr His
1

<210> SEQ ID NO 64
<211> LENGTH: 4
<212> TYPE: PRT
<213> ORGANISM: Artificial Sequence
<220> FEATURE:
<223> OTHER INFORMATION: Mutant

<400> SEQUENCE: 64

Arg Asn Gly Leu
1

<210> SEQ ID NO 65
<211> LENGTH: 5
<212> TYPE: PRT
<213> ORGANISM: Artificial Sequence
<220> FEATURE:
<223> OTHER INFORMATION: Mutant

<400> SEQUENCE: 65

Arg Gly Leu Tyr Gly
1               5

<210> SEQ ID NO 66
<211> LENGTH: 4
<212> TYPE: PRT
<213> ORGANISM: Artificial Sequence
<220> FEATURE:
<223> OTHER INFORMATION: Mutant

<400> SEQUENCE: 66

Arg Gly Leu Tyr
1
```

```
<210> SEQ ID NO 67
<211> LENGTH: 5
<212> TYPE: PRT
<213> ORGANISM: Artificial Sequence
<220> FEATURE:
<223> OTHER INFORMATION: Mutant

<400> SEQUENCE: 67

Arg Asp Leu Tyr Gly
1               5

<210> SEQ ID NO 68
<211> LENGTH: 4
<212> TYPE: PRT
<213> ORGANISM: Artificial Sequence
<220> FEATURE:
<223> OTHER INFORMATION: Mutant

<400> SEQUENCE: 68

Arg Asp Leu Tyr
1

<210> SEQ ID NO 69
<211> LENGTH: 6
<212> TYPE: PRT
<213> ORGANISM: Artificial Sequence
<220> FEATURE:
<223> OTHER INFORMATION: Mutant

<400> SEQUENCE: 69

Arg Asn Gly Leu Tyr Gly
1               5

<210> SEQ ID NO 70
<211> LENGTH: 6
<212> TYPE: PRT
<213> ORGANISM: Artificial Sequence
<220> FEATURE:
<223> OTHER INFORMATION: Mutant

<400> SEQUENCE: 70

Arg Asn Pro Trp Asn Gly
1               5
```

VEGFR FUSION PROTEIN PHARMACEUTICAL COMPOSITION

FIELD OF INVENTION

The present invention relates to a fusion protein pharmaceutical composition that inhibits angiogenic factor-activated pathways. In particular, the present invention relates to fusion proteins that inhibit angiogenic factor-activated pathways, the compositions of these fusion proteins, as well as methods for producing and using the same.

REFERENCE TO SEQUENCE LISTING SUBMITTED ELECTRONICALLY

This application contains a sequence listing, which is submitted electronically via EFS-Web as an ASCII formatted sequence listing with a file name "SequenceListing 7US1" and a creation date of Apr. 12, 2022, and having a size of 45.0 kb. The sequence listing submitted via EFS-Web is part of the specification and is herein incorporated by reference in its entirety.

BACKGROUND

Angiogenesis is the process of growing new blood vessels from the existing vasculature. It plays an important role in several physiological processes, including embryonic development, as well as tissue and wound repair (Folkman J et al. Angiogenic Factors. Science 1987; 235:442-7). The physiologic steps of angiogenesis are well characterized, and involve proteolysis of the extracellular matrix, proliferation, adhesion, migration, and assembly of the endothelial cells into a tubular channel, mural cell, pericyte recruitment and differentiation, and extracellular matrix production (Carmeliet P et al. Nature. 2011; 473:298-307). Pathologic angiogenesis may occur in tumor formation, ocular disorders (e.g., diabetic retinopathy, diabetic macular edema, retinal/choroidal neovascularization, exudative age-related macular degeneration, and neovascular glaucoma), arthritis, psoriasis, fibrotic diseases, inflammatory diseases, atherosclerosis, and arteriosclerosis (Polverini P J. Crit Rev Oral Biol Med. 1995; 6(3):230-47, Perrotta P et al. Vascular Pharmacology. 2019; 112:72-78).

Pathologic angiogenesis is more heterogeneous and chaotic, often demonstrating tortuous vessel organization, hypoxic voids of various sizes, uneven and imperfect vessel walls and linings, and ineffective perfusion (Jain R K., Nat Med. 2003; 9(6):685-93). These distinct characteristics of new blood vessel formation in diseases have made therapeutic targeting of angiogenesis a challenge. Although anti-VEGF therapies such as LUCENTIS® (ranibizumab), EYLEA® (aflibercept), or off-label use of AVASTIN® (bevacizumab) can generally stabilize or improve visual function, sub-retinal scarring (fibrosis) can develop in approximately half of all treated eyes within two years after anti-VEGF treatment and has been identified as one cause of unsuccessful outcomes (Daniel E et al. Ophthalmology. 2014; 121(3):656-66). Many of the critical players in sub-retinal fibrosis are likely to be the growth factors and the matricellular proteins that are involved in the fibrotic process (cell proliferation, migration and ECM remodeling) (Patsenker E et al. Hepatology. 2009 November; 50(5): 1501-1511, Xu J et al. Biochim Biophys Acta. 2014 November; 1842(11): 2106-2119). Despite its complexity, with our increasing knowledge of the angiogenic process, anti-angiogenic drug development remains an area of great interest.

Currently, many key players in the neovascularization process have been identified, and the vascular endothelial growth factor (VEGF) family has a predominant role. The human VEGF family consists of 6 members: VEGF-A, VEGF-B, VEGF-C, VEGF-D, VEGF-E, and placental growth factor (PlGF). In addition, multiple isoforms of VEGF-A, VEGF-B, and PlGF are generated through alternative RNA splicing (Sullivan et al. MAbs. 2002; 2(2): 165-75). VEGF-A is the primary factor involved with angiogenesis; it binds to both VEGFR-1 and VEGFR-2. The strategy of inhibiting angiogenesis by obstructing VEGF-A signaling has established successful therapies for treatment of specific cancers as well as retinal neovascular and ischemic diseases. (Major et al. J Pharmacol Exp Ther. 1997; 283(1):402-10; Willet et al. Nat. Med. 2004; 10:145-7; Papadopoulos et al. Angiogenesis. 2012; 15(2):171-85; Aiello et al. PNAS. 1995; 92:10457-61).

Other growth factors, cytokines, chemokines including Platelet Derived Growth Factors (PDGFs), Transforming Growth Factors beta (TGF-β), Epidermal Growth Factors (EGFs), Nerve Growth Factors (NGFs), Hypoxia-Induced Factor (HIF), basic Fibroblast Growth Factor or Fibroblast Growth Factor (bFGF or FGF-2), Connective-Tissue Growth Factor (CTGF), Granulocyte—Macrophage Colony-Stimulating Factor (GM-CSF), Insulin-Like Growth Factor (IGF), Hepatocyte Growth Factors/Scatter Factor (HGF/SF), Tumor Necrosis Factor alpha (TNF-α), stromal cell-derived factor-1 (SDF-1), Interleukin 1 (IL-1), Interleukin 6 (IL-6), Interleukin 8 (IL-8), Interleukin 17 (IL-17), Interleukin 18 (IL-18), Interleukin 20 (IL-20), Interleukin 23 (IL-23), Chemoattractants such as C-C motif Ligand (CCL28, CCL21) and C-X-C motif Ligand (CXCL1, CXCL5), Macrophage migration Inhibitory Factor (MIF), and immune cell surface proteins such as Clusters of Differentiation (CDs). These factors are reported to be overexpressed and play key roles in angiogenesis-related diseases (Elshabrawy et al. Angiogenesis. 2015; 18:433-448; Somanath P R et al, Cell Biochem Biophys. 2009; 53(2): 53-64, Eliceiri B P., Circ Res. 2001 Dec. 7; 89(12):1104-10). Targeting these factors to reduce their downstream pathway activation may decrease angiogenesis-related diseases.

Integrins, a family of cell surface receptors, are also found to be overexpressed on the endothelial cell surface and are believed to facilitate the growth and survival of newly forming vessels during angiogenesis. Integrins are heterodimeric cell surface receptors that interact with extracellular matrix proteins and are critical for many biological processes. The expression of integrins in various cell types are involved in tumor progression, and their ability to crosstalk with growth factor receptors and directly interact with several growth factors has made them attractive therapeutic targets. (Staunton D E et al. Adv Immunol. 2006; 91:111-57; Avraamides, C J et al. Nat Rev Cancer. 2008; 8:604-617, Somanath P R et al. Cell Biochem Biophys. 2009; 53(2): 53-64) In particular, the integrin αvβ3 is upregulated in both tumor cells and angiogenic endothelial cells, and is important for tumor cell migration, angiogenesis/neovascularization, and dysregulated cell signaling. Therefore, antagonists of the integrin αvβ3 are intensively studied for their anti-angiogenic and anti-tumor properties (Desgrosellier J S et al. Nat Rev Cancer. 2010; 10:9-22).

Disintegrins are proteins found in snake venom of the viper family and mainly inhibit the function of β1- and β3-associated integrins. They were first identified as inhibitors of integrin αIIbβ3 and were subsequently shown to bind with high affinity to other integrins, blocking the interaction of integrins with RGD-containing proteins. They contain 47 to 84 amino acids with about 4 to 7 disulfide bonds and carry the same RGD motif (McLane M A, et al. Proc Soc Exp Biol Med. 1998; 219: 109-119; Niewiarowski S et al. Semin Hematol 1994; 31: 289-300; Calvete J J, Curr Pharm Des. 2005; 11: 829-835; Blobel C P et al. Curr Opin Cell Biol. 1992; 4: 760-765). The conserved RGD sequence in the disintegrin family plays the most important role in recognizing the integrins. Disintegrins were found to interact with eight out of twenty-four integrins and inhibit integrin-mediated cell proliferation, adhesion, migration, and angiogenesis (McLane M A, et al. Front Biosci. 2008; 13: 6617-6637; Swenson S, et al. Curr Pharm Des. 2007; 13: 2860-2871). Animal studies showed that disintegrins targeted neovascular endothelium and metastatic tumors, indicating their potential use in cancer therapy. The specific binding of RGD-containing proteins to integrin is a function of both the conformation and the local sequence surrounding the RGD motif. Many studies have shown that the residues flanking the RGD motif of RGD-containing proteins affect their binding specificities and affinities to integrins (Scarborough R M et al. J Biol Chem. 1993; 268: 1058-1065; Rahman S et al. Biochem J. 1998; 335: 247-257).

Angiogenesis is a complex biological process which involves various growth factors and signaling receptors and targeting single molecules in the signaling cascade may not provide an effective clinical treatment for uncontrolled angiogenesis in diseases such as cancer. Therefore, there is a growing need to develop innovative therapeutics capable of binding several key angiogenic factors in a cooperative manner to effectively inhibit angiogenesis and progression of the disease.

BRIEF SUMMARY

Provided herein are pharmaceutical formulations of fusion proteins and methods of using such formulations.

In one general aspect, the application relates to a pharmaceutical formulation, the formulation comprising:
  a) a fusion protein in a concentration of about 0.5 mg/mL to about 120 mg/mL,
  b) a polyol or alcohol selected from a group consisting of sucrose, trehalose, mannitol, sorbitol, benzyl alcohol, polyvinyl alcohol, polyethylene glycol (PEG) 400-12000, in a concentration of about 1% to about 10% w/v,
  c) a buffering agent selected from a group consisting of sodium phosphate, histidine, sodium citrate, sodium acetate, sodium bicarbonate, and trisodium citrate dihydrate in a concentration of about 10 mM to about 50 mM, and
  d) a surfactant in a concentration of about 0.01 to about 4% w/v,
wherein the formulation is at a pH of about 5.5-7.5 and optionally, the formulation further comprises a polysaccharide selected from the group consisting of sodium carboxymethylcellulose, microcrystalline cellulose, or sodium hyaluronate.

According to embodiments of the application, the surfactant is selected from a group consisting of polysorbate 20, polysorbate 80 and poloxamer 188, preferably polysorbate 20.

According to embodiments of the application, the surfactant is in a concentration of about 0.03%.

According to embodiments of the application, the fusion protein is in a concentration of about 1 mg/mL to about 90 mg/mL, preferably about 20 mg/mL to about 80 mg/mL, more preferably the fusion protein is in a concentration of about 40 mg/mL.

According to embodiments of the application, the polyol is trehalose in a concentration of about 25 mM to about 250 mM, preferably about 190 mM.

According to embodiments of the application, the buffering agent is histidine in a concentration of about 10 mM to about 40 mM, preferably about 20 mM to about 30 mM, more preferably the histidine is in a concentration of about 25 mM.

According to embodiments of the application, the fusion protein comprises, from N-terminus to C-terminus in the following order:
  a) an extracellular domain of a Vascular Endothelial Growth Factor receptor (VEGFR);
  b) an Fc domain of human immunoglobulin G; and
  c) an integrin binding protein or its fragment thereof.

According to embodiments of the application, the fusion protein comprises SEQ ID NO:15, SEQ ID NO:16, SEQ ID NO: 17, or SEQ ID NO: 18.

According to embodiments of the application, the pH is about 5.5 to about 7.0, preferably the pH is about 6.0.

According to embodiments of the application, the formulation is stable at −70° C., −20° C. and/or 5° C. for at least 24 months.

According to embodiments of the application, the formulation retains protein purity and potency after least 9 months at −70° C., −20° C. and/or 2-8° C., preferably at 2-8° C.

According to embodiments of the application, the formulation further comprises a salt in a concentration of about 10 mM to 50 mM.

According to embodiments of the application, the formulation further comprises at least one amino acid in a concentration of about 10 mM to 50 mM.

According to embodiments of the application, the salt is selected from sodium chloride, magnesium chloride, calcium chloride, or potassium chloride.

According to embodiments of the application, the amino acid is selected from the group consisting of arginine, methionine, proline, histidine, cysteine, lysine, glycine, aspartate, tryptophan, glutamate, and isoleucine.

According to embodiments of the application, the pharmaceutical formulation can be used in a method of treating an ocular disease.

According to embodiments of the application, the ocular disease is selected from neovascularization or ischemia uveitis, retinal vasculitis, angioid streaks, retinitis pigmentosa, corneal neovascularization, iris neovascularization, neovascularization glaucoma, post-surgical fibrosis in glaucoma, proliferative vitreoretinopathy (PVR), choroidal neovascularization (CNV), optic disc neovascularization, retinal neovascularization, vitreal neovascularization, pannus, pterygium, vascular retinopathy, diabetic retinopathy (DR, non-proliferative and proliferative DR) without DME, diabetic retinopathy (DR, non-proliferative and proliferative DR) with DME, diabetic macular edema (DME), exudative (wet) and non-exudative (dry) age-related macular degeneration (AMD), macular edema, macular edema following retinal vein occlusion (RVO), retinal vein occlusion (RVO), central retinal vein occlusion (CRVO), Branch retinal vein occlusion (BRVO), Retinal Angiomatous Proliferation (RAP), polypoidal choroidal vascularization (PCV), vitreomacular adhesion (VMA) and/or vitreomacular traction (VMT).

According to embodiments of the application, the formulation is administered at a dose of about 0.03-10 mg per eye, preferably about 3.0-6.0 mg per eye, more preferably the formulation is administered at a dose of about 4 mg per eye.

According to embodiments of the application, the formulation is administered at a dose of about 4 mg per eye.

Another general aspect of the application relates to a pharmaceutical formulation, the formulation comprising:
 a) a fusion protein in a concentration of 40 mg/mL,
 b) 25 mM histidine,
 c) 190 mM trehalose, sucrose, or mannitol,
 d) 0.03% polysorbate 20 or polysorbate 80,
wherein the formulation is at a pH of about 6.0.

The specification is considered to be sufficient to enable one skilled in the art to practice the invention. Various modifications of the invention in addition to those shown and described herein will become apparent to those skilled in the art from the foregoing description and fall within the scope of the appended claims. All publications, patents and patent applications cited herein are hereby incorporated by reference in their entirety for all purposes.

BRIEF DESCRIPTION OF THE DRAWINGS

The foregoing and other objects, aspects, features, and advantages of exemplary embodiments will become more apparent and may be better understood by referring to the following description taken in conjunction with the accompanying drawings.

(FIG. 5B) phosphate buffer pH 6.5; (FIG. 5C) histidine buffer pH 6.5; (FIG. 5D) histidine buffer pH 6.0; (FIG. 5E) citrate buffer pH 6.0; and (FIG. 5F) citrate buffer pH 5.5, respectively. The diffusion coefficients were determined by dynamic light scattering (DLS).

FIG. 6A depicts wavelength 660 nm and FIG. 6B depicts wavelength 320 nm. NaPi=Sodium phosphate, Cit=Citrate and His=Histidine.

FIGS. 7A and 7B include Fusion Protein 1 at 40 or 80 mg/mL incubated in citrate buffer at 4° C. or 40° C. for a period, beginning (lanes 2 and 3), 4 days (lanes 4 and 5), 7 days (lanes 6 and 7), and 14 days (lanes 8 and 9). FIGS. 7C and 7D include Fusion Protein 1 at 40 or 80 mg/mL incubated in histidine buffer at 4° C. or 40° C. for a period, beginning (lanes 2 and 3), 4 days (lanes 4 and 5), 7 days (lanes 6 and 7), and 14 days (lanes 8 and 9). FIG. 7E includes Fusion Protein 1 at 40 or 80 mg/mL incubated in histidine or citrate buffer at 4° C. or 40° C. on Day 28. NaPi=Sodium phosphate, Cit=Citrate and His=Histidine. For each sample well, 3 of protein was loaded.

FIGS. 8A and 8B include Fusion Protein 1 at 40 or 80 mg/mL incubated in citrate buffer at 4° C. or 40° C. for a period, beginning (lanes 2 and 3), 4 days (lanes 4 and 5), 7 days (lanes 6 and 7), and 14 days (lanes 8 and 9). FIGS. 8C and 8D include Fusion Protein 1 at 40 or 80 mg/mL incubated in histidine buffer at 4° C. or 40° C. for a period, beginning (lanes 2 and 3), 4 days (lanes 4 and 5), 7 days (lanes 6 and 7), and 14 days (lanes 8 and 9). FIG. 8E includes Fusion Protein 1 at 40 or 80 mg/mL incubated in histidine or citrate buffer at 4° C. or 40° C. on Day 28. NaPi=Sodium phosphate, Cit=Citrate and His=Histidine. For each sample well, 3 µg of protein was loaded.

DETAILED DESCRIPTION

Figure 1:
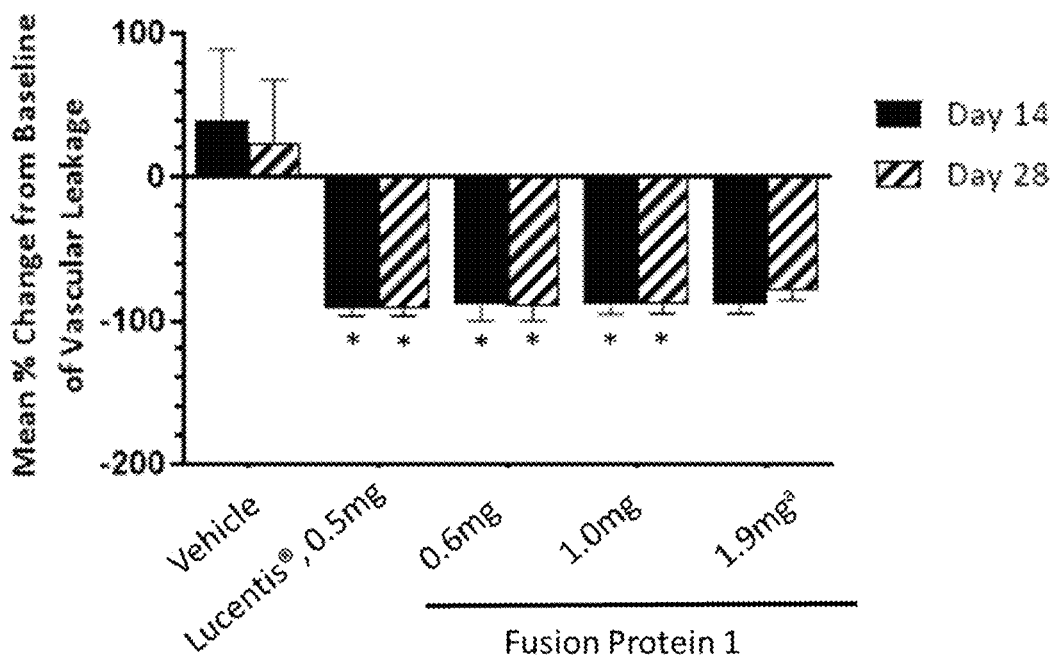
FIG. 1 is a graph of the mean percent change from baseline of the vascular leakage area following a single intravitreal injection of Fusion Protein 1 at 0.6, 1.0, and 1.9 mg/eye in a laser-induced choroidal neovascularization model in rhesus monkeys. Data presented as mean±SEM. All doses were administered as a single intravitreal dose on Day 0. Lucentis® (0.5 mg) was used as system suitability and positive control. All spots analyzed were of Grade III/IV. % Vascular Leakage=(Baseline leakage area−Treatment leakage area)÷(Baseline leakage area)×100%; Statistical analysis was conducted to compare treatment group with vehicle group by Mann-Whitney U test, *, p<0.05. $^a$In the 1.9 mg group, data from one monkey with severe ocular inflammation was removed which affected statistical significance (p=0.057). n=4 eyes per group.

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a binding domain" includes a plurality of binding domains and equivalents thereof known to those skilled in the art.

As used herein, the term "polypeptide" and "protein" may be used interchangeably to refer to a long chain of peptide having an amino acid sequence of the native protein or the amino acid sequence with one or more mutations such as deletions, additions, and/or substitutions of one or more amino acid residues.

A "fusion protein" refers to a protein having two or more portions covalently linked together, where each of the portions is derived from different proteins.

The present invention provides a pharmaceutical formulation comprising a fusion protein comprising an integrin binding peptide selected from a group consisting of disintegrin (see U.S. Pat. No. 7,943,728 and PCT Application No. PCT/US15/46322 for the description of amino acid sequences, each of which is incorporated by reference in its entirety), anti-integrin αvβx antibody (see U.S. Pat. Nos. 6,160,099 and 8,350,010 for the description of amino acid sequences, each of which is incorporated by reference in its entirety), anti-integrin α5β1 antibody, fibronectin (see U.S. Pub. No. 2015/0218251 for the description of amino acid sequences, which is incorporated by reference in its entirety) targeting integrin isoform αvβx or α5β1 and their integrin binding fragments, other protein binding peptide targeting an angiogenic factor and a Fc domain, wherein x is 1, 3, 5, 6 or 8.

The term "antibody", as used herein, is intended to refer to immunoglobulin molecules comprised of four polypeptide chains, two heavy chains and two light chains interconnected by disulfide bonds. A full-length heavy chain includes a variable region domain, VH, and three constant region domains, CH1, CH2 and CH3. The VH domain is at the amino-terminus of the polypeptide, and the CH3 domain is at the carboxy-terminus. A full-length light chain includes a variable region domain, VL, and a constant region domain, CL. An antigen binding fragment (Fab) is comprised of one light chain and the CH1 and variable regions of one heavy chain. The heavy chain of a Fab molecule cannot form a disulfide bond with another heavy chain molecule. A Fab' fragment contains one light chain and one heavy chain that contains more of the constant region, between the CH1 and CH2 domains, such that an interchain disulfide bond can be formed between two heavy chains to form diabodies. A variable fragment (Fv) region comprises the variable regions from both the heavy and light chains but lacks the constant regions. Single-chain fragments (scFv) are Fv molecules in which the heavy and light chain variable regions have been connected by a flexible linker to form a single polypeptide chain which forms an antigen-binding region. Single chain antibodies are discussed in detail in WO88/01649 and U.S. Pat. Nos. 4,946,778 and 5,260,203. As used herein, the term "antibody" includes an immunoglobulin molecule with two full length L-chains and two full length H-chains, and fragments thereof, such as an antigen binding fragment (Fab), a Fv region, a scFv, etc.

The term "Fc domain" refers to a molecule or sequence comprising the sequence of a non-antigen binding portion of an antibody, whether in monomeric or multimeric form. The original immunoglobulin source of an Fc is preferably of human origin and can be from any isotype, e.g., IgG, IgA, IgM, IgE or IgD. A full-length Fc consists of the following Ig heavy chain regions: the flexible hinge region between CH1 and CH2, CH2 and CH3, wherein the two chains are typically connected by disulfide bonds in the flexible hinge region.

The present invention provides a fusion protein comprising an integrin binding peptide that includes disintegrin and its integrin binding fragments, other protein binding peptide comprising an extracellular domain of VEGF receptor and a Fc domain, wherein the integrin binding peptide comprises at least one mutation on or adjacent to the RGD motif. In accordance with embodiments of the present invention, the disintegrin and its integrin binding fragments have an amino acid sequence selected from a group consisting of SEQ ID NO: 1, SEQ ID NO: 2, SEQ ID NO: 3, SEQ ID NO: 4, SEQ ID NO: 5, SEQ ID NO: 6, and SEQ ID NO: 7, or amino acid sequence having at least 85% sequence identity to SEQ ID NO: 1, SEQ ID NO: 2, SEQ ID NO: 3, SEQ ID NO: 4, SEQ ID NO: 5, SEQ ID NO: 6, and SEQ ID NO: 7.

As used herein, "disintegrin" refers to a class of cysteine-rich proteins or polypeptides that are potent soluble ligands of integrins. The RGD motif is a tri-peptide (Arg-Gly-Asp) conserved in most monomeric disintegrins and is located at an integrin-binding loop. The disintegrins described herein are isolated from snake venom or derived from wild-type forms and have at least one mutation on or adjacent to a RGD motif to selectively bind to or target to various integrin isoforms. The term "adjacent to a RGD motif" as used herein means any mutation which occurs at any amino acid residue within 15-20 amino acids from the RGD motif in a given peptide, polypeptide, protein sequence.

Other amino acid sequence variants of the disintegrin are also contemplated. For example, binding affinity and/or other biological properties of a disintegrin can be improved by altering the amino acid sequence encoding the protein. Disintegrin mutants can be prepared by introducing appropriate modifications into the nucleic acid sequence encoding the protein or by introducing modification by peptide synthesis. Such modifications include mutations such as deletions from, insertions into, and/or substitutions within the nucleic or amino acid sequence of the disintegrin. Any combination of deletion, insertion, and substitution can be made to arrive at the final amino acid construct of the disintegrin provided that the final construct possesses the desired characteristics such as binding to an integrin superfamily member and/or inhibiting the integrin activated pathway.

Substantial modifications in the biological properties of the proteins or polypeptides are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

A useful method for identifying certain residues or regions of the fusion protein that are preferred locations for mutagenesis is known as "alanine scanning mutagenesis" as described in Cunningham B C et al. Science. 1989; 244: 1081-1085. For example, a residue or group of target residues are identified (e.g., charged residues such as Arg, Asp, His, Lys and Glu) and replaced by a neutral (most preferably glycine, alanine or leucine) or oppositely charged amino acid (from positive charge to negative charge or vice versa) to affect the interaction of the amino acids with the target binding partner. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, random mutagenesis may be conducted at the target codon or region and the expressed fusion polypeptide variants are screened for desired activity. For example, cysteine bond(s) may be added to the fusion protein or protein components to improve its stability.

Accordingly, provided herein are disintegrin mutants that can be a component of any fusion protein disclosed herein. In some embodiments, the disintegrin comprises an amino acid sequence with at least 85%, at least 90%, at least 95%, or at least 99% sequence identity to the amino acid sequence of disintegrins selected from a group consisting of Rhodostomin (SEQ ID NO: 1), Triflavin (SEQ ID NO: 3), Echistatin (SEQ ID NO: 4), Trimucrin (SEQ ID NO: 5), Elegantin (SEQ ID NO: 6) and Trigramin (SEQ ID NO: 7). In some embodiments, a disintegrin comprises an amino acid sequence having at least one mutation on or adjacent to the RGD motif of Rhodostomin (SEQ ID NO: 1), Triflavin (SEQ ID NO: 3), Echistatin (SEQ ID NO: 4), Trimucrin (SEQ ID NO: 5), Elegantin (SEQ ID NO: 6) or Trigramin (SEQ ID NO: 7). In some embodiments, the disintegrin comprises an amino acid sequence with at least 85%, at least 90%, at least 95%, or at least 99% sequence identity to the amino acid sequence of a disintegrin mutant (SEQ ID NO: 2). The Xaa in SEQ ID NO: 2 indicates various positions that can be modified by either insertion, substitution or deletion to produce amino acid sequence variants that are different from the wild type form of disintegrin. According to some examples, the Xaa at position 50 of SEQ ID NO: 2 which corresponds to glycine (Gly) in the RGD motif of wild type Rhodostomin (SEQ ID NO: 1) may be substituted with naturally occurring amino acids other than glycine to generate Rhodostomin mutants. In other examples, one or more Xaa in SEQ ID NO: 2 may also be substituted with naturally occurring amino acids other than those originally found in corresponding positions of wild type Rhodostomin (SEQ ID NO: 1) to generate various Rhodostomin mutants. It is further noted that the disintegrin mutants are not limited to include only single mutation at any Xaa in SEQ ID NO: 2, multiple mutations that occur at several locations of Xaa in SEQ ID NO: 2 or corresponding locations in other consensus sequences of disintegrin (such as SEQ ID NOs: 3-7) may also be encompassed by the scope of the invention.

Rhodostomin mutants have been described in U.S. Pat. No. 7,943,728 and PCT Application No. PCT/US15/46322 and their sequences are incorporated herein by reference. For example, PCT/US15/46322 describes the disintegrin variant comprised of a mutant RGD loop having the amino acid sequence selected from the group consisting of SEQ ID NO: 24 to SEQ ID NO: 26, and at least one of a mutant linker having the amino acid sequence selected from the group consisting of SEQ ID NO: 29 to SEQ ID NO: 41, and a mutant C-terminus having the amino acid sequence selected from the group consisting of SEQ ID NO: 42 to SEQ ID NO: 47. More preferably, the disintegrin variant comprises the mutant RGD loop, the mutant linker and the mutant C-terminus described herein.

Mutants of Rhodostomin or disintegrins with one or more modifications in addition to the RGD motif, e.g., in the linker region or the C-terminus, exhibited the capability to selectively bind to αvβ3, αvβ5, αvβ6, α5β1 or αIIbβ3. For example, Rhodostomin variants with the mutation in the linker region (39X40X41X42X43X), in which the SRAGK (SEQ ID NO: 50) was replaced by KKKRT (SEQ ID NO: 51), KKART (SEQ ID NO: 52), MKKGT (SEQ ID NO: 53) IEEGT (SEQ ID NO: 54), LKEGT (SEQ ID NO: 55), AKKRT (SEQ ID NO: 56), KAKRT (SEQ ID NO: 57), KKART (SEQ ID NO: 58), KKKAT (SEQ ID NO: 59), KKKRA (SEQ ID NO: 60), KAKRA (SEQ ID NO: 61), or SKAGT (SEQ ID NO: 62) amino acids, had their highest effects on integrins in the following order: αIIbβ33 (~2-fold)>α5β1 (~5-fold)>αvβ3 (~14-fold).

Rhodostomin variants with the mutation in the C-terminal region (66X67X68X69X70X), in which the RYH was replaced by RYH (SEQ ID NO: 63), RNGL (SEQ ID NO: 64), RGLYG (SEQ ID NO: 65), RGLY (SEQ ID NO: 66), RDLYG (SEQ ID NO: 67), RDLY (SEQ ID NO: 68), RNGLYG (SEQ ID NO: 69), or RNPWNG (SEQ ID NO: 70) amino acids, had their highest effects on integrins in the following order: αIIbβ3 (~13-fold)>αvβ5 (~8-fold)=αvβ6 (~8-fold)>αvβ3 (~4-fold)>α5β1 (~2-fold). Table 1 shows the sequences of SEQ ID NOs: 24 to 49 and their corresponding positions on SEQ ID NO: 1.

TABLE 1

| SEQ ID NO | Sequence | Position on SEQ ID NO: 1 |
|---|---|---|
| 24 | RIARGDNP | 46-53 |
| 25 | RRARGDNP | |
| 26 | ARGRGDNP | |
| 27 | ARGRGDDL | |
| 28 | ARARGDNP | |
| 29 | KKKRTIC | 39-45 |
| 30 | MKKGTIC | |
| 31 | IEEGTIC | |
| 32 | KGAGKIC | |
| 33 | LKEGTIC | |
| 34 | AKKRTIC | |
| 35 | KAKRTIC | |
| 36 | KKARTIC | |
| 37 | KKKATIC | |
| 38 | KKKRAIC | |
| 39 | KAKRAIC | |
| 40 | SKAGTIC | |
| 41 | KKKRTIC | |
| 42 | PRWNDL | 65-68 |
| 43 | PRNGLYG | |
| 44 | PGLYG | |
| 45 | PDLYG | |
| 46 | PPLYG | |
| 47 | PRLYG | |
| 48 | PELYG | |
| 49 | PYLYG | |

Although the variants of disintegrins are discussed mostly with reference to the amino acid sequences discussed above, polypeptide sequences or nucleotide sequence encoding the snake venom such as Albolabrin, Applagin, Basilicin, Batroxostatin, Bitistatin, Cereberin, Cerastin, Crotatroxin, Durissin, Flavoridin, Flavostatin, Halysin, Halystatin, Jararacin, Jarastatin, Kistrin, Lachesin, Lutosin, Molossin, Salmosin, Saxatilin, Tergeminin, Trimestatin, Trimutase, Ussuristatin, Viridian and their mutants having at least one mutation on or adjacent to the RGD motif may also be encompassed by the scope of the present invention.

Without being bound by theory, it is contemplated herein that disintegrins inhibit the integrin activated pathway by binding to an integrin superfamily member to block its interaction with a multivalent integrin receptor. In some aspects, the disintegrin binds to an integrin superfamily member which includes but is not limited to the integrin isoforms αvβ1, αvβ3, αvβ5, αvβ6, αvβ8, α5β1 and/or αIIbβ3.

According to the present invention, the other protein binding peptide of the fusion protein may be receptor protein that binds to a target selected from the group consisting of a tumor antigen, a TNF receptor superfamily member, a Hedgehog family member, a receptor tyrosine kinase, a proteoglycan-related molecule, a TGF-beta superfamily member, a Wnt-related molecule and an angiogenesis target.

According to some embodiments of the invention, the other protein binding peptide may specifically bind to an angiogenesis target which includes but is not limited to Angiopoietin (ANG), Ephrin (Eph), Fibroblast Growth Factor (FGF), Neuropilin (NRP), Plasminogen Activators, Platelet-Derived Growth Factor (PDGF), Tumor Growth factor beta (TGF-β), Vascular Endothelial Growth Factor (VEGF), Vascular Endothelial cadherin (VE-cadherin), Tumor necrosis factor-alpha (TNF-α), Insulin like growth factor (IGF-1) and their receptors. Therefore, in accordance with embodiments of the invention, the other protein binding peptide may include extracellular portions of a receptor protein that binds to and antagonizes the angiogenesis target. In other embodiments, the other protein binding peptide may bind to extracellular portions of angiogenic factor receptors.

In some embodiments, the other protein binding peptide may be an anti-VEGF antibody (see WO2015/200905 for the description of its amino acid sequence, which is incorporated herein by reference in its entirety) that binds to the VEGF ligand or an anti-VEGFR1 or anti-VEGFR2 antibody (see U.S. Pat. No. 5,874,542 for the description of its amino acid sequence, which is incorporated herein by reference in its entirety) that binds to VEGF receptor. In other embodiments, the other protein binding peptide may also be an anti-PDGF antibody (see U.S. Pat. No. 5,094,941 for the description of its amino acid sequence, which is incorporated herein by reference in its entirety) that binds to the PDGF ligand or an anti-PDGFRβ antibody (see U.S. Pat. No. 9,265,827 for the description of its amino acid sequence, which is incorporated herein by reference in its entirety for all purposes) that binds to PDGF receptor.

In certain embodiments, the other protein binding peptide binds to the same VEGF as any one of VEGF receptors (VEGFR): VEGFR1, VEGFR2 and VEGFR3. In some embodiments, the other protein binding peptide comprises at least one extracellular portion of a VEGFR of any of the VEGFRs described herein. For example, the other protein binding peptide comprises at least one extracellular portion of VEGFR1 or one extracellular portion of VEGFR2. In another example, the other protein binding peptide comprises one extracellular portion of VEGFR1 such as Ig-like domain 2 (D2) and one extracellular portion of VEGFR2 such as Ig-like domain 3 (D3). In some aspect, the other protein binding peptide comprises one extracellular portion of a VEGFR1 comprising amino acid sequence of SEQ ID NO: 8 and one extracellular portion of a VEGFR2 comprising amino acid sequence of SEQ ID NO: 9. In some aspect, the other protein binding peptide comprises a fusion of extracellular portions of VEGFR1 and VEGFR2 comprising an amino acid sequence of SEQ ID NO: 10 or an amino acid sequence with at least 85% sequence identity to SEQ ID NO: 10.

In other embodiments, the other protein binding peptide binds to the same PDGF as any one of PDGF receptors (PDGFR): PDGFRα and PDGFRβ. In some embodiments, the other protein binding peptide comprises at least one extracellular portion of a PDGFR of any of the PDGFRs described herein. For example, the other protein binding peptide comprises at least one extracellular portion of PDGFRα or one extracellular portion of PDGFRβ. In another example, the other protein binding peptide comprises one extracellular portion of PDGFRβ such as Ig-like domain 1-3. In some aspect, the other protein binding peptide comprises an extracellular portion of a PDGFR comprising an amino acid sequence of SEQ ID NO: 11 or an amino acid sequence with at least 85% sequence identity to SEQ ID NO: 11.

In accordance with other embodiments, the invention also provides a fusion protein comprising an integrin binding peptide that includes an amino acid sequence of SEQ ID NO:1 with at least one mutation on or adjacent to the RGD motif, an amino acid sequence having at least 85% sequence identity to SEQ ID NO: 1 or an amino acid sequence of SEQ ID NO: 2, a human or humanized constant sub-region comprising an immunoglobulin CH2 domain and a CH3 domain, and other protein binding peptide having an Ig-like D2 of a VEGFR1 and an Ig-like D3 of a VEGFR2. In a further embodiment of the fusion protein, the integrin binding peptide has at least 85% sequence identity to SEQ ID NO: 2.

The term "percent (%) sequence identity" with respect to a reference polypeptide or nucleic acid sequence is defined as the percentage of amino acid residues or nucleotides in a candidate sequence that are identical with the amino acid residues or nucleotides in the reference polypeptide or nucleic acid sequence, after aligning the sequences and introducing gaps, if necessary, to achieve the maximum percent sequence identity, and not considering any conservative substitutions as part of the sequence identity. Alignment for purposes of determining percent amino acid or nucleic acid sequence identity can be achieved in various ways that are within the skill in the art, for instance, using publicly available computer software programs, for example, as those described in Current Protocols in Molecular Biology (Ausubel et al. eds., 1987), and including BLAST, BLAST-2, ALIGN or Megalign (DNASTAR) Software. Those skilled in the art can determine appropriate parameters for measuring alignment, including any algorithms needed to achieve maximal alignment over the full length of the sequences being compared. For purposes herein, the % amino acid sequence identity of a given amino acid sequence A to, with or against a given amino acid sequence B is calculated as follows: 100 times the fraction X/Y, where X is the number of amino acid residues score as identical matches by the sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

The present invention provides a dimeric fusion protein comprising two fusion proteins, wherein each fusion protein comprises any fusion protein disclosed herein. In one embodiment, the dimeric fusion protein comprises two identical fusion proteins. In another embodiment, the dimeric fusion protein may comprise two different fusion proteins. The fusion proteins disclosed herein may form multimers of two or more identical fusion proteins or form heterologous fusion proteins through a multimerization domain which includes a constant sub-region of a human or humanized antibody. In some embodiments, the constant sub-region of a human or humanized antibody is selected from the group consisting of an IgG Fc region, IgA Fc region, IgM Fc region, IgD Fc region and IgE Fc region. In the further embodiment, the constant sub-region of a human or humanized antibody is selected from the group consisting of an IgG1 Fc region, IgG2 Fc region, IgG3 Fc region and IgG4 Fc region. In some aspect, the sub-region comprises a CH2 region and a CH3 region of IgG1, IgG2, IgG3, or IgG4.

Amino acid sequences encoding immunoglobulins that comprise Fc regions are well known in the art.

The components of the fusion protein may be connected directly to each other or be connected via linkers. Generally, the term "linker" means one or more molecules e.g., nucleic acids, amino acids or non-peptide moieties which may be inserted between one or more component domains. For example, linkers may be used to provide a desirable site of interest between components for ease of manipulation. A linker may also be provided to enhance expression of the fusion protein from a host cell, to decrease steric hindrance such that the component may assume its optimal tertiary structure and/or interact appropriately with its target molecule. A linker sequence may include one or more amino acids naturally connected to a receptor component or may be an added sequence used to enhance expression of the fusion protein, to provide specifically desired sites of interest, to allow component domains to form optimal tertiary structures and/or to enhance the interaction of a component with its target molecule.

Preferably, the linker increases flexibility of the fusion protein components without interfering with the structure of each functional component within the fusion protein. In some embodiments, the linker moiety is a peptide linker with a length of 2 to 100 amino acids. Exemplary linkers include linear peptides having at least two amino acid residues such as Gly-Gly, Gly-Ala-Gly, Gly-Pro-Ala, Gly(G)n and Gly-Ser (GS) linker. The GS linker described herein includes but is not limited to (GS)n, (GSGSG)n, $(G_2S)n$, $G_2S_2G$, $(G_2SG)n$, $(G_3S)n$, $(G_4S)n$, $(GGGGG)nGn$ and $GSG_4SG_4SG$, wherein n is 1 or more. One example of the (G)n linker includes a $G_9$ linker. Suitable linear peptides include polyglycine, polyserine, polyproline, polyalanine and oligopeptides consisting of alanyl and/or serinyl and/or prolinyl and/or glycyl amino acid residues. The linker moieties may be used to link any of the components of the fusion proteins disclosed herein. In some embodiments, a linker is used between an extracellular portion of a receptor protein and a constant sub-region of an immunoglobulin. In other embodiments, a linker is used between disintegrin or its variant and a constant sub-region of an immunoglobulin. In certain embodiments, the fusion protein comprises a linker between an extracellular portion of a receptor protein and disintegrin or its variant, and a linker between disintegrin or its variant and a constant sub-region of an immunoglobulin. As embodied in the present invention, a fusion protein may comprise at least one linker but no more than four linkers.

The fusion protein described herein may or may not comprise a signal peptide that functions for secreting the fusion protein from a host cell. A nucleic acid sequence encoding the signal peptide can be operably linked to a nucleic acid sequence encoding the protein of interest. In some embodiments, the fusion protein comprises a signal peptide. In some embodiment, the fusion protein does not comprise a signal peptide.

Moreover, the fusion proteins described in the present invention may comprise modified forms of the protein binding peptides. For example, the fusion protein components may have post-translational modifications, including for example, glycosylation, sialylation, acetylation, and phosphorylation to any of the protein binding peptides.

Although the embodiments are generally described with reference to two protein binding peptides included in the fusion protein, the invention also contemplates a fusion protein which incorporates more than two protein binding peptides to provide any additional or synergistic effects in terms of inhibiting the process of angiogenesis. For example, there may be an additional protein binding peptide that binds to other angiogenesis targets or acts as angiogenic factor antagonists to be linked to the existing two protein binding peptides.

Fusion proteins for the pharmaceutical formulations disclosed herein may be purified and identified using commonly known methods such as fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; hydrophobic affinity resins, ligand affinity using a suitable binding partner immobilized on a matrix, centrifugation, Enzyme-Linked Immunosorbent Assay (ELISA), BIACore, Western Blot assay, amino acid and nucleic acid sequencing, and biological activity. In some embodiments, the fusion protein is expressed in host cells and purified therefrom using a combination of one or more standard purification techniques, including, but not limited to Protein A affinity chromatography, Protein G affinity chromatography, buffer exchange, size exclusion chromatography, ultrafiltration, and dialysis. Accordingly, the recovered fusion protein is substantially pure. In a further embodiment, the recovered fusion protein is at least any of 90%, 95%, 96%, 97%, 98% or 99% pure.

The fusion proteins or fusion protein components disclosed herein may be characterized or assessed for biological activities including, but not limited to, affinity to a target binding partner, competitive binding, inhibitory activity, inhibition of cell proliferation, inhibition of tumor growth, and inhibition of angiogenesis. In some embodiments, the fusion proteins or fusion protein components disclosed herein can be assessed for biological activity in vitro and in vivo. Many methods for assessing binding affinity are known in the art and can be used to identify the binding affinities of fusion proteins or fusion protein components to a binding partner through a titration method. Binding kinetics can be expressed as the steady-state equilibrium binding constant, expressed as the dissociation constant ($K_D$) or half maximal effective concentration ($EC_{50}$) values.

In certain embodiments, a fusion protein has an $EC_{50}$ of less than or equal to 1 µM, 100 nM, 10 nM, 1 nM, 0.1 nM, 0.01 nM, or 0.001 nM for inhibition of an activity (e.g., inhibition of angiogenic factor activity and/or integrin activity). In any of the embodiments herein, a fusion protein has a $K_D$ for a binding partner (angiogenic factor and/or integrin) of less than about 1.0 mM, 500 µM, 100 µM, 50 µM, 10 µM, 5 µM, 1 µM, 500 nM, 100 nM, 50 nM, 10 nM, 5 nM, 1 nM, 500 pM, 100 pM, 50 pM, 10 pM or 5 pM, including any values in between these numbers.

In certain embodiments, the isoelectric point (pI) of the fusion protein is about 4.0 to 9.0. In certain embodiments, the isoelectric point (pI) of the fusion protein is about 4.0, 4.1, 4.2, 4.3, 4.4, 4.5, 4.6, 4.7, 4.7, 4.8, 4.9, 5.0, 5.1, 5.2, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 9.3, 8.4, 8.5, 8.6, 8.7, 8.8, 8.9, 9.0, or any value in between. Preferably, the isoelectric point (pI) of the fusion protein is 8.17.

The invention also provides a pharmaceutical composition comprising a fusion protein comprising an integrin binding peptide selected from a group consisting of disintegrin, anti-integrin αvβx antibody, anti-integrin α5β1 antibody, fibronectin targeting integrin αvβx or α5β1 and their integrin binding fragments, other protein binding peptide targeting an angiogenic factor and a Fc domain, wherein x is 1, 3, 5, 6 or 8. Compositions of the invention comprise a therapeutically effective amount of the fusion protein.

The term "therapeutically effective amount" means an amount of a therapeutically active compound needed to elicit the desired biological or clinical effect. According to embodiments of the invention, "a therapeutically effective amount" is an amount sufficient to effect beneficial or desired results, including clinical results. A therapeutically effective amount can be administered in one or more administrations. In terms of a disease state, a therapeutically effective amount is an amount sufficient to ameliorate, stabilize, or delay development of a disease. According to specific embodiments of the invention, a therapeutically effective amount is an amount of a fusion protein needed to treat or prevent a disorder characterized by abnormal angiogenesis, such as a disease characterized by neovascularization, vascular permeability, edema, inflammation, retinopathies, fibrosis or cancer.

The term "potency" means the ability of the fusion protein to function as intended at the clinical dose administered.

The term "pharmaceutical formulation" herein refers to formulations including pharmaceutically acceptable carriers, e.g., used to administer VEGF receptor fusion proteins (e.g., aflibercept or conbercept) to a subject for a therapeutic/medicinal use.

The term "purity" herein refers to the absence of contamination of the fusion protein. Contaminants as referred to herein include protein species other than the intended fusion protein molecule, arising from the compound manufacturing process as impurities and/or degradation of the manufactured protein compound.

In some embodiments, the pharmaceutical composition comprising a fusion protein comprises a fusion protein formulated in a buffer at a protein concentration from about 0.5 to about 100 mg/mL, preferably about 40 to about 80 mg/mL, such as about 40, 50, 60, 70 or 80 mg/mL, most preferably about 40±about 4 mg/mL. In other preferred embodiments, the fusion protein is formulated in a buffer at a protein concentration of more than about 40 mg/mL.

In particular embodiments, the buffer is a buffer with a pH of about 5.5 to 7.0, more preferably about 6.0 to 6.5, even more preferably about 6.0. In particular embodiments, the buffer is a phosphate buffer with a pH of about 6.5 to 8, more preferably about 7 to 7.5, even more preferably about 7.2. The phosphate buffer comprises about 5 to 20 mM sodium phosphate, such as 5, 10, 15 or 20 mM sodium phosphate, more preferably about 10 mM sodium phosphate; about 20 to 60 mM sodium chloride, more preferably about 40 mM sodium chloride; about 1 to 10% weight-per-volume (w/v) sucrose, more preferably about 5% w/v sucrose; and about 0.01 to 0.05% w/v of a surfactant, more preferably about 0.03% w/v polysorbate 20.

In particular embodiments, the pharmaceutical formulation comprises a polyol or alcohol selected from a group consisting of sucrose, trehalose, mannitol, sorbitol, benzyl alcohol, polyvinyl alcohol, polyethylene glycol (PEG) 400-12000, in a concentration of about 1% to about 10% w/v such as about 1%, 2%, 3%, 4%, 5%, 6%, 7%, 8%, 9%, or 10% w/v.

In preferred embodiments, the polyol is trehalose in a concentration of about 25 mM to about 250 mM, such as about 25 mM, 50 mM, 75 mM, 100 mM, 125 mM, 150 mM, 175 mM, 200 mM, 225 mM, or 250 mM. In other preferred embodiments, the polyol is trehalose in a concentration of about 100 to 200 mM such as about 100 mM, 110 mM, 120 mM, 130 mM, 140 mM, 150 mM, 160 mM, 170 mM, 180 mM, 190 mM, or 200 mM. In other preferred embodiments, the polyol is trehalose in a concentration of about 190 mM.

In particular embodiments, the pharmaceutical formulation comprises a buffering agent. In particular embodiments, the buffering agent is selected from a group consisting of sodium phosphate, histidine, sodium citrate, sodium acetate, sodium bicarbonate, and trisodium citrate dihydrate in a concentration of about 10 mM to about 50 mM such as about 10 mM, 20 mM, 30 mM, 40 mM, or 50 mM. In preferred embodiments, the buffering agent is in a concentration of about 10 mM to about 40 mM such as about 10 mM, 20 mM, 30 mM, or 40 mM. In other preferred embodiments, the buffering agent is in a concentration of about 20 mM to 30 mM such as about 20 mM, 21 mM, 22 mM, 23 mM, 24 mM, 25 mM, 26 mM, 27 mM, 28 mM, 29 mM, or 30 mM. In other preferred embodiments, the buffering agent is in a concertation of about 25 mM.

In particular embodiments, the pharmaceutical formulation further comprises a polysaccharide selected from the group consisting of sodium carboxymethylcellulose, microcrystalline cellulose, or sodium hyaluronate.

In preferred embodiments, the buffering agent is histidine in a concentration of about 10 mM to about 40 mM such as about 10 mM, 20 mM, 30 mM, or 40 mM. In other preferred embodiments, the histidine is in a concentration of about 20 mM to about 30 mM such as about 20 mM, 21 mM, 22 mM, 23 mM, 24 mM, 25 mM, 26 mM, 27 mM, 28 mM, 29 mM, or 30 mM. In other preferred embodiments, the histidine is in a concentration of about 25 mM.

In particular embodiments, the pharmaceutical formulation comprises a surfactant. In preferred embodiments, the surfactant is in a concentration of about 0.01 to about 4% w/v such as about 0.01%, 0.5%, 1.0%, 1.5%, 2.0%, 2.5%, 3.0%, 3.5%, or 4.0%. In other preferred embodiments, the surfactant is in a concentration of about 0.01% to about 1.0% w/v such as about 0.01%, 0.02%, 0.03%, 0.04%, 0.05%, 0.06%, 0.07%, 0.08%, 0.09%, 1.0% w/v. In other preferred embodiments the surfactant is in a concentration of about 0.03% w/v.

In preferred embodiments, the surfactant is selected from a group consisting of polysorbate 20, polysorbate 80 and poloxamer 188, preferably polysorbate 20. In preferred embodiments, polysorbate 20 is in a concentration of about 0.03% w/v.

In some embodiments, the fusion protein is in a pharmaceutical formulation that is stable at −70° C. to 5° C. for at least two years such as −70° C., −60° C., −50° C., −40° C., −30° C., −20° C., −10° C., 0° C., or 5° C. In some embodiments, the fusion protein is in a pharmaceutical formulation that is stable at −70° C., −20° C., and/or 5° C. for at least 6 months such as 6 months, 7 months, 8 months, 9 months, 10 months, 11 months, or more. In preferred embodiments, the fusion protein is in a pharmaceutical formulation that is stable at −70° C., −20° C., and/or 5° C. for at least one year, two years, three years, four years, five years, six years, seven years, eight years, nine years, or ten years or more. In other preferred embodiments, the fusion protein is in a pharmaceutical formulation that is stable at −70° C.-20° C., and/or 5° C. for at least two years.

In some embodiments, the formulation retains protein purity and potency after at least 6 months at −70° C. to 25° C. such as −70° C., −60° C., −50° C., −40° C., −30° C., −20° C., −10° C., 0° C., or 5° C. or 25° C. In some embodiments, the formulation retains protein purity and potency after at least 6 months at −70° C., −20° C., and/or 5° C. such as 6 months, 7 months, 8 months, 9 months, 10 months, 11 months, one year, two years, three years, four years, five years, six years, seven years, eight years, nine years, or ten years or more.

In some embodiments, the formulation further comprises a salt. In some embodiments, the salt is selected from sodium chloride, magnesium chloride, calcium chloride, or potassium chloride.

In particular embodiments, the formulation further comprises at least one amino acid. In some embodiments, the amino acid is selected from the group consisting of arginine, histidine, methionine, proline, cysteine, lysine, glycine, aspartate, tryptophan, glutamate, and isoleucine.

In some embodiments, the pharmaceutical formulation comprises a fusion protein in a concentration of 40 mg/mL, 25 mM histidine, 190 mM trehalose, and 0.03% polysorbate 20, wherein the formulation is at a pH of about 6.0.

The present invention also provides a method for making any formulation set forth herein comprising the step of combining each component of the formulation into a single composition. Such a method may include the step of adding the resulting formulation into a vial or injection device. The method may additionally include a sterile filtration step. Any composition that is the product of such a method also forms part of the present invention. For example, embodiments herein also include methods for preparing a formulation by combining a histidine-based buffer with a surfactant (such as polysorbate 20), a fusion protein, trehalose, and optionally, one or more additional components, e.g., as discussed herein.

The present invention also relates to a use of the composition according to the present invention to treat or prevent an integrin-associated disease in an individual or a subject. An "individual" or "subject" is a mammal. Mammals include, but are not limited to, domesticated animals (e.g., cows, sheep, cats, dogs, and horses), primates (e.g., humans and non-human primates such as monkeys), rabbits and rodents (e.g., mice and rats). In some embodiments, a method of treating or preventing one or more aspects or symptoms of a disease comprises administering an effective amount of a composition comprising the fusion protein to an individual.

The methods described herein can be used for the treatment of a variety of diseases, including but not limited to, inflammatory disease, ocular disease, autoimmune disease, or cancer. In some embodiments, the disease to be treated includes, but is not limited to, rheumatoid arthritis, inflammatory arthritis, osteoarthritis, cancer, tissue/organ fibrosis, retinitis pigmentosa, uveitis (such as anterior uveitis or posterior uveitis) and ocular disease characterized by neovascularization or ischemia (such as corneal neovascularization, iris neovascularization, neovascularization glaucoma, post-surgical fibrosis in glaucoma, proliferative vitreoretinopathy (PVR), choroidal neovascularization (CNV), optic disc neovascularization, retinal neovascularization, vitreal neovascularization, pannus, pterygium, vascular retinopathy, diabetic retinopathy (DR, non-proliferative and proliferative DR) without DME, diabetic retinopathy (DR, non-proliferative and proliferative DR) with DME, diabetic macular edema (DME), exudative (wet) and non-exudative (dry) age-related macular degeneration (AMD), macular edema, macular edema following retinal vein occlusion (RVO), retinal vein occlusion (RVO), central retinal vein occlusion (CRVO), Branch retinal vein occlusion (BRVO), Retinal Angiomatous Proliferation (RAP), polypoidal choroidal vascularization (PCV)), vitreomacular adhesion (VMA) and/or vitreomacular traction (VMT).

The compositions described herein can be administered to an individual via any route, including, but not limited to, intravenous, intraperitoneal, ocular, intra-arterial, intrapulmonary, oral, inhalation, intravesicular, intramuscular, intratracheal, subcutaneous, intrathecal, transdermal, transpleural, topical, mucosal, gastrointestinal, intraarticular, intracisternal, intraventricular, intracranial, intraurethral, intrahepatic and intratumoral. In some embodiments, the compositions are administered systemically (for example by intravenous injection). In some embodiments, the compositions are administered locally (for example by intraarterial or intraocular related injection thereof).

In some embodiments, the compositions are administered directly to the eye or the eye tissue. In some embodiments, the compositions are administered topically to the eye, for example, in eye drops. In some embodiments, the compositions are administered by injection to the eye or to the tissues associated with the eye. The compositions can be administered, for example, by intraocular injection, periocular injection, subretinal injection, intravitreal injection, suprachoroidal injection, trans-septal injection, subscleral injection, intrachoroidal injection, intracameral injection, subconjunctival injection, sub-Tenon's injection, retrobulbar injection, peribulbar injection, or posterior juxtascleral delivery. These methods are known in the art. The compositions may be administered, for example, to the vitreous, aqueous humor, sclera, conjunctiva, the area between the sclera and conjunctiva, the retina choroids tissues, macula, or other area in or proximate to the eye of an individual.

In some embodiments, the pharmaceutical composition is administered to the eye at a dose of about 0.03-10 mg per eye, such as 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, or 10 mg. In preferred embodiments, the pharmaceutical composition is delivered to the eye at a dose of about 3.0-6.0 mg per eye such as 3.0 mg, 3.5 mg, 4.0 mg, 4.5 mg, 5.0 mg, 5.5 mg, or 6 mg. In other preferred embodiments, the pharmaceutical composition is delivered to the eye at a dose of about 4 mg per eye.

The optimal effective amount of the compositions can be determined empirically and will depend on the type and severity of the disease, route of administration, disease progression and health, mass and body area of the individual. Such determinations are within the skill of one in the art. Compositions comprising a fusion protein can also be administered six times a week, five times a week, four times a week, three times a week, twice a week, once a week, once every two weeks, once every three weeks, once a month, once every two months, once every three months, once every four months, once every six months, once every nine months, or once every year.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to describe the methods and/or materials in connection with which the publications are cited.

EMBODIMENTS

The application includes, but is not limited to, the following numbered embodiments:

Embodiment 1 is a pharmaceutical formulation, the formulation comprising:
- a) a fusion protein in a concentration of about 0.5 mg/mL to about 120 mg/mL,
- b) a polyol or alcohol selected from a group consisting of sucrose, trehalose, mannitol, sorbitol, benzyl alcohol, polyvinyl alcohol, polyethylene glycol (PEG) 400-12000, in a concentration of about 1% to about 10% w/v,
- c) a buffering agent selected from a group consisting of sodium phosphate, histidine, sodium citrate, sodium acetate, sodium bicarbonate, and trisodium citrate dihydrate in a concentration of about 10 mM to about 50 mM, and
- d) a surfactant in a concentration of about 0.01 to about 4% w/v, wherein the formulation is at a pH of about 5.5-7.5 and optionally, the formulation further comprises a polysaccharide selected from the group consisting of sodium carboxymethylcellulose, microcrystalline cellulose, or sodium hyaluronate.

Embodiment 2 is the pharmaceutical formulation of embodiment 1, wherein the surfactant is selected from a group consisting of polysorbate 20, polysorbate 80 and poloxamer 188, preferably polysorbate 20.

Embodiment 3 is the pharmaceutical formulation of embodiment 2, wherein the polysorbate is polysorbate 20.

Embodiment 4 is the pharmaceutical formulation of any one of embodiments 1-3, wherein the surfactant is in a concentration of about 0.03% w/v.

Embodiment 5 is the pharmaceutical formulation of any one of embodiments 1-4, wherein the fusion protein is in a concentration of about 1 mg/mL to about 90 mg/mL, preferably about 20 mg/mL to about 80 mg/mL, more preferably the fusion protein is in a concentration of about 40 mg/mL.

Embodiment 6 is the pharmaceutical formulation of embodiment 5, wherein the fusion protein is in a concentration of 40 mg/mL.

Embodiment 7 is the pharmaceutical formulation of any one of embodiments 1-6, wherein the polyol is trehalose in a concentration of about 25 mM to about 250 mM, preferably about 190 mM.

Embodiment 8 is the pharmaceutical formulation of embodiment 7, wherein trehalose is in a concentration of about 190 mM.

Embodiment 9 is the pharmaceutical formulation of any one of embodiments 1-8, wherein the buffering agent is histidine in a concentration of about 10 mM to about 40 mM, preferably about 20 mM to about 30 mM, more preferably the histidine is in a concentration of about 25 mM.

Embodiment 10 is the pharmaceutical formulation of embodiment 9, wherein the histidine is in a concentration of about 25 mM.

Embodiment 11 is the pharmaceutical formulation of any one of embodiments 1-10, wherein the fusion protein comprises, from N-terminus to C-terminus in the following order:
- a) an extracellular domain of a Vascular Endothelial Growth Factor receptor (VEGFR);
- b) an Fc domain of human immunoglobulin G; and
- c) an integrin binding protein or its fragment thereof.

Embodiment 12 is the pharmaceutical formulation of any one of embodiments 1-11, wherein the fusion protein comprises, SEQ ID NO:15, SEQ ID NO:16, SEQ ID NO: 17, or SEQ ID NO: 18.

Embodiment 13 is the pharmaceutical formulation of any one of embodiments 1-12, wherein the pH is about 5.5 to about 7.0, preferably the pH is about 6.0.

Embodiment 14 is the pharmaceutical formulation of embodiment 13, wherein the pH is about 6.0.

Embodiment 15 is the pharmaceutical formulation of any one of embodiments 1-14, wherein the formulation is stable at −70° C., −20° C. and/or 2-8° C. for at least 24 months.

Embodiment 16 is the pharmaceutical formulation of any one of embodiments 1-15, wherein the formulation retains protein purity and potency after least 6 months at −70° C., −20° C. and/or 2-8° C., preferably at 2-8° C.

Embodiment 17 is the pharmaceutical formulation of any one of embodiments 1-16, wherein the formulation further comprises a salt in a concentration of about 10 mM to 50 mM.

Embodiment 18 is the pharmaceutical formulation of embodiment 17, wherein the salt is selected from sodium chloride, magnesium chloride, calcium chloride, or potassium chloride.

Embodiment 19 is the pharmaceutical formulation of any one of embodiments 1-18, further comprises at least one amino acid in a concentration of about 10 mM to 50 mM.

Embodiment 20 is the pharmaceutical formulation of embodiment 19, wherein the amino acid is selected from the group consisting of arginine, methionine, proline, histidine, cysteine, lysine, glycine, aspartate, tryptophan, glutamate, and isoleucine.

Embodiment 21 is the pharmaceutical formulation of any one of embodiments 1-20, wherein the formulation is used for a method of treating an ocular disease.

Embodiment 22 is the pharmaceutical formulation of embodiment 21, wherein the ocular disease is selected from neovascularization or ischemia uveitis, retinal vasculitis, angioid streaks, retinitis pigmentosa, corneal neovascularization, iris neovascularization, neovascularization glaucoma, post-surgical fibrosis in glaucoma, proliferative vitreoretinopathy (PVR), choroidal neovascularization (CNV), optic disc neovascularization, retinal neovascularization, vitreal neovascularization, pannus, pterygium, vascular retinopathy, diabetic retinopathy (DR, non-proliferative and proliferative DR) without DME, diabetic retinopathy (DR, non-proliferative and proliferative DR) with DME, diabetic macular edema (DME), exudative (wet) and non-exudative (dry) age-related macular degeneration (AMD), macular edema, macular edema following retinal vein occlusion (RVO), retinal vein occlusion (RVO), central retinal vein occlusion (CRVO), Branch retinal vein occlusion (BRVO), Retinal Angiomatous Proliferation (RAP), polypoidal choroidal vascularization (PCV), vitreomacular adhesion (VMA) and/or vitreomacular traction (VMT).

Embodiment 23 is the pharmaceutical formulation of any one of embodiments 1-22, wherein the formulation is administered at a dose of about 0.03-10 mg per eye, preferably about 3.0-6.0 mg per eye, more preferably the formulation is administered at a dose of about 4 mg per eye.

Embodiment 24 is the pharmaceutical formulation of embodiment 23, wherein the formulation is administered at dose of about 4 mg per eye.

Embodiment 25 is a pharmaceutical formulation, the formulation comprising:
- a) a fusion protein in a concentration of 40 mg/mL,
- b) 25 mM histidine, c) 190 mM trehalose, sucrose, or mannitol,
d) 0.03% polysorbate 20, or polysorbate 80,
wherein the formulation is at a pH of about 6.0.

Embodiment 26 is the pharmaceutical formulation of embodiment 25, wherein the fusion protein comprises, from N-terminus to C-terminus in the following order:
  a) an extracellular domain of a Vascular Endothelial Growth Factor receptor (VEGFR);
  b) an Fc Domain of human immunoglobulin G;
  c) an integrin binding protein or its fragment thereof.

Embodiment 27 is the pharmaceutical formulation of embodiment 26, wherein the fusion protein comprises SEQ ID NO:15, SEQ ID NO:16, SEQ ID NO: 17, or SEQ ID NO: 18.

Embodiment 28 is the pharmaceutical formulation of any one of embodiments 25-27, wherein the formulation is stable at −70° C., −20° C. and/or 5° C. for at least 24 months.

Embodiment 29 is the pharmaceutical formulation of any one of embodiments 25-28, wherein the formulation retains protein purity and potency after at least 6 months at −70° C., −20° C. and/or 2-8° C., preferably at 2-8° C.

Embodiment 30 is the pharmaceutical formulation of any one of embodiments 25-29, wherein the formulation further comprises a salt in a concentration of about 10 mM to 50 mM.

Embodiment 31 is the pharmaceutical formulation of embodiment 30, wherein the salt is selected from sodium chloride, magnesium chloride, calcium chloride, or potassium chloride.

Embodiment 32 is the pharmaceutical formulation of any one of embodiments 25-31, wherein the formulation further comprises at least one amino acid in a concentration of about 10 mM to 50 mM.

Embodiment 33 is the pharmaceutical formulation of embodiment 32, wherein the amino acid is selected from the group consisting of arginine, methionine, proline, histidine, cysteine, lysine, glycine, aspartate, tryptophan, glutamate, and isoleucine.

Embodiment 34 is the pharmaceutical formulation of any one of embodiments 25-33, wherein the formulation is used for a method of treating an ocular disease.

Embodiment 35 is the pharmaceutical formulation of embodiment 34, wherein the ocular disease is selected from neovascularization or ischemia uveitis, retinal vasculitis, angioid streaks, retinitis pigmentosa, corneal neovascularization, iris neovascularization, neovascularization glaucoma, post-surgical fibrosis in glaucoma, proliferative vitreoretinopathy (PVR), choroidal neovascularization (CNV), optic disc neovascularization, retinal neovascularization, vitreal neovascularization, pannus, pterygium, vascular retinopathy, diabetic retinopathy (DR, non-proliferative and proliferative DR) without DME, diabetic retinopathy (DR, non-proliferative and proliferative DR) with DME, diabetic macular edema (DME), exudative (wet) and non-exudative (dry) age-related macular degeneration (AMD), macular edema, macular edema following retinal vein occlusion (RVO), retinal vein occlusion (RVO), central retinal vein occlusion (CRVO), Branch retinal vein occlusion (BRVO), Retinal Angiomatous Proliferation (RAP), polypoidal choroidal vascularization (PCV), vitreomacular adhesion (VMA) and/or vitreomacular traction (VMT).

Embodiment 36 is the pharmaceutical formulation of any one of embodiments 25-35, wherein the formulation is administered at a dose of about 0.03-10 mg per eye, preferably about 3.0-6.0 mg per eye, more preferably the formulation is administered at a dose of about 4 mg per eye.

Embodiment 37 is the pharmaceutical formulation of embodiment 36, wherein the formulation is administered at dose of about 4 mg per eye.

Embodiment 38 is a method of treating an ocular disease in a subject, the method comprising administering to the subject a pharmaceutical formulation comprising:
  a) a fusion protein in a concentration of about 0.5 mg/mL to about 120 mg/mL,
  b) a polyol or alcohol selected from a group consisting of such as sucrose, trehalose, mannitol, sorbitol, benzyl alcohol, polyvinyl alcohol, PEG 400-12000 in a concentration of about 1% to about 10% w/v,
  c) a buffering agent selected from a group consisting of sodium phosphate, histidine, sodium citrate, sodium acetate, sodium bicarbonate, and trisodium citrate dihydrate in a concentration of about 10 mM to about 50 mM,
  d) a surfactant in a concentration of about 0.01 to about 4% w/v,
wherein the pH is about 5.5-7.5 and optionally, the formulation further comprises a polysaccharide selected from the group consisting of sodium carboxymethylcellulose, microcrystalline cellulose, or sodium hyaluronate.

Embodiment 39 is the method of embodiment 38, wherein the surfactant is selected from a group consisting of polysorbate 20, polysorbate 80 and poloxamer 188, preferably polysorbate 20.

Embodiment 40 is the method of embodiment 39, wherein the surfactant is polysorbate 20.

Embodiment 41 is the method of any one of embodiments 38-40, wherein the surfactant is in a concentration of about 0.03% w/v.

Embodiment 42 is the method of any one of embodiments 38-41, wherein the fusion protein is in a concentration of about 1 mg/mL to about 90 mg/mL, preferably about 40 mg/mL to about 80 mg/mL, more preferably the fusion protein is a concentration of about 40 mg/mL.

Embodiment 43 is the method of embodiment 42, wherein the fusion protein is in a concentration of about 40 mg/mL.

Embodiment 44 is the method of any one of embodiments 38-43, wherein the polyol is trehalose in a concentration of about 150 mM to about 230 mM, preferably about 190 mM.

Embodiment 45 is the method of embodiment 44, wherein trehalose is in a concentration of about 190 mM.

Embodiment 46 is the method of any one of embodiments 38-45, wherein the buffer is histidine in a concentration of about 20 mM to about 40 mM, preferably about 20 mM to about 30 mM, more preferably the histidine is in a concentration of about 25 mM.

Embodiment 47 is the method of embodiment 46, wherein the histidine is in a concentration of about 25 mM.

Embodiment 48 is the method of any one of embodiments 38-47, wherein the fusion protein comprises, from N-terminus to C-terminus in the following order:
  a) an extracellular domain of a Vascular Endothelial Growth Factor receptor (VEGFR);
  b) an Fc domain of human immunoglobulin G; and
  c) an integrin binding protein or its fragment thereof.

Embodiment 49 is the method of any one of embodiments 38-48, wherein the fusion protein comprises SEQ ID NO:15, SEQ ID NO:16, SEQ ID NO: 17, or SEQ ID NO: 18.

Embodiment 50 is the method of any one of embodiments 38-49, wherein the pH is about 6.0 to about 6.5, preferably the pH is about 6.0.

Embodiment 51 is the method of embodiment 50, wherein the pH is about 6.0.

Embodiment 52 is the method of any one of embodiments 38-51, wherein the formulation is stable at −70° C., −20° C. and/or 2-8° C. for at least 24 months.

Embodiment 53 is the method of any one of embodiments 38-52, wherein the formulation retains protein purity and potency after at least 6 months at −70° C., −20° C. and/or 2-8° C., preferably at 2-8° C.

Embodiment 54 is the method of any one of embodiments 38-53, wherein formulation further comprises a salt in a concentration of about 10 mM to 50 mM.

Embodiment 55 is the method of embodiment 54, wherein the salt is selected from sodium chloride, magnesium chloride, calcium chloride, or potassium chloride.

Embodiment 56 is the method of any one of embodiments 38-55, wherein the formulation further comprises at least one amino acid in a concentration of about 10 mM to 50 mM.

Embodiment 57 is the method of embodiment 56, wherein the amino acid is selected from the group consisting of arginine, methionine, proline, histidine, cysteine, lysine, glycine, aspartate, tryptophan, glutamate, and isoleucine.

Embodiment 58 is the method of any one of embodiments 38-57, wherein the ocular disease comprises neovascularization or ischemia uveitis, retinal vasculitis, retinitis pigmentosa, angioid streaks, corneal neovascularization, iris neovascularization, neovascularization glaucoma, post-surgical fibrosis in glaucoma, proliferative vitreoretinopathy (PVR), choroidal neovascularization (CNV), optic disc neovascularization, retinal neovascularization, vitreal neovascularization, pannus, pterygium, vascular retinopathy, diabetic retinopathy (DR, non-proliferative and proliferative DR) without DME, diabetic retinopathy (DR, non-proliferative and proliferative DR) with DME, diabetic macular edema (DME), exudative (wet) and non-exudative (dry) age-related macular degeneration (AMD), macular edema, macular edema following retinal vein occlusion (RVO), retinal vein occlusion (RVO), central retinal vein occlusion (CRVO), Branch retinal vein occlusion (BRVO), Retinal Angiomatous Proliferation (RAP), polypoidal choroidal vascularization (PCV), vitreomacular adhesion (VMA) and/or vitreomacular traction (VMT).

Embodiment 59 is the method of any one of embodiments 38-58, wherein the formulation is administered at a dose of about 0.03-10 mg per eye, preferably about 3.0-6.0 mg per eye, more preferably the formulation is administered at a dose of about 4 mg per eye.

Embodiment 60 is the method of embodiment 59, wherein the formulation is administered at dose of about 4 mg per eye.

Embodiment 61 is a method of treating an ocular disease in a subject, the method comprising administering to the subject a pharmaceutical formulation comprising:
 a) a fusion protein in a concentration of 40 mg/mL,
 b) 25 mM histidine,
 c) 190 mM trehalose, sucrose, or mannitol,
 d) 0.03% polysorbate 20, or polysorbate 80,
wherein the formulation is at a pH of about 6.0.

Embodiment 62 is the method of embodiment 61, wherein the fusion protein comprises, from N-terminus to C-terminus in the following order:
 a) an extracellular domain of a Vascular Endothelial Growth Factor receptor (VEGFR);
 b) an Fc Domain of human immunoglobulin G;
 c) an integrin binding protein or its fragment thereof.

Embodiment 63 is the method of embodiment 62, wherein the fusion protein comprises SEQ ID NO:15, SEQ ID NO:16, SEQ ID NO: 17, or SEQ ID NO: 18.

Embodiment 64 is the method of any one of embodiments 61-63, wherein the formulation is stable at −70° C., −20° C. and/or 5° C. for at least 24 months.

Embodiment 65 is the method of any one of embodiments 61-64, wherein the formulation retains protein purity and potency after at least 6 months at −70° C., −20° C. and/or 2-8° C., preferably at 2-8° C.

Embodiment 66 is the method of any one of embodiments 61-65, wherein the formulation further comprises a salt in a concentration of about 10 mM to 50 mM.

Embodiment 67 is the method of embodiment 66, wherein the salt is selected from sodium chloride, magnesium chloride, calcium chloride, or potassium chloride.

Embodiment 68 is the method of any one of embodiments 61-67, wherein the formulation further comprises at least one amino acid in a concentration of about 10 mM to 50 mM.

Embodiment 69 is the method of embodiment 68, wherein the amino acid is selected from the group consisting of arginine, methionine, proline, histidine, cysteine, lysine, glycine, aspartate, tryptophan, glutamate, and isoleucine.

Embodiment 70 is the method of any one of embodiments 61-69, wherein the ocular disease is selected from neovascularization or ischemia uveitis, retinal vasculitis, angioid streaks, retinitis pigmentosa, corneal neovascularization, iris neovascularization, neovascularization glaucoma, post-surgical fibrosis in glaucoma, proliferative vitreoretinopathy (PVR), choroidal neovascularization (CNV), optic disc neovascularization, retinal neovascularization, vitreal neovascularization, pannus, pterygium, vascular retinopathy, diabetic retinopathy (DR, non-proliferative and proliferative DR) without DME, diabetic retinopathy (DR, non-proliferative and proliferative DR) with DME, diabetic macular edema (DME), exudative (wet) and non-exudative (dry) age-related macular degeneration (AMD), macular edema, macular edema following retinal vein occlusion (RVO), retinal vein occlusion (RVO), central retinal vein occlusion (CRVO), Branch retinal vein occlusion (BRVO), Retinal Angiomatous Proliferation (RAP), polypoidal choroidal vascularization (PCV), vitreomacular adhesion (VMA) and/or vitreomacular traction (VMT).

Embodiment 71 is the method of any one of embodiments 61-70, wherein the formulation is administered at a dose of about 0.03-10 mg per eye, preferably about 3.0-6.0 mg per eye, more preferably the formulation is administered at a dose of about 4 mg per eye.

Embodiment 72 is the method of embodiment 71, wherein the formulation is administered at dose of about 4 mg per eye.

EXAMPLES

The following examples are offered to illustrate but not to limit the invention. One of skill in the art will recognize that the following procedures may be modified using methods known to one of ordinary skill in the art.

Example 1. Evaluation of Fusion Protein 1 in a Laser-Induced Choroidal Neovascularization Model in Rhesus Monkeys Fusion Protein 1 (an IgG1 Fc-fusion protein with multiple targets) was evaluated in a monkey model of choroidal neovascularization (CNV) in the eyes.

In the CNV model, rhesus monkeys (n=4 eyes per group) received laser burns on the retina using photocoagulation, and choroidal neovascularization was allowed to develop for 21 days (Day −21 to Day 0). On Day 0, Vehicle, 0.5 mg/eye Lucentis® (0.5 mg/eye) or Fusion Protein 1 (0.6 mg, 1.0 mg, 1.9 mg/eye) were injected into the monkey eyes via a single intravitreal (IVT) injection. Efficacy endpoints were evaluated on baseline (Day −2) prior to dosing, and on Day 14 and Day 28 post-injection in all groups.

Figure 2:
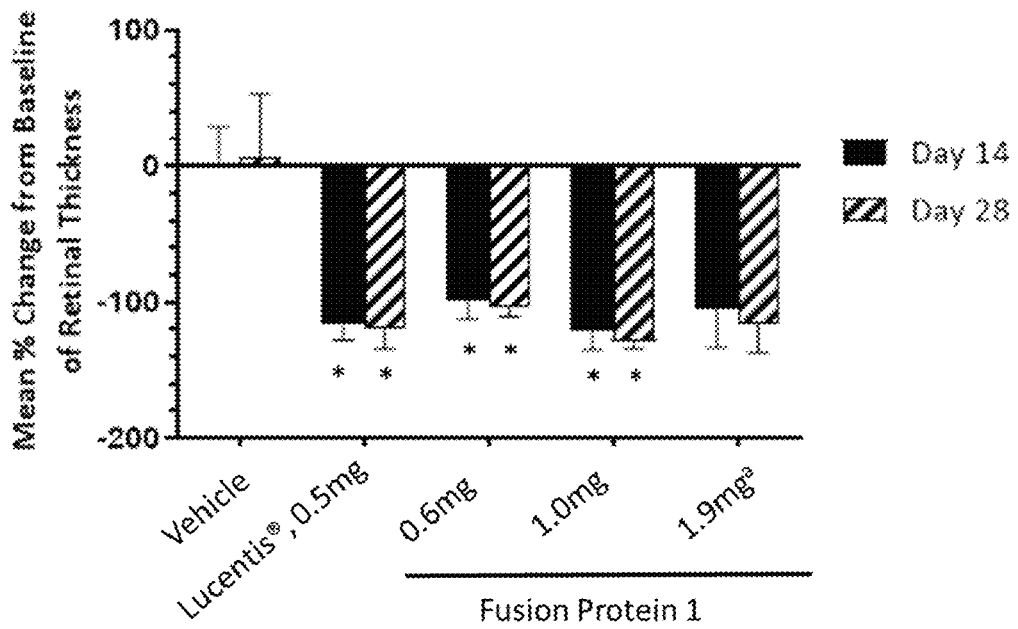
FIG. 2 is a graph of the mean retinal thickness assess by optical coherence tomography following a single intravitreal injection of Fusion protein 1 at 0.6, 1.0, and 1.9 mg/eye in a laser-induced choroidal neovascularization model in rhesus monkeys. Data presented as mean±SEM. All doses were administered as a single intravitreal dose on Day 0. Lucentis® (0.5 mg) was used as system suitability and positive control. All spots analyzed were of Grade III/IV. % Retinal thickness=(Baseline retinal thickness−Treatment retinal thickness)÷(Baseline retinal thickness−Pre-study retinal thickness)×100%; Statistical analysis was conducted to compare treatment group with vehicle group by Mann-Whitney U test, *, p<0.05. $^a$In the 1.9 mg group, data from one monkey with severe ocular inflammation was removed which affected statistical significance (p=0.057). n=4 eyes per group.

In the eyes treated with 0.5 mg Lucentis®, mean leakage area scores decreased by 91% and 92% on Day 14 and 28, respectively, compared to baseline (FIG. 1). Mean retinal thickness also decreased by 117% and 120%, respectively, compared to baseline (FIG. 2). Lucentis® showed statistically significant improvement compared to eyes treated with the vehicle control.

All three dose groups of Fusion Protein 1 exhibited recovery of the laser-induced retinal thickness, and leakage area compared to baseline and pre-study values. Mean leakage area scores decreased by 87% to 89 and 79% to 90% on Day 14 and 28, respectively (FIG. 1). Mean retinal thickness also decreased by 98% to 121% and 104% to 129%, respectively (FIG. 2). Fusion Protein 1 showed statistically significant improvement compared to eyes treated with the vehicle control on Day 14 and Day 28 for the 0.6 mg and 1.0 mg doses. There was no dose-dependent effect of Fusion Protein 1 observed, as all doses showed similar efficacy.

Figure 3:
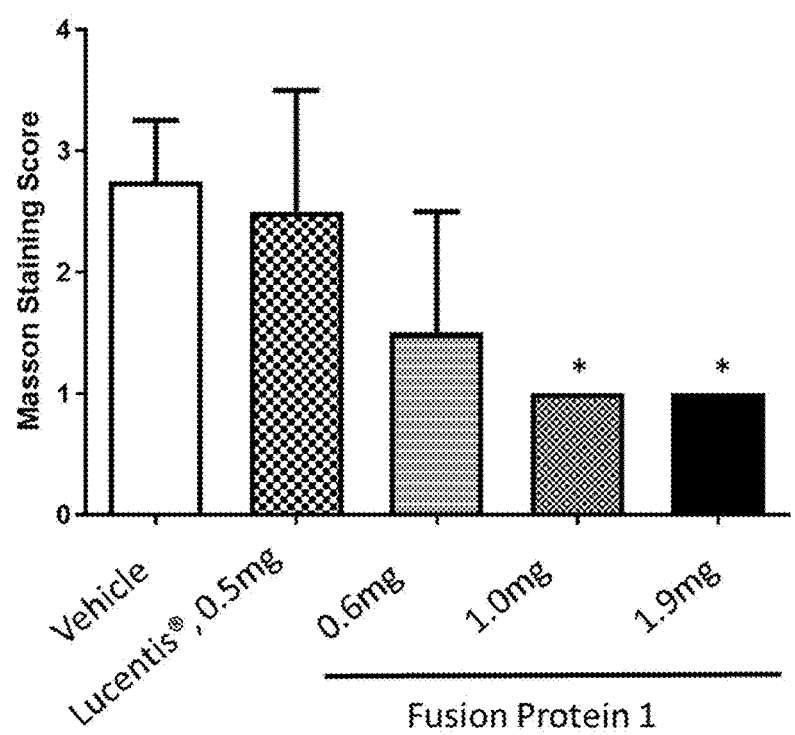
FIG. 3 is a graph of Masson's Trichrome staining of grade III/IV lesions of a laser-induced choroidal neovascularization model in rhesus monkeys treated as indicated. Data presented as mean±SEM. Enucleation was performed on Day 29. Selected Grade 4 lesion spots were analyzed by Masson's Trichrome staining. Student's t-test analysis was conducted to compare treatment group with vehicle group, *, p<0.05. n=4 eyes per group.

Histology examinations of eyes using Masson's staining for collagen (a precursor to fibrosis) showed a dose-dependent reduction in collagen thickness (ocular fibrosis) for Fusion Protein 1, but not for vehicle or Lucentis® treated groups (FIG. 3).

In conclusion, a single IVT injection of Fusion Protein 1 at 0.6, 1.0, and 1.9 mg/eye effectively inhibited vascular leakage, retinal thickness, and fibrosis in a laser-induced CNV model in rhesus monkeys. Based on the vitreal volume ratio between human (4 mL) and monkey (2 mL), these doses equate to a human equivalent dose of 1.2 mg, 2 mg, and 4 mg/eye. This supports the proposed doses of Fusion Protein 1 in the treatment of retinal diseases such as diabetic macular edema (DME) and neovascular age-related macular degeneration (nAMD). Furthermore, the data suggests that Fusion Protein 1 has an additive effect to benefit patients compared to the conventional anti-VEGF monotherapy.

Example 2. Evaluation of Fusion Protein 1 in a Bleomycine-Induced C57BL/6 Mouse Lung Fibrosis Model Fusion Protein 1, administered intravenously (IV) at 39 mg/kg, was evaluated for possible anti-fibrotic activity in a bleomycin-induced lung fibrosis mouse model. The mice were challenged with bleomycin at 1.5 U/kg by using a PENNCENTURY™ intrapulmonary aerosolizer on Day 1. The mice were intravenously administered Fusion Protein 1, Nintedanib Ethanesulfonate (Nintedanib) or vehicle (formulation buffer), daily from Day 1 to Day 21, and were sacrificed on Day 22. The total protein was precipitated out from collected lung tissue with 50% trichloroacetic acid on ice for 20 minutes. Samples were centrifuged and the pellet was mixed with 1 mL 12 N HCl and baked at 110° C. for 14-18 hours until samples were charred and dry. The samples were resuspended in 2 mL deionized water by incubating for 72 hours at room temperature while applying intermittent vortexing. Serial dilutions of trans-4-hydroxy-L-proline standard (source: Sigma, USA) were prepared starting at 0.5 mg/mL. The 200 vortexed sample (or standard) was added to 500 μL 1.4% chloramine T in 0.5 M sodium acetate/10% isopropanol (source: Fisher Sci, USA) and incubated for 20 minutes at room temperature. Next, 500 μL Ehrlich's solution (1.0 M p-dimethylaminobenzaldehyde in 70% isopropanol/30% perchloric acid) (source: Fisher Sci, USA) was added, mixed, and incubated at 65° C. for 15 minutes. After samples reached room temperature, the optical density of each sample and standard was measured at 550 nm and the concentration of lung hydroxyproline (m/lung) was calculated from the hydroxyproline standard curve. Proline is a major component of collagen, which is one of the markers used to assess fibrosis formation.

Figure 4:
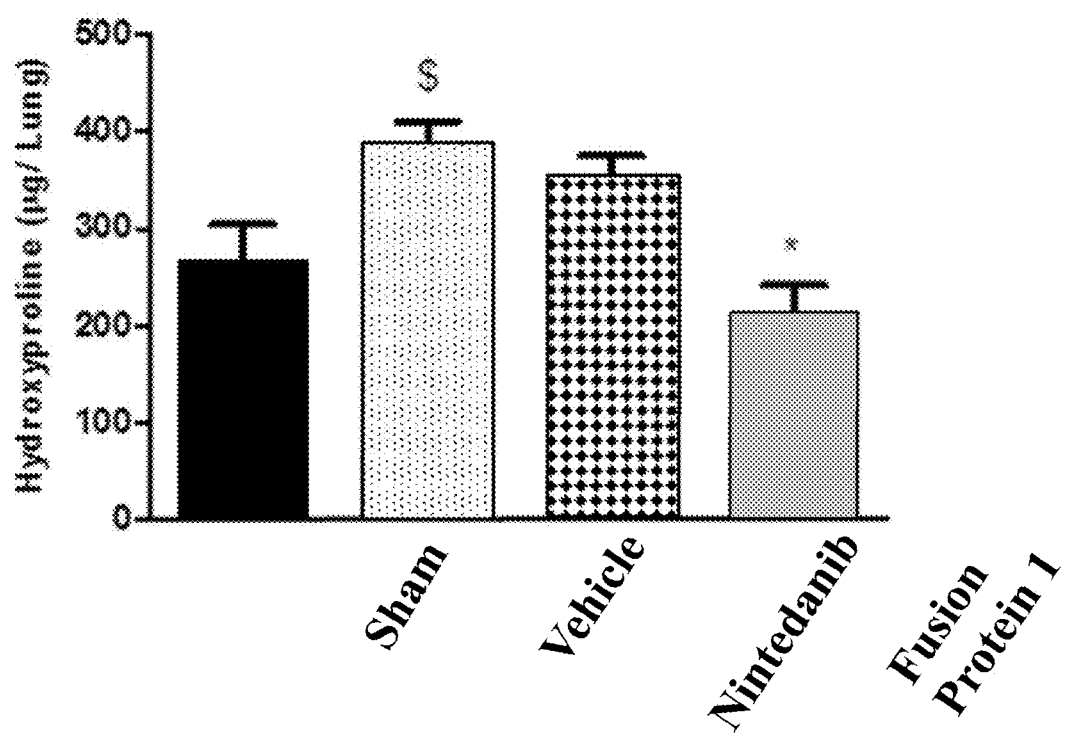
FIG. 4 is a graph of lung hydroxyproline levels in a belomycine-induced C57BL/6 mouse lung fibrosis model following treatment as indicated (n=8 animal for each treatment group and n=4 for the sham control group). $p<0.05, treated vs. sham control, unpaired Student's t-test; *p<0.05, treated vs. vehicle, One-way ANOVA and Dunnett's test. In the Fusion Protein 1 group, one animal data was not available due to early death with unknown reason on Day 3.

Lung hydroxyproline was significantly increased ($p<0.05$) in the vehicle control group (FIG. 4), suggesting a successful induction of lung fibrosis. Multiple administrations of Fusion Protein 1 markedly inhibited the hydroxyproline level ($p<0.05$) compared to the vehicle control, signifying an additive effect on these markers following Fusion Protein 1 injections (FIG. 4). Consecutive oral exposures of Nintedanib had a mild effect on reducing the level of hydroxyproline (FIG. 4).

Thus, Fusion Protein 1 administrated intravenously at 39 mg/kg once daily for 21 days was associated with significant reduction in lung hydroxyproline, a major lung fibrosis marker of bleomycin-induced lung fibrosis in mice.

Example 3. Pre-Formulation of Fusion Protein 1 for Intravitreal Injection

A pre-formulation study of Fusion Protein 1 was performed to develop a suitable liquid formulation of Fusion Protein 1. The objectives of the study were as follows:
1. To evaluate compatibility and colloidal stability of various concentrations Fusion Protein 1 (40 mg/mL and 80 mg/mL) with selected buffers,
2. To evaluate the changes of quality attributes under accelerated conditions (40° C., 25° C., 2-8° C.) after short-term storage,
3. Excipient selection: Tonicity, NaCl, polyols (i.e., trehalose, sucrose, mannitol, and sorbitol) and other stabilizers such as methionine, and arginine,
4. Evaluate compatibility through design of experiment (DoE) plan with the selected buffer and potential stabilizers; and
5. Assess the effect of cryoprotectants The formulation development work on the drug substance was initiated using a DoE approach to identify appropriate buffer, polyols, surfactants, and other stabilizers. Two concentrations, 40 and 80 mg/mL of Fusion Protein 1, were tested during the formulation development. Thermal stress as well as agitation and freeze/thaw stress were employed during the formulation development. Table 2 summarizes the ingredients and associated function tested in the following studies.

TABLE 2

Investigational formulation summary (ingredients screened).

| Items | Ingredients | Function | Tested Concentration |
|---|---|---|---|
| Buffer | Citric Acid | Buffering agent | 25 mM, pH 5.5 & pH 6.0 |
|  | Histidine |  | 25 mM, pH 6.0 & pH 6.5 |
|  | Sodium Phosphate |  | 25 mM, pH 6.5 & pH 7.0 |

TABLE 2-continued

Investigational formulation summary (ingredients screened).

| Items | Ingredients | Function | Tested Concentration |
|---|---|---|---|
| Amino acid | Methionine | Buffering agent | 40 mM |
|  | Arginine |  | 40 mM |
| Salt | NaCl | Tonicity and Buffer agent | 40 mM |
| Polyols | Sucrose | Tonicity and Stabilizer Agent | 190 mM |
|  | Mannitol |  | 190 mM |
|  | Trehalose |  | 190 mM |
|  | Sorbitol |  | 190 mM |
| Surfactant | PS20 | Stabilizer Agent | 0.03% |
|  | PS80 |  | 0.03% |

Colloidal Stability and Compatibly of Fusion Protein 1 in Various Buffers and pHs The solubility and diffusion coefficient (D) is commonly used to evaluate protein-protein interactions and is also used to demonstrate protein colloidal stability. Colloidal stability is a critical parameter to represent the long-term integrity of a molecule after dispersion and its resistance to sedimentation/precipitation in the solution. In addition, this method can rapidly capture the compatibility of a buffer toward the molecule. Consequently, Fusion Protein 1 was subjected to three commonly used ophthalmic solution buffers, sodium phosphate (NaPi), histidine (His), and citrate buffer (Cit) with potential buffering pH (Table 3). The attributes of Fusion Protein 1 were analyzed by size exclusion chromatography of high-performance liquid chromatography (SEC-HPLC) (Table 4), dynamic light scattering (DLS) (Table 5), and turbidity (FIG. 6).

TABLE 3

Investigated buffer systems and corresponding pH range.

| Buffer | Test Buffer pH | |
|---|---|---|
| 25 mM Sodium phosphate (Phosphate buffer) | 7.0 | 6.5 |
| 25 mM L-Histidine/L-Histidine hydrochloride (Histidine buffer) | 6.5 | 6.0 |
| 25 mM Citric Acid/Sodium Citrate (Citrate buffer) | 6.0 | 5.5 |

Figure 5A:
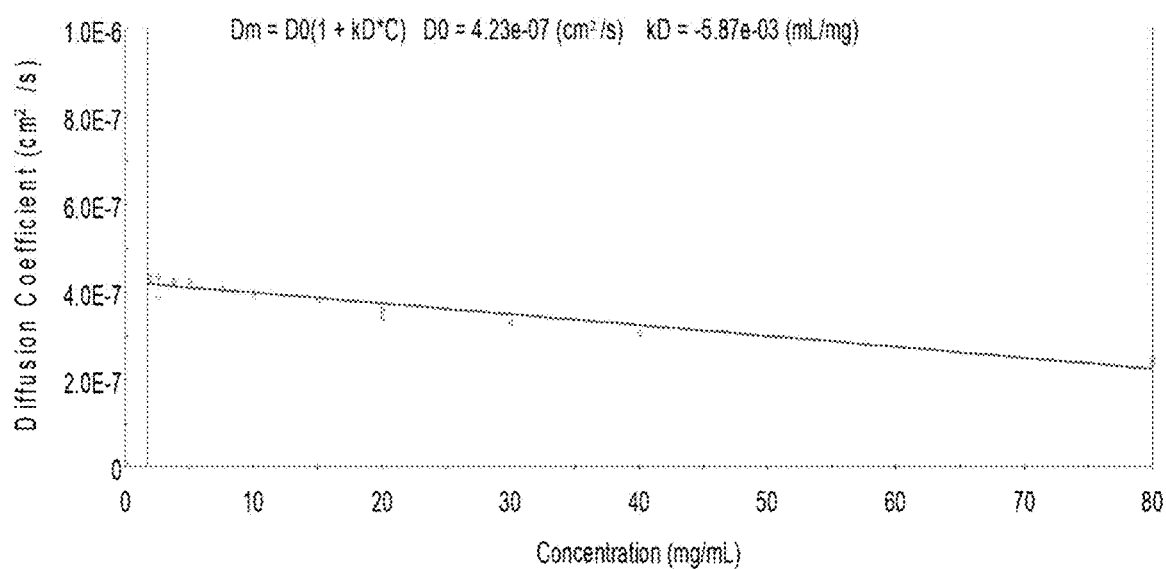
FIGS. 5A-5F are plots of the diffusion coefficients of Fusion Protein 1 in (FIG. 5A) phosphate buffer pH 7.0.
Figure 5B:
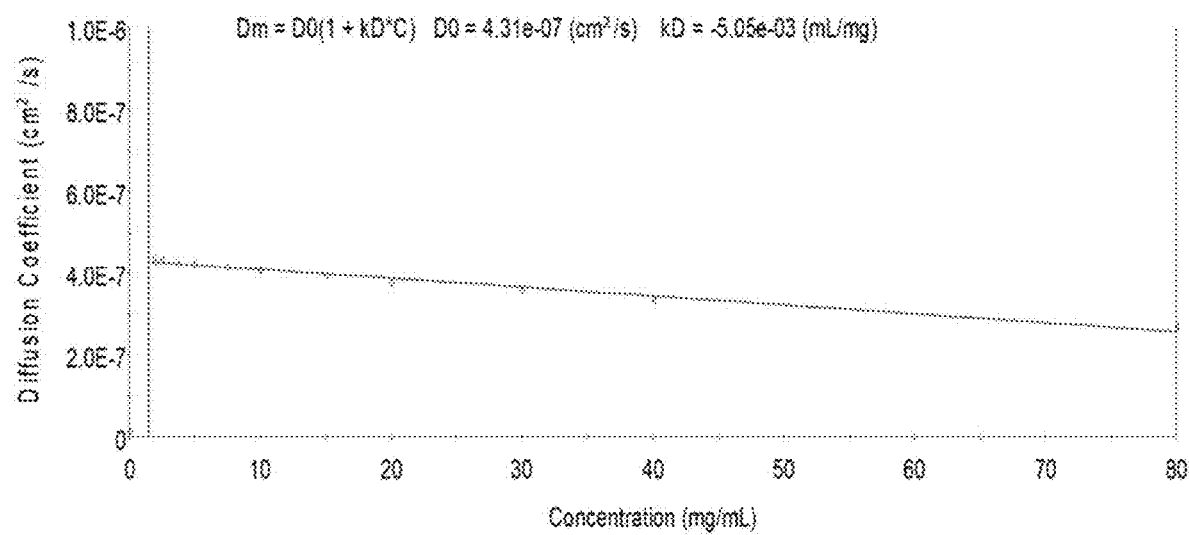
Figure 5C:
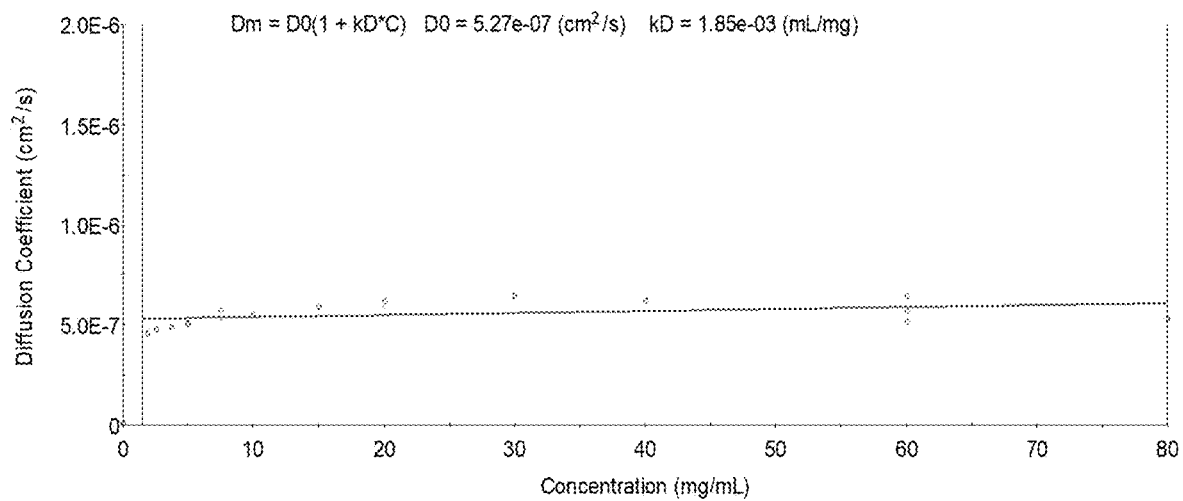
Figure 5D:
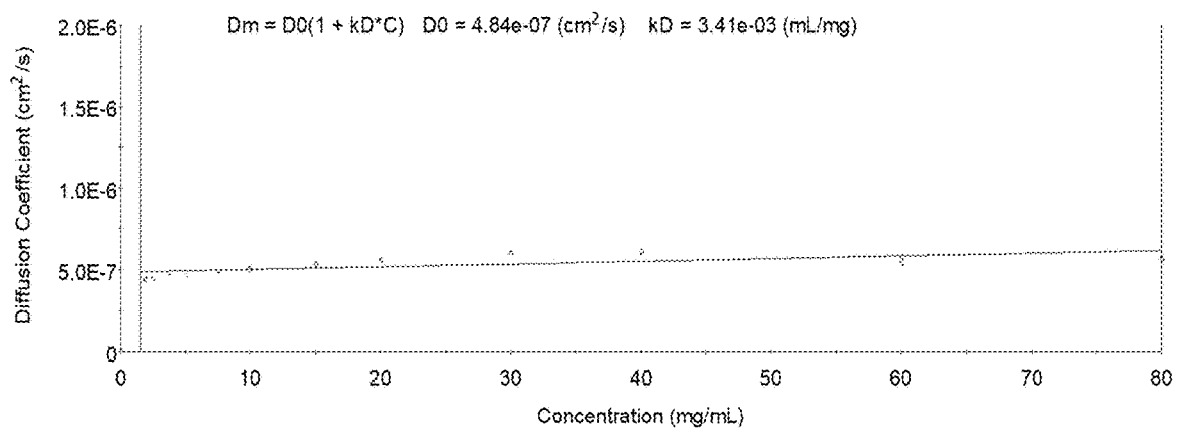
Figure 5E:
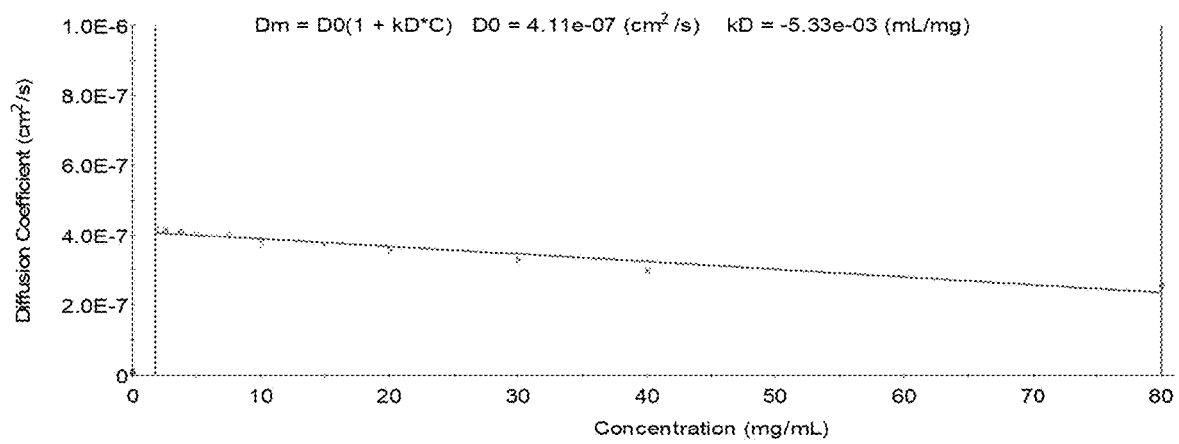
Figure 5F:
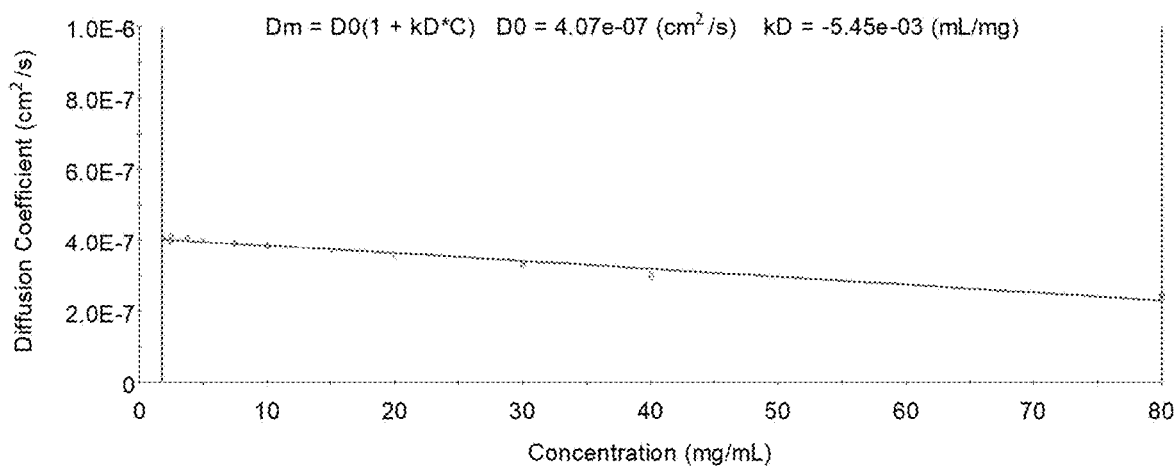

The diffusion coefficient of Fusion Protein 1 in phosphate and citrate buffers exhibited negative correlation with increasing concentration, which indicated the possibility of increased protein-protein interaction (FIGS. 5A, 5B, 5E, and 5F). In contrast, a repulsive protein-protein interaction of Fusion Protein 1 in histidine buffer at both 6.5 and 6.0 was observed with a positive correlation between diffusion coefficient and various concentrations of Fusion Protein 1 (FIGS. 5C and 5D). Thus, a repulsive intermolecular interaction Fusion Protein 1 in histidine buffer suggests favorable colloidal stability of Fusion Protein 1.

Figure 6A:
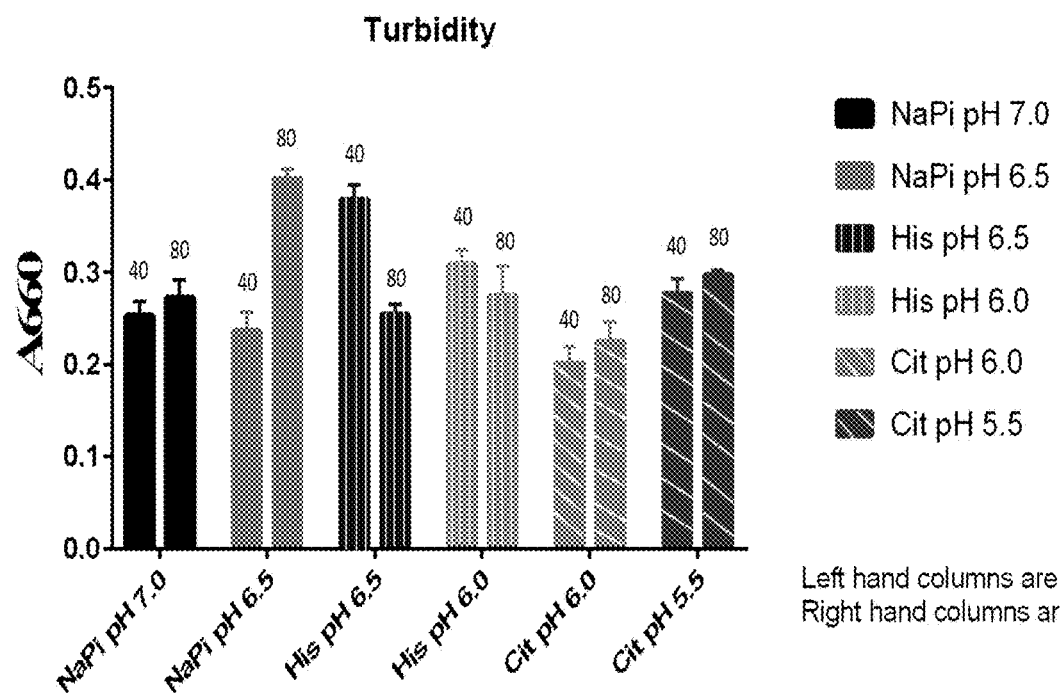
FIGS. 6A-6B are graphs of the turbidity measurement analyzed at two wavelengths for both 40 and 80 mg/L of Fusion Protein 1.
Figure 6B:
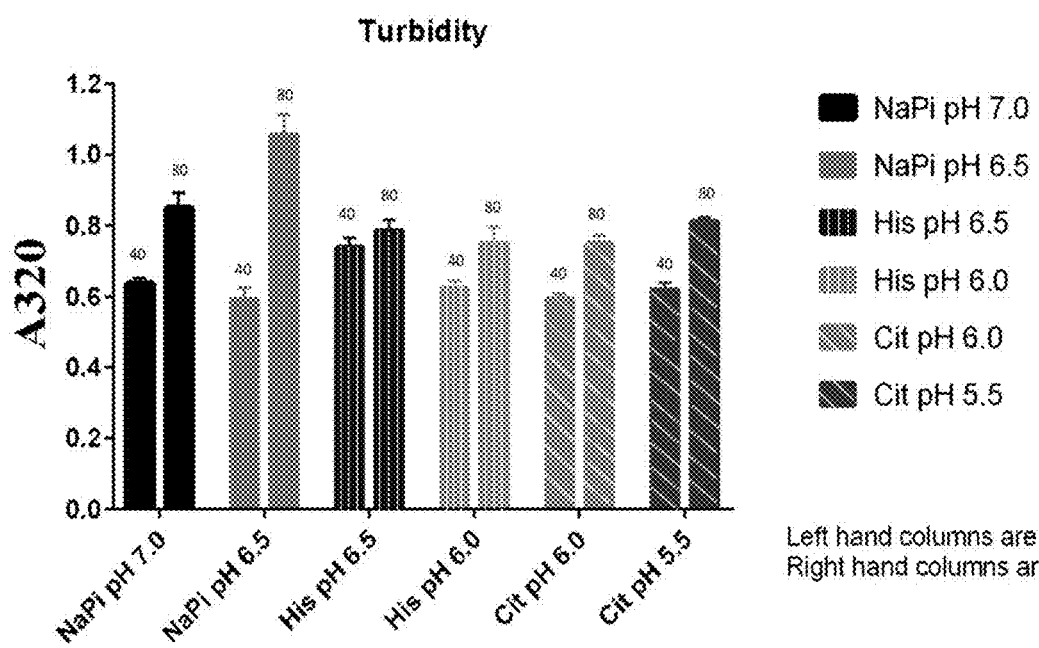
Figure 7A:
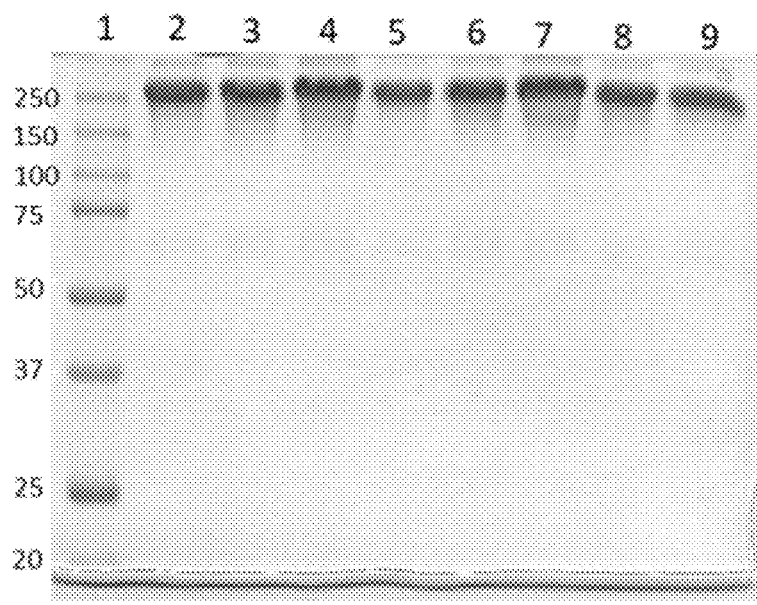
FIGS. 7A-7E are non-reducing SDS-PAGE with Coomassie Blue stained gels of Fusion Protein 1.
Figure 7B:
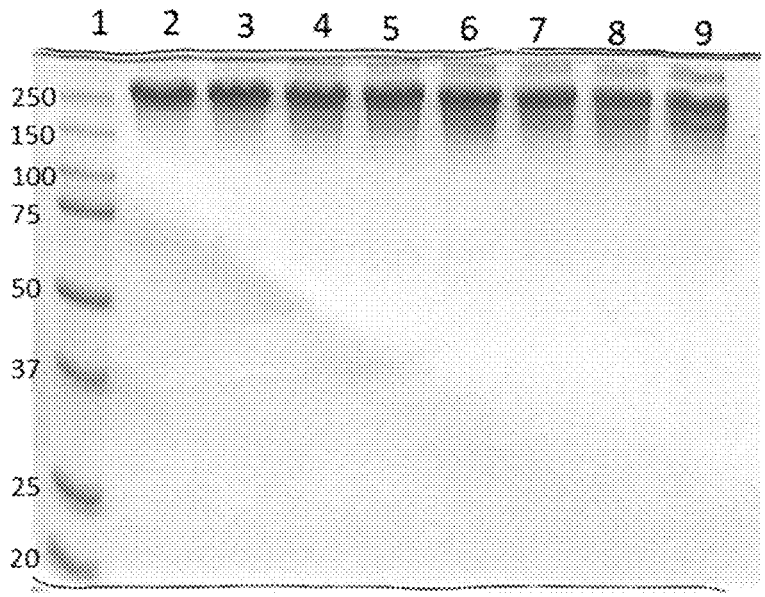
Figure 7C:
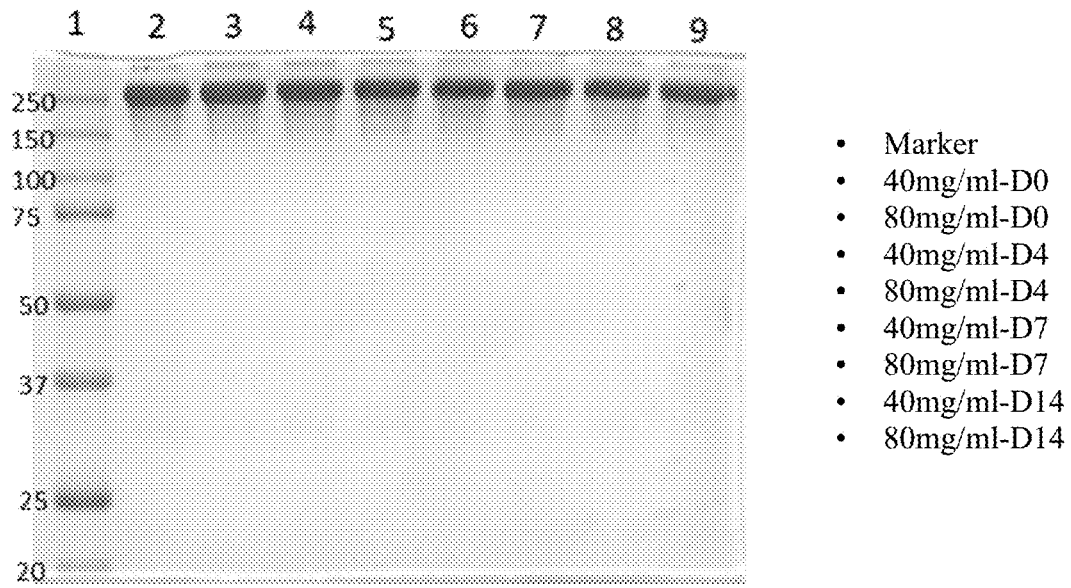
Figure 7D:
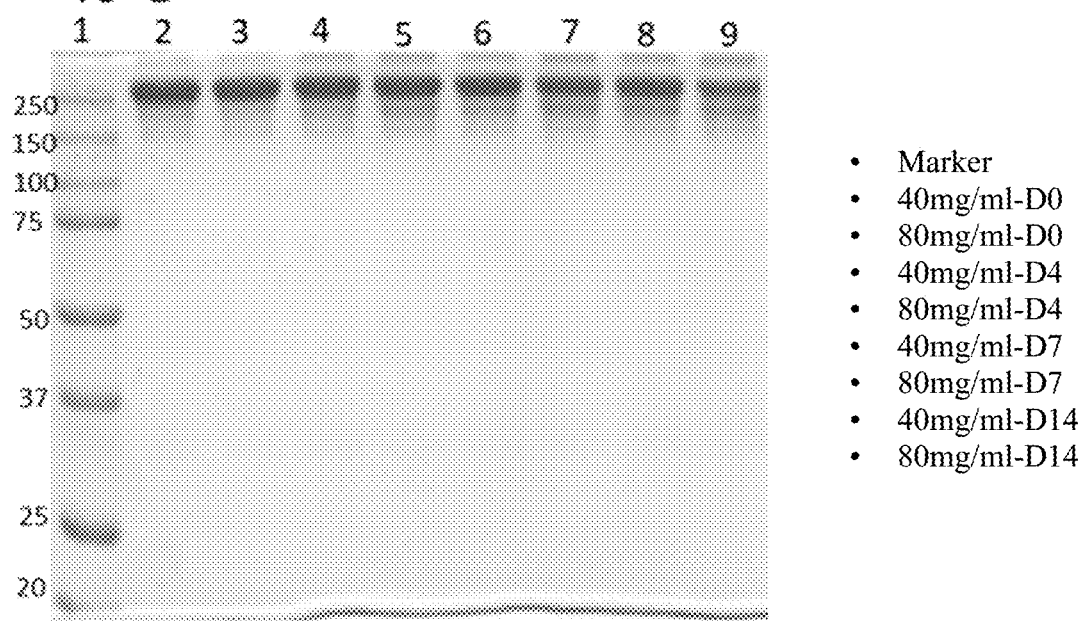
Figure 7E:
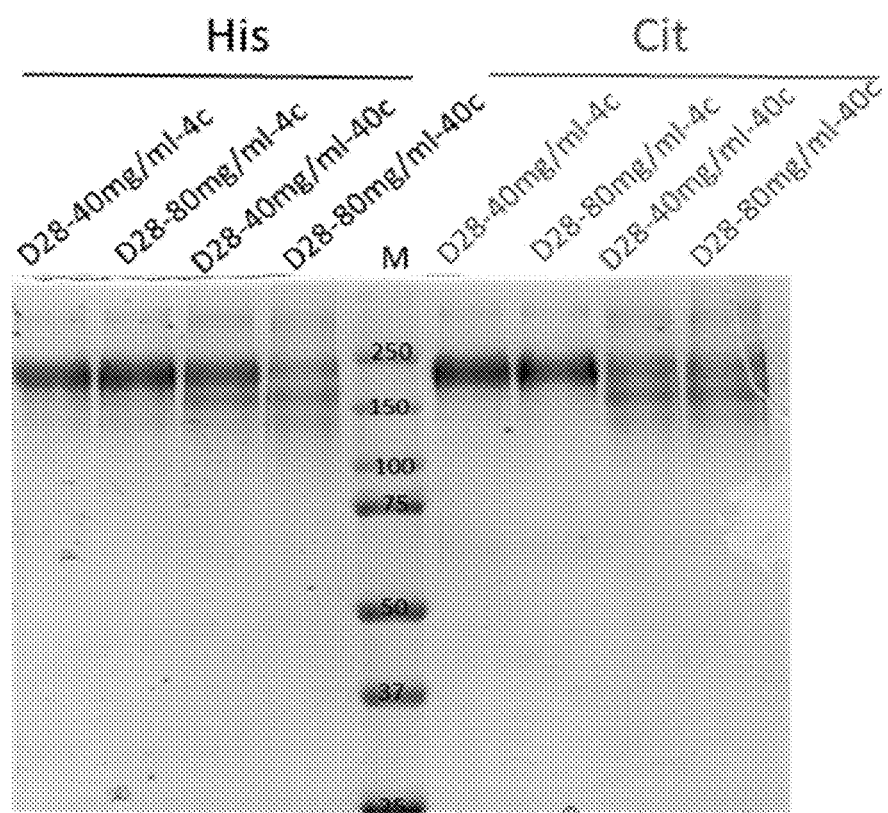
Figure 8A:
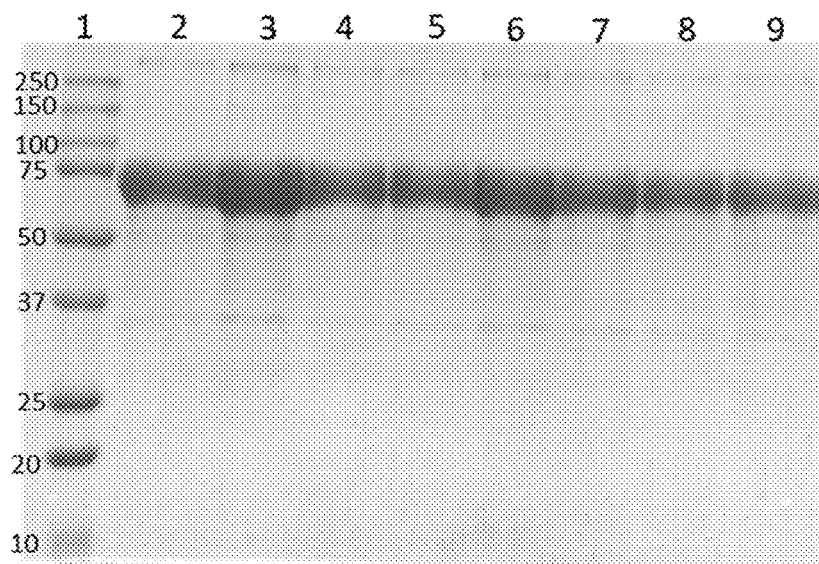
FIGS. 8A-8E are reducing SDS-PAGE gels with Coomassie Blue stained of Fusion Protein 1.
Figure 8B:
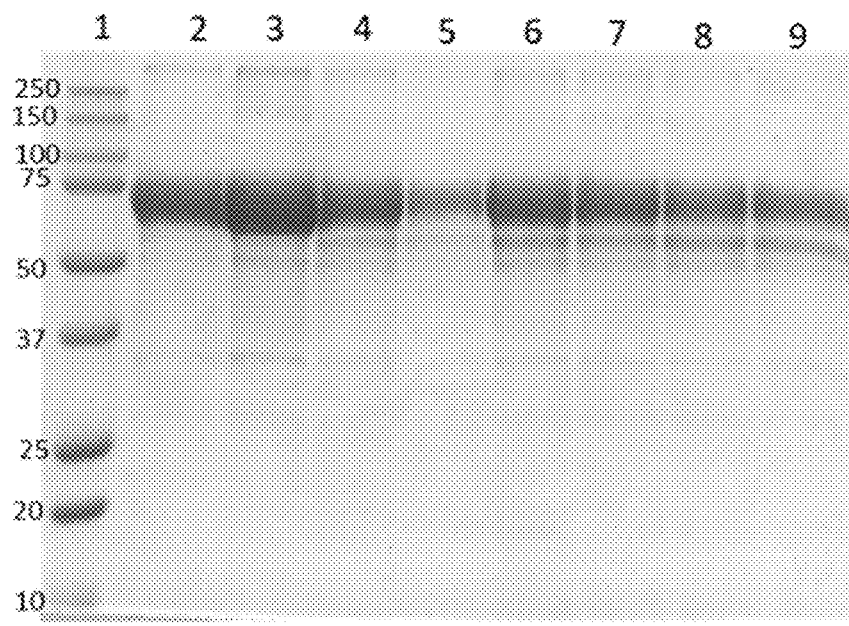
Figure 8C:
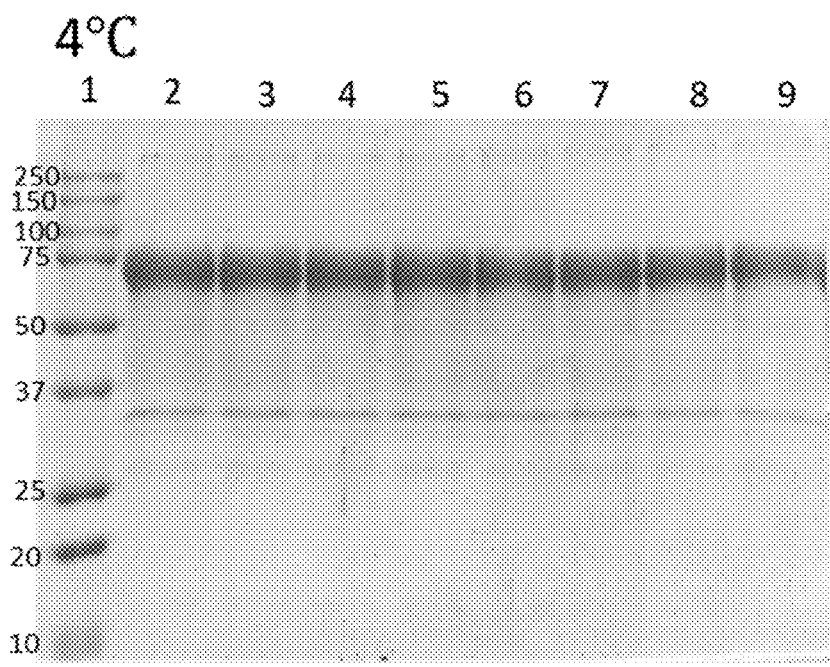
Figure 8D:
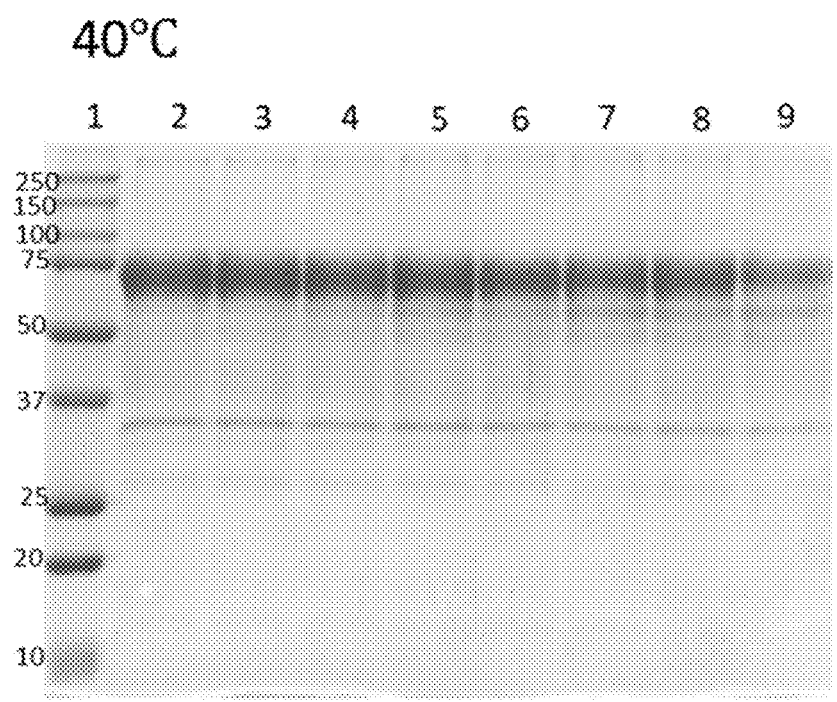
Figure 8E:
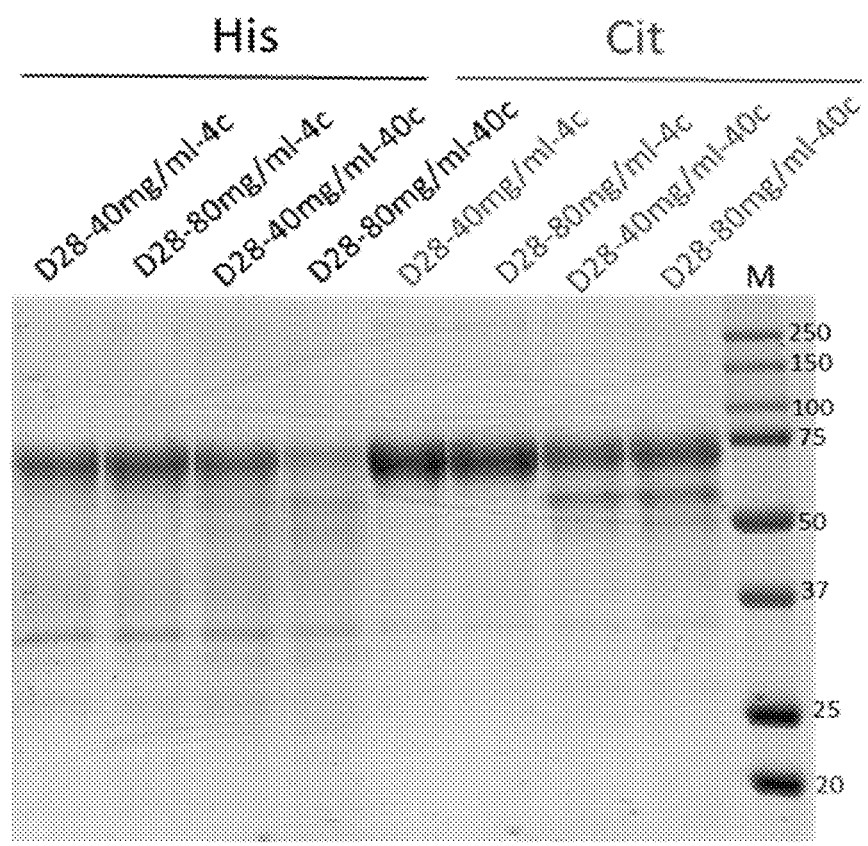

Descending diffusion coefficient was detected for all formulations, even for the histidine buffer formulations, as the concentration was increased above 40 mg/mL to 60 and 80 mg/mL Fusion Protein 1. For histidine buffer formulations, this suggests that preliminary aggregation may occur once the concentration is increased above 40 mg/mL. Based on results of SEC-HPLC, protein formulated at 80 mg/mL showed lower purity in buffer and greater high molecular weight aggregate for all buffers and pH, with the exception of histidine buffer, pH 6.5 (Table 4). Increased subvisible particles (100-1,000 nm, by DLS) were detected in all 80 mg/mL formulations compared to samples at 40 mg/mL (Table 5). There was no significant difference in turbidity between 40 and 80 mg/mL samples (FIGS. 6A and 6B).

Taken together, particle size analysis by DLS showed an increase in subvisible aggregates for all buffers as the protein concentration was increased from 40 to 80 mg/mL, a slight increase in HMW by SEC-HPLC was detected for all formulations except histidine buffer, pH 6.5, and no significant increase in turbidity was observed for any of the formulations.

TABLE 4

SEC-HPLC purity and UV concentration results of Fusion Protein 1 in different buffers.

| | Concentration (mg/mL) by A280 | | SEC-HPLC (%) | |
|---|---|---|---|---|
| Sample | Planned | Tested | HMW[a] | Main peak[b] |
| Reference 1[#] | 40 | 37.7 | 0.66 | 99.34 |
| 25 mM Citrate buffer, pH 5.5 | 40 | 45.2 | 0.55 | 99.45 |
|  | 80 | 76.9 | 0.77 | 99.23 |
| 25 mM Citrate buffer, pH 6.0 | 40 | 43.0 | 0.61 | 99.39 |
|  | 80 | 73.8 | 0.79 | 99.21 |
| 25 mM Histidine buffer, pH 6.0 | 40 | 42.8 | 0.48 | 99.52 |
|  | 80 | 79.7 | 0.52 | 99.48 |
| 25 mM Histidine buffer, pH 6.5 | 40 | 42.6 | 0.55 | 99.45 |
|  | 80 | 74.1 | 0.44 | 99.56 |
| 25 mM Phosphate buffer, pH 6.5 | 40 | 38.5 | 0.60 | 99.40 |
|  | 80 | 81.3 | 1.01 | 98.99 |
| 25 mM Phosphate buffer, pH 7.0 | 40 | 44.7 | 0.69 | 99.31 |
|  | 80 | 83.4 | 0.98 | 99.02 |

[#]Reference 1 is formulated in 25 mM histidine, 6% sucrose, 20 mN NaCl, 0.03% PS20, pH 6.0.
[a]HMW: aggregate as high molecule weight species with retention time at 8.3 ± 0.1 min;
[b]Main peak retention time is 9.5 ± 0.1 min, which represents non-aggregated dimeric form of Fusion Protein 1.

TABLE 5

DLS sub-visible particle distribution in different buffers.

| Buffer | pH | Conc. (mg/mL) | Average radius of first particle (0.1-10 nm) | % Pd | Average radius of second particle (10-100 nm) | % Pd | Average radius of third particle (100-1000 nm) | % Pd |
|---|---|---|---|---|---|---|---|---|
| Phosphate | 7.0 | 40 | 8.86 | 22.50 | — | — | — | — |
|  |  | 80 | 8.93 | 13.09 | — | — | 364.12 | 10.88 |
|  | 6.5 | 40 | 7.85 | 15.14 | — | — | — | — |
|  |  | 80 | 9.35 | 18.08 | — | — | 222.78 | 16.76 |
| Histidine | 6.5 | 40 | 4.86 | 54.30 | — | — | — | — |
|  |  | 80 | 4.52 | 27.13 | 25.6 | 18.32 | 475.84 | 19.79 |
|  | 6.0 | 40 | 3.68 | 7.64 | — | — | 213.06 | 6.28 |
|  |  | 80 | 3.40 | 5.40 | 52.19 | 8.50 | 799.23 | 11.84 |
| Citrate | 6.0 | 40 | 8.80 | 21.22 | — | — | — | — |
|  |  | 80 | 9.78 | 17.64 | — | — | 322.11 | 11.93 |
|  | 5.5 | 40 | 8.60 | 16.05 | — | — | — | — |
|  |  | 80 | 10.16 | 14.83 | — | — | 305.76 | 13.83 |

% Pd = percent poly dispersity

Buffer Selection and Fusion Protein 1 Attributes Assessment

The feasibility and accelerated stability of both 40 and 80 mg/mL Fusion Protein 1 formulated in 25 mM citrate or histidine buffer at pH 6.0 were tested. Non-aggregated (dimeric form) quantity of Fusion Protein 1 in citrate and histidine buffer stored at 2-8° C. showed no obvious change upon storage for both 40 and 80 mg/mL concentrations (Table 6). However, in accelerated condition at 40° C., the main peak for 80 mg/mL Fusion Protein 1 decreased by approximately 70% in the citrate buffer after 28 days (Table 7). In comparison, the content of Fusion Protein 1 decreased by approximately 50% when formulated in histidine buffer. Furthermore, the protein concentration at 80 mg/mL Fusion Protein 1 decreased by 29% for citrate buffer compared to no decrease in the histidine buffer. Thus, Fusion Protein 1 in histidine buffer is more stable than in citrate buffer at pH 6.0.

TABLE 6

Changes of protein content, purity, and aggregate of Fusion Protein 1 stored at 2-8° C. for 28 days.

| Buffer, pH | Planned Concentration (mg/mL) | Time point (days) | Tested Concentration (mg/mL) | SEC-HPLC (%) | |
|---|---|---|---|---|---|
| | | | | HMW[a] | Main peak[b] |
| 25 mM Citrate, pH 6.0 | 40 | 0 | 41.2 | 4.15 | 95.85 |
| | | 4 | 33.5 | 4.22 | 95.78 |
| | | 7 | 36.0 | 4.43 | 95.57 |
| | | 14 | 36.3 | 4.46 | 95.54 |
| | | 28 | 35.5 | 4.62 | 95.35 |
| | 80 | 0 | 79.3 | 4.32 | 95.69 |
| | | 4 | 59.1 | 4.51 | 95.49 |
| | | 7 | 65.7 | 4.61 | 95.39 |
| | | 14 | 72.4 | 4.89 | 95.11 |
| | | 28 | 61.7 | 5.13 | 94.87 |
| 25 mM Histidine, pH 6.0 | 40 | 0 | 38.5 | 4.07 | 95.93 |
| | | 4 | 35.3 | 4.28 | 95.72 |
| | | 7 | 35.7 | 4.39 | 95.61 |
| | | 14 | 37.6 | 4.59 | 95.41 |
| | | 28 | 37.0 | 4.92 | 95.08 |
| | 80 | 0 | 78.5 | 4.22 | 95.79 |
| | | 4 | 51.3 | 4.47 | 95.53 |
| | | 7 | 53.1 | 4.73 | 95.27 |
| | | 14 | 63.8 | 5.00 | 95.00 |
| | | 28 | 60.5 | 5.40 | 94.60 |

Samples analyzed by UV absorbance at $A_{280}$ (for concentration) and SEC-HPLC.
[a]HMW: aggregate as high molecule weight species with retention time at 8.3 ± 0.1 min;
[b]Main peak retention time is 9.5 ± 0.1 min, which represents non-aggregated dimeric form of Fusion Protein 1.

TABLE 7

Changes of protein content, purity, and aggregate of Fusion Protein 1 at 40° C. for 28 days.

| Sample | Planned Conc. (mg/mL) | Time point (days) | Tested Conc. (mg/mL) | SEC-HPLC (%) | | | |
|---|---|---|---|---|---|---|---|
| | | | | HHMW # | HMW[a] | Main peak[b] | LMW* |
| 25 mM Citrate, pH 6.0 | 40 | 0 | 41.2 | — | 4.15 | 95.85 | — |
| | | 4 | 33.9 | 10.02 | 14.94 | 75.04 | — |
| | | 7 | 30.3 | 15.60 | 20.25 | 63.02 | 1.13 |
| | | 14 | 37.4 | 28.78 | 21.34 | 47.67 | 2.21 |
| | | 28 | 39.4 | 35.26 | 22.87 | 38.89 | 2.98 |
| | 80 | 0 | 79.3 | — | 4.32 | 95.69 | — |
| | | 4 | 56.4 | 18.36 | 18.30 | 62.63 | 0.71 |
| | | 7 | 62.2 | 28.11 | 20.03 | 50.56 | 1.30 |
| | | 14 | 69.3 | 40.47 | 21.45 | 36.11 | 1.96 |
| | | 28 | 56.2 | 48.56 | 19.34 | 29.37 | 2.73 |
| 25 mM Histidine, pH 6.0 | 40 | 0 | 38.5 | — | 4.07 | 95.93 | — |
| | | 4 | 35.3 | 1.82 | 7.84 | 90.34 | — |
| | | 7 | 35.7 | 1.44 | 11.04 | 87.53 | — |
| | | 14 | 38.9 | 4.68 | 13.35 | 80.87 | 1.10 |
| | | 28 | 36.8 | 9.01 | 18.79 | 70.90 | 1.31 |
| | 80 | 0 | 78.5 | — | 4.22 | 95.79 | — |
| | | 4 | 61.7 | 3.85 | 11.22 | 84.93 | — |
| | | 7 | 67.8 | 5.73 | 14.42 | 79.33 | 0.52 |
| | | 14 | 81.2 | 11.32 | 20.12 | 67.46 | 1.10 |
| | | 28 | 78.5 | 25.02 | 22.69 | 50.32 | 1.97 |

[a]HMW: aggregate as high molecule weight species with retention time at 8.3 ± 0.1 min
[b]Main peak retention time is 9.5 ± 0.1 min, which represents non-aggregated dimeric form of Fusion Protein 1
*HHMW: aggregate as higher molecule weight species which refer to a peak that has retention time at 7.6 ± 0.1 min
LMW: low molecular weight with retention time at 13.5 ± 0.1 min
"—" Not detectable Additionally, Fusion Protein 1 in citrate buffer showed greater reduction of main band intensity at the position of approximately 250 kDa in non-reducing SDS-PAGE (FIGS. 7A-7E) after incubation at 40° C. (FIGS. 8A-8E). The protein degradation profile of Fusion Protein 1 resulted in increasing bands of product degraded fragments and high molecular weight aggregate over time. Analysis by reducing SDS-PAGE showed reduction of main band intensity at approximately 75 kDa and increased fragment bands (FIGS. 8A-8E). Overall, protein purity and integrity investigation indicated that Fusion Protein 1 exhibited better stability in 25 mM histidine buffer at pH 6.0 than in citrate buffer.

The accelerated condition with short-term storage to freeze/thaw was also evaluated to examine changes of quality attributes of Fusion Protein 1 samples. Samples were incubated at 40° C. for 4 days. One freeze thaw cycle of −70° C. and room temperature (RT) tests indicated that Fusion Protein 1 was stable without polyol protection (Table 8).

TABLE 8

Changes of protein purity and aggregate of Fusion Protein 1 after one freeze-thaw cycle.

| Sample | Planned Conc. (mg/mL) | Treatment | SEC-HPLC (%) | |
|---|---|---|---|---|
| | | | HMW[a] | Main Peak[b] |
| 25 mM Citrate, pH 6.0 | 40 | Before | 4.15 | 95.85 |
| | | After | 4.13 | 95.76 |
| | 80 | Before | 4.32 | 95.69 |
| | | After | 4.14 | 95.56 |
| 25 mM Histidine, pH 6.0 | 40 | Before | 4.07 | 95.93 |
| | | After | 4.24 | 95.87 |
| | 80 | Before | 4.22 | 95.79 |
| | | After | 4.44 | 95.86 |

[a]HMW: aggregate as high molecule weight species with retention time at 8.3 ± 0.1 min
[b]Main peak retention time is 9.5 ± 0.1 min, which represents non-aggregated dimeric form of Fusion Protein 1.

Excipient Screening

To investigate the suitability of excipients, a pilot study was conducted to evaluate the main peak purity change by SEC-HPLC of formulated Fusion Protein 1 samples. Based on the studies described above, 25 mM histidine buffer pH 6.0 was selected for further excipient screening tests. Three types of additives included were polyols, salt, and amino acid. Evaluations were designed to have eleven conditions and tested by accelerated condition at 40° C. for 4 days (Table 9).

TABLE 9

Excipients screened.

| #Test | Tested Stabilizer at 150 mM | | | | 40 mM | Amino acid at 40 mM | |
|---|---|---|---|---|---|---|---|
| | Trehalose | Mannitol | Sucrose | Sorbitol | NaCl | Arginine | Methionine |
| 0  | — | — | — | — | — | — | — |
| 1  | + | — | — | — | — | — | — |
| 2  | — | + | — | — | — | — | — |
| 3  | — | — | + | — | — | — | — |
| 4  | — | — | — | + | — | — | — |
| 5  | — | — | — | — | + | — | — |
| 6  | + | — | — | — | + | — | — |
| 7  | — | + | — | — | + | — | — |
| 8  | — | — | + | — | + | — | — |
| 9  | — | — | — | + | + | — | — |
| 10 | — | — | + | — | — | + | — |
| 11 | — | — | + | — | — | — | + |

Note:
Fusion Protein 1 was formulated in 25 mM histidine buffer pH 6.0 and tested with each different polyol (test #1 to 4) or combined with 40 mM NaQ (test #6-9). Test# 5 = 40 mM NaQ without polyol or amino acid. Tests #10 and 11 = sucrose combined with 2 amino acids.

Main peak purity was ≥90% when formulated with each polyol (Table 10, tests #1-4), the combination of trehalose with NaCl (test #6), and combination of sucrose with methionine (test #11).

TABLE 10

Purity of Fusion Protein 1 added with various excipients after 4 days at 40° C.

| | SEC-HPLC (%) | | | |
|---|---|---|---|---|
| #Test | HHMW# | HMW$^a$ | Main peak$^b$ | LMW* |
| Before treatment | — | 4.07 | 95.93 | — |
| 0  | 2.11 | 8.35  | 89.21 | 0.33 |
| 1  | 1.59 | 6.81  | 91.23 | 0.37 |
| 2  | 1.26 | 5.91  | 92.66 | 0.18 |
| 3  | 1.74 | 7.21  | 90.74 | 0.31 |
| 4  | 1.84 | 7.48  | 90.31 | 0.37 |
| 5  | 2.09 | 7.99  | 89.63 | 0.30 |
| 6  | 1.64 | 6.89  | 90.93 | 0.54 |
| 7  | 2.44 | 8.23  | 88.94 | 0.40 |
| 8  | 2.56 | 8.71  | 88.43 | 0.30 |
| 9  | 2.26 | 8.30  | 89.08 | 0.36 |
| 10 | 9.57 | 16.38 | 73.88 | 0.17 |
| 11 | 1.52 | 6.32  | 91.81 | 0.36 |

$^a$HMW: aggregate as high molecule weight species with retention time at 8.3 ± 0.1 min
$^b$Main peak retention time is 9.5 ± 0.1 min, which represents the non-aggregated dimeric form of Fusion Protein 1.
HHMW: aggregate as higher molecule weight species which refer to a peak that has retention time at 7.6 ± 0.1 min
*LMW: low molecular weight with retention time at 13.5 ± 0.1 min
"—" Not detectable Combinations of the remaining polyols with NaCl had slightly increased % of aggregate (Table 10, tests #6, 7, 8, 9) compared to tests without NaCl. In the combination of arginine and sucrose, the purity decreased to 73.88% with over 16% aggregate after stored at accelerated condition (Table 10, test #10). Consequently, trehalose, sucrose, and mannitol were selected to proceed to the design of experiment investigation.

Optimize Composition Candidate Formulations by DoE

To investigate the significance resulting from the stabilizer candidates and clarify the cross-effect of NaCl with individual polyol, the selected polyols and various concentrations of NaCl were tested via the planned DoE as shown in Table 11. The accelerated study conditions and analysis are summarized in Table 12. According to the SEC-HPLC results (Table 13), 25 mM His buffer pH 6.0 with 200 mM polyol/sugar (especially trehalose and sucrose) provided the best protection of Fusion Protein 1 against thermal stress to maintain a high percent purity of Fusion Protein 1.

TABLE 11

DoE plan to test 80 mg/mL Fusion Protein 1 with various concentrations of ingredients.

| Test # | Polyol* (mM) | Sodium Chloride (mM) |
|---|---|---|
| 1  | 112.5 | 25 |
| 2  | 200   | 50 |
| 3  | 112.5 | 25 |
| 4  | 200   | 0  |
| 5  | 200   | 50 |
| 6  | 200   | 0  |
| 7  | 25    | 0  |
| 8  | 112.5 | 25 |
| 9  | 25    | 0  |
| 10 | 25    | 50 |
| 11 | 25    | 50 |

*polyol means trehalose, sucrose, or mannitol, each tested individually with or without NaCl.

TABLE 12

Accelerated condition testing.

| Storage Condition | Time points | Analysis | |
|---|---|---|---|
| 40 ± 2° C./75 ± 5% RH | Days 0, 4, and 7 | Purity | Osmolality |
| 25 ± 2° C./60 ± 5% RH | Days 0 and 7 | | |
| 5 ± 3° C. | Days 0 and 7 | | |

Following storage of 80 mg/mL Fusion Protein 1 samples at 40° C. for 4 and 7 days (Table 12), in 25 mM histidine buffer at pH 6.0 formulated with 200 mM polyols stabilized Fusion Protein 1 against thermal stress, maintained the relative purity >80%, and provided the best resulting purity of Fusion Protein 1 (Test #4 and 6 in Table 13). The samples with polyol and 50 mM NaCl (tests #2 and #5) all showed lower purity than samples with polyol alone (tests #4 and 6). This effect also was observed for samples with 25 mM polyol and no NaCl (tests #7 and 9) compared to samples with 25 mM polyol and 50 mM NaCl (tests #10 and 11). The differences between these combinations were not differentiated at 4° C. and 25° C. (data not shown).

TABLE 13

Purity and osmolality analysis of
Fusion Protein 1 samples stored at 40° C.

| Sample | #Relative Purity of Main Peak Analyzed by SEC-HPLC (%) | | Osmolality (mOsm/kg) |
|---|---|---|---|
| | 4 days | 7 days | |
| Trehalose | | | |
| Test 1 | 86.70 | 78.32 | 256 |
| Test 2 | 86.83 | 80.97 | 451 |
| Test 3 | 86.49 | 79.29 | 247 |
| Test 4 | 90.23 | 85.48 | 312 |
| Test 5 | 87.30 | 81.05 | 432 |
| Test 6 | 90.31 | 85.41 | 304 |
| Test 7 | 86.50 | 79.85 | 77 |
| Test 8 | 86.51 | 79.30 | 253 |
| Test 9 | 86.51 | 79.83 | 73 |
| Test 10 | 82.22 | 72.47 | 195 |
| Test 11 | 81.87 | 72.32 | 201 |
| Mannitol | | | |
| Test 1 | 85.30 | 77.47 | 246 |
| Test 2 | 85.92 | 78.27 | 415 |
| Test 3 | 86.60 | 78.98 | 231 |
| Test 4 | 89.01 | 83.62 | 300 |
| Test 5 | 85.95 | 78.49 | 417 |
| Test 6 | 89.41 | 83.93 | 295 |
| Test 7 | 86.34 | 79.15 | 77 |
| Test 8 | 85.49 | 77.51 | 239 |
| Test 9 | 86.70 | 79.88 | 75 |
| Test 10 | 81.22 | 71.36 | 193 |
| Test 11 | 81.42 | 71.74 | 186 |
| Sucrose | | | |
| Test 1 | 86.92 | 79.71 | 256 |
| Test 2 | 87.51 | 80.38 | 431 |
| Test 3 | 86.64 | 78.89 | 249 |
| Test 4 | 90.10 | 85.21 | 301 |
| Test 5 | 87.62 | 81.60 | 431 |
| Test 6 | 90.43 | 85.59 | 325 |
| Test 7 | 86.88 | 79.64 | 77 |
| Test 8 | 86.84 | 79.17 | 248 |
| Test 9 | 87.12 | 79.89 | 75 |
| Test 10 | 82.13 | 72.52 | 194 |
| Test 11 | 82.43 | 72.61 | 195 |

Relative purity showed the purity of samples at 40° C. which was normalized with T0 samples (baseline).

Although higher histidine buffer with 200 mM polyol maintained quality attributes of protein, osmolality must be maintained to the ocular physiology range of 280-310 mOsm/kg. Therefore, 300 mOsm/kg was set as the target DoE statistical calculation. The composition of ingredients selected to formulate Fusion Protein 1 at 80 mg/mL were 25 mM histidine buffer at pH 6.0, 190 mM trehalose, sucrose or combination of trehalose and sucrose.

Assess Potential Excipients Composition of the Formula

To evaluate the compatibility of suitable ingredients in the combined formula, further tests examined 80 mg/mL Fusion Protein 1 for use in 4 candidate formulations. In this study, 0.03% polysorbate 20 (PS20) or polysorbate 80 (PS80) were added together with trehalose or sucrose to assess Fusion Protein 1 attributes after treated with accelerated condition for a week and/or a month, various freeze-thaw cycles between −20° C. and room temperature (RT), and agitation after 24 and 48 hours (Tables 14A-14B). Short-term compatibility of the container was tested in parallel.

TABLE 14A

Candidate formulations added with cryoprotectants and analyzed for 28 days at 4° C. and 40° C.

| Test | Container | Attributes | Time point Condition | T0 | D4 | D7 | D14 | D28 |
|---|---|---|---|---|---|---|---|---|
| Thermal | 2R Type I borosilicate glass vial | Purity Sub-visible particulate Integrity Content Potency | 4° C. | base-line | — | — | V | V |
| | | | 40° C. | | V | V | — | — |

V = tested time point;
T = time;
D = Day.

TABLE 14B

Candidate formulations added with cryoprotectants and tested in Freeze/thaw or Agitation

| Test | Container | Attributes | Treatment | Cycles/Time point | |
|---|---|---|---|---|---|
| Freeze-thaw | 0.2 mL cryovial | Purity Potency Sub-visible particulate Integrity | Freeze: at −20° C. for 23 hr Thaw: at 25° C. for 1 hr | 3 cycles | 6 cycles |
| Agitation | 2R Type I borosilicate glass vial | Content | Shaking: 220 rpm at 25° C. Blank control: stationary at 25° C. | 24 hr | 48 hr |

The 4 candidate formulation compositions showed similar observations about the changes of attributes for the thermal stress studies. Fusion Protein 1 at 80 mg/mL concentration was sensitive to the temperature at 40° C., which caused main peak reduction to less than 95% and over 5% aggregate by 7 days. This was not observed at 4° C. storage for at least one month (Tables 15 and 16). Moreover, the relative potency of VEGF and/or integrin αvβ3 binding compared to reference was within target range (70-130%) and showed slight changes on VEGF binding and no obvious changes of αvβ3 binding following storage at accelerated conditions.

In particular, size exclusion chromatography studies indicated that a formulation of 25 mM histidine, 190 mM trehalose, and 0.03% PS20, pH 6.0 enabled better stability of Fusion Protein 1 than other formulations at both 4° C. and 40° C.

TABLE 15

Stability results of the thermal test at 4° C.

| Candidate | Component | Time point (days) | Tested Conc. (mg/mL) | SEC-HPLC (%) HMW[a] | SEC-HPLC (%) Main Peak[b] | Relative Potency* (%) VEGF binding | Relative Potency* (%) αvβ3 binding |
|---|---|---|---|---|---|---|---|
| Reference 1# | 25 mM histidine, 6% sucrose, 20 mM NaCl, 0.03% PS20, pH 6.0 | NA | 37.7 | NA | NA | 100 | 100 |
| 1 | 25 mM histidine, 0.03% PS20 190 mM trehalose, | 0 | 73.5 | 0.94 | 99.06 | 86.2 | 96.9 |
|   |   | 14 | 73.1 | 1.31 | 98.69 | 87.7 | 91.8 |
|   |   | 28 | 74.5 | 1.78 | 98.22 | 88.3 | 119.7 |
| 2 | 25 mM histidine, 190 mM sucrose, 0.03% PS20 | 0 | 78.7 | 0.83 | 99.17 | 93.3 | 85.9 |
|   |   | 14 | 83.5 | 1.47 | 98.53 | 90.9 | 96.4 |
|   |   | 28 | 85.8 | 1.99 | 98.01 | 87.8 | 131.5 |
| 3 | 25 mM histidine, 0.03% PS80 190 mM trehalose, | 0 | 81.9 | 0.85 | 99.15 | 86.6 | 141.8 |
|   |   | 14 | 83.0 | 1.46 | 98.54 | 88.6 | 107.3 |
|   |   | 28 | 85.4 | 2.04 | 97.96 | 91.3 | 134.9 |
| 4 | 25 mM histidine, 190 mM sucrose 0.03% PS80 | 0 | 80.6 | 0.74 | 99.26 | 90.0 | 118.5 |
|   |   | 14 | 81.6 | 1.41 | 98.59 | 95.6 | 109.9 |
|   |   | 28 | 81.9 | 1.99 | 98.02 | 89.7 | 114.7 |

[a]HMW: aggregate as high molecule weight species with retention time at 8.3 ± 0.1 min
Reference 1 formulated in 25 mM histidine, 6% sucrose, 20 mM NaCl, 0.03% PS20, pH 6.0
[b]Main peak retention time is 9.5 ± 0.1 min, which represents non-aggregated dimeric form of Fusion Protein 1
*relative potency was planned to be within 70-130% compared to reference.
NA, not applicable.

TABLE 16

Stability results of the thermal test at 40° C.

| Candidate | Component | Time point (days) | Conc. (mg/mL) | SEC-HPLC (%) HMW[a] | SEC-HPLC (%) Main[b] | Relative Potency* (%) VEGF binding | Relative Potency* (%) αvβ3 binding |
|---|---|---|---|---|---|---|---|
| Reference 1# | 25 mM histidine, 6% sucrose, 20 mM NaCl, 0.03% PS20, pH 6.0 | NA | 37.7 | NA | NA | 100 | 100 |
| 1 |   | 0 | 73.5 | 0.94 | 99.06 | 86.2 | 96.9 |
|   | 25 mM mM trehalose, 0.03% PS20 histidine, 190 | 4 | 74.2 | 4.18 | 95.82 | 80.8 | 122.5 |
|   |   | 7 | 72.9 | 6.43 | 93.58 | 82.1 | 95.5 |
| 2 | 25 mM 0.03% PS20 histidine, 190 mM sucrose, | 0 | 78.7 | 0.83 | 99.17 | 93.3 | 85.9 |
|   |   | 4 | 82.6 | 5.21 | 94.79 | 83.8 | 92.7 |
|   |   | 7 | 79.5 | 7.24 | 92.76 | 87.7 | 94.1 |
| 3 | 25 mM 0.03% PS80 histidine, 190 mM trehalose, | 0 | 81.9 | 0.85 | 99.15 | 86.6 | 141.8 |
|   |   | 4 | 83.6 | 5.09 | 94.91 | 82.9 | 87.4 |
|   |   | 7 | 82.6 | 7.34 | 92.66 | 78.2 | 102.7 |
| 4 | 25 mM 0.03% PS80 histidine, 190 mM sucrose | 0 | 80.6 | 0.74 | 99.26 | 90.0 | 118.5 |
|   |   | 4 | 80.3 | 4.85 | 95.15 | 86.5 | 70.2 |
|   |   | 7 | 81.7 | 7.38 | 92.63 | 77.7 | 112.7 |

Reference 1 formulated in 25 mM histidine, 6% sucrose, 20 mM NaCl, 0.03% PS20, pH 6.0
[a]HMW: aggregate as high molecule weight species with retention time at 8.3 ± 0.1 min
[b]Main peak retention time is 9.5 ± 0.1 min, which represents non-aggregated dimeric form of Fusion Protein 1
*Target relative potency was planned to be within 70-130% compared to reference.
NA, not applicable.

Fusion Protein 1 at 80 mg/mL formulated in the candidate formulation was tested for the quality attributes after freezing at −20° C. for approximately 23 hours and thaw at 25° C. for at least 1 hour for 3 and 6 cycles. Analysis by SEC-HPLC did not detect any obvious changes in the percent main peak of Fusion Protein 1 and its aggregate (Table 17). The remaining protein was more than 95% and the aggregate was less than 5%. Additionally, the potency of Fusion Protein 1 binding to VEGF or integrin αvβ3 compared to the reference was decreased to less than 70% in candidates #3 and #4 (Table 17).

TABLE 17

Stress stability tests after 3 and 6 freeze-thaw (F/T) cycles.

| Candidate | Composition | No. of F/T cycle | Conc. (mg/mL) By A280 | SEC-HPLC (%) HMW$^a$ | Main Peak$^b$ | Relative Potency* (%) VEGF binding | αvβ3 binding |
|---|---|---|---|---|---|---|---|
| Reference 1# | 25 mM histidine, 6% sucrose, 20 mM NaCl, 0.03% PS20, pH 6.0 | 4 | 37.7 | NA | NA | 100 | 100 |
| 1 | 25 mM histidine, 190 mM trehalose, 0.03% PS20 | 0 | 73.5 | 0.94 | 99.06 | 86.2 | 96.9 |
|  |  | 3 | 77.6 | 1.34 | 98.66 | 76.9 | 100.3 |
|  |  | 6 | 80.1 | 1.11 | 98.90 | 83.2 | 106.4 |
| 2 | 25 mM histidine, 190 mM sucrose, 0.03% PS20 | 0 | 78.7 | 0.83 | 99.17 | 93.3 | 85.9 |
|  |  | 3 | 82.3 | 1.32 | 98.68 | 83.0 | 96.7 |
|  |  | 6 | 84.9 | 1.15 | 98.85 | 93.2 | 153.0 |
| 3 | 25 mM histidine, 190 mM trehalose, 0.03% PS80 | 0 | 81.9 | 0.85 | 99.15 | 86.6 | 141.8 |
|  |  | 3 | 85.5 | 1.35 | 98.65 | 77.0 | 100.7 |
|  |  | 6 | 86.8 | 0.99 | 99.01 | 82.8 | 54.8* |
| 4 | 25 mM histidine, 190 mM sucrose, 0.03% PS80 | 0 | 80.6 | 0.74 | 99.26 | 90.0 | 118.5 |
|  |  | 3 | 87.4 | 1.32 | 98.68 | 57.5* | 99.2 |
|  |  | 6 | 88.2 | 1.09 | 98.91 | 87.5 | 99.5 |

Reference 1 formulated in 25 mM histidine, 6% sucrose, 20 mM NaCl, 0.03% PS20, pH 6.0
$^a$HMW: aggregate as high molecule weight species with retention time at 8.3 ± 0.1 min.
$^b$Main peak retention time is 9.5 ± 0.1 min, which represents non-aggregated dimeric form of Fusion Protein 1.
*Target relative potency was planned to be within 70-130% compared to reference.
NA, not applicable.

The agitation studies tested protein stability to mimic potential handling and transportation with Fusion Protein 1 in liquid form. The conditions are accelerated by shaking the vials at 220 rpm for 24 and 48 hours under a 25° C. environment. Treating the protein samples under such a rigorous condition did impact the protein purity and binding to the major targets compared to samples exposed at the stationary condition and baseline (Table 18).

TABLE 18

Stress stability test by agitation for 24 and 48 hours.

| Candidate | Component | Test | Tested Duration (hrs) | Conc. (mg/mL) | SEC-HPLC (%) HMW$^a$ | Main Peak$^b$ | Relative Potency* (%) VEGF binding | αvβ3 binding |
|---|---|---|---|---|---|---|---|---|
| Reference 1# | 25 mM histidine, 6% sucrose, 20 mM NaCl, 0.03% PS20, pH 6.0 | NA | NA | 37.73 | NA | NA | 100 | 100 |
| 1 | 25 mM PS20 | Baseline | 0 | 73.5 | 0.94 | 99.06 | 86.2 | 96.9 |

TABLE 18-continued

Stress stability test by agitation for 24 and 48 hours.

| Candidate | Component | Test | Duration (hrs) | Tested Conc. (mg/mL) | SEC-HPLC (%) HMW[a] | Relative Potency* (%) | | |
|---|---|---|---|---|---|---|---|---|
| | | | | | | Main Peak[b] | VEGF binding | αvβ3 binding |
| | histidine, | Stationary | 24 | 72.5 | 1.30 | 98.7 | 81.3 | 105.5 |
| | 190 mM | Agitation | | 72.1 | 1.44 | 98.56 | 82.3 | 118.7 |
| | trehalose, | Stationary | 48 | 71.5 | 1.74 | 98.26 | 103.4 | 118.7 |
| | 0.03% | Agitation | | 77.8 | 1.53 | 98.47 | 76.3 | 111.0 |
| 2 | 25 mM PS20 | Baseline | 0 | 78.7 | 0.83 | 99.17 | 93.3 | 85.9 |
| | histidine, | Stationary | 24 | 83.8 | 1.43 | 98.57 | 79.1 | 98.6 |
| | 190 mM | Agitation | | 87.7 | 1.58 | 98.42 | 76.5 | 89.3 |
| | sucrose, | Stationary | 48 | 82.9 | 1.86 | 98.14 | 108.0 | 119.0 |
| | 0.03% | Agitation | | 85.3 | 1.79 | 98.21 | 84.5 | 78.7 |
| 3 | 25 mM PS80 | Baseline | 0 | 81.9 | 0.85 | 99.15 | 86.6 | 141.8 |
| | histidine, | Stationary | 24 | 83.1 | 1.50 | 98.5 | 75.8 | 88.9 |
| | 190 mM | Agitation | | 83.3 | 1.61 | 98.39 | 78.8 | 103.0 |
| | trehalose, | Stationary | 48 | 85.9 | 1.88 | 98.12 | 97.7 | 103.3 |
| | 0.03% | Agitation | | 82.3 | 1.72 | 98.28 | 81.5 | 94.2 |
| 4 | 25 mM PS80 | Baseline | 0 | 80.6 | 0.74 | 99.26 | 90.0 | 118.5 |
| | histidine, | Stationary | 24 | 81.3 | 1.50 | 98.5 | 80.6 | 131.8 |
| | 190 mM | Agitation | | 80.3 | 1.58 | 98.42 | 82.7 | 123.4 |
| | sucrose, | Stationary | 48 | 86.4 | 1.89 | 98.11 | 105.4 | 183.1 |
| | 0.03% | Agitation | | 78.5 | 1.71 | 98.29 | 85.7 | 134.4 |

Reference 1 formulated in 25 mM histidine, 6% sucrose, 20 mM NaCl, 0.03% PS20, pH 6.0
[a]HMW: aggregate as high 1 molecule weight species with retention time at 8.3 ± 0.1 min.
[b]Main peak retention time is 9.5 ± 0.1 min, which represents non-aggregated dimeric form of Fusion Protein 1.
*Target relative potency was planned to be within 70-130% compared to reference.
NA, not applicable.

In addition to the critical quality attributes such as quantity, purity, and potency, the formation and distribution of sub-visible particles after the stress conditions were examined. According to dynamic light scattering (DLS) analysis, the observed sub-visible particles were categorized by size, % polydispersity, and the proportion of different size of particles. The results indicated that the progress to obtain concentrated Fusion Protein 1 to the desired concentration 80 mg/mL was not monitored appropriately, thus, not only the major Fusion Protein 1 molecule with radius approximately 5 nm was detected, but also the aggregate can be seen as larger size particles i.e., 10-100 nm or 100-1000 nm at baseline (D0). It was not possible to conclude which candidate formulation buffer worked the best by DLS.

Moreover, non-reducing and reducing SDS-PAGE analyses were not able to differentiate the change of integrity of Fusion Protein 1 after treating with stress conditions. Osmolality of these tested candidate formulations (Table 19) showed that except for candidate #4 which showed lower osmolality, the other formulations were of similar range.

TABLE 19

Osmolality of candidate formulations.

| Formulation | Composition | Osmolality (mOsm/kg) |
|---|---|---|
| 1 | 25 mM Histidine, 190 mM trehalose, 0.03% PS20, pH 6.0 | 248 |
| 2 | 25 mM Histidine, 190 mM Sucrose, 0.03% PS20, pH 6.0 | 257 |
| 3 | 25 mM Histidine, 190 mM trehalose, 0.03% PS80, pH 6.0 | 250 |
| 4 | 25 mM Histidine, 190 mM Sucrose, 0.03% PS80, pH 6.0 | 209 |

CONCLUSION

Based on the results, composition of formulation 1 with 25 mM His buffer containing 190 mM trehalose and 0.03% PS20 pH 6.0, was nominated to be tested in a pilot drug product for a 12 month stability study.

Example 4. Formulation of Fusion Protein 1 for Intravitreal Injection

A stability study was conducted to develop the final formulation of Fusion Protein 1.

Bulk Drug Substance Concentration Testing

To select the suitable concentration to support final bulk drug substance of Fusion Protein 1 through the manufacturing process, both 40 and 80 mg/mL Fusion Protein 1 were formulated in the leading formulation component (25 mM histidine, 190 mM trehalose, and 0.03% PS20, pH 6.0). Formulations with both concentrations of Fusion Protein 1 were tested under short-term accelerated condition to assess critical quality attributes for any changes by SEC-HPLC, DLS, and SDS-PAGE analyses.

Protein quantity exhibited variably among the 40 mg/mL samples and 80 mg/mL samples for short term storage at 40° C. for 7 days (Table 20). A slightly greater amount of aggregate was observed at 80 mg/mL. Results for samples stored at 40° C., indicated that Fusion Protein 1 formed less high molecule weight aggregate at 40 mg/mL compared to 80 mg/mL by day 4 and day 7. The test #2 protein sample at 40 mg/mL with NaCl exhibited >5% aggregate detected. Freeze/Thaw cycle tests did not show obvious changes of the aggregate % or purity for both 40 and 80 mg/mL samples (data not shown).

TABLE 20

Stability of Fusion Protein 1 at 40 and 80 mg/mL in formulation buffer with and without NaCl at 40° C.

| Sample | Composition | Duration (days) | Tested Conc. (mg/mL) | SEC-HPLC (%) HMW[a] | Main Peak[b] |
|---|---|---|---|---|---|
| Test 1 | 40 mg/mL Fusion Protein 1 25 mM Histidine, 190 mM trehalose, 0.03% PS20, pH 6.0 | 0 4 7 | 42.8 48.3 49.9 42.2 43.3 | 1.52 2.83 2.93 3.69 3.74 | 98.48 97.17 97.07 96.31 96.26 |
| Test 2 | 40 mg/mL Fusion Protein 1 25 mM Histidine, 190 mM trehalose, 10 mM NaCl, 0.03% PS20, pH 6.0 | 0 4 7 | 42.9 45.4 46.3 42.5 42.4 | 1.63 4.22 4.26 5.20 5.21 | 98.38 95.78 95.74 94.02 94.07 |
| Test 3 | 80 mg/mL Fusion Protein 1 25 mM Histidine, 190 mM trehalose, 0.03% PS20, pH 6.0 | 0 4 7 | 87.3 90.8 90.0 86.2 86.2 | 1.63 4.75 4.73 6.55 6.52 | 98.37 94.67 94.64 92.34 92.49 |
| Test 4 | 80 mg/mL Fusion Protein 1 25 mM Histidine, 190 mM trehalose, 10 mM NaCl, 0.03% PS20, pH 6.0 | 0 4 7 | 85.6 88.1 92.9 84.3 84.4 | 1.66 5.08 5.08 6.95 6.98 | 98.34 94.22 94.22 91.78 91.90 |

[a]HMW: aggregate as high molecule weight species with retention time at 8.3 ± 0.1 min.
[b]Main peak retention time is 9.5 ± 0.1 min, which represents non-aggregated dimeric form of Fusion Protein 1.

DLS was used to analyze sub-visible particles and distribution and all protein samples contained particles in size ranges from 10 nm-100 nm and/or 100-1000 nm at baseline, which made it impossible to differentiate changes after stress tests.

Pilot Drug Product Stability Test

Based on the studies described above, and where Fusion Protein 1 maintained the most consistent purity based on SEC-HPLC, the selected formulation composition for Fusion Protein 1 was as follows: 40 mg/mL Fusion Protein 1, 25 mM histidine, 190 mM trehalose and 0.03% PS20 at pH 6.0. To verify and evaluate the compatibility with the container system as well as to collect initial stability, 40 mg/mL Fusion Protein 1 was prepared in this formula, filled in borosilicate Type I glass vials (rubber stoppered and flip-cap sealed), and incubated under three conditions, −25° C. to −15° C., 2-8° C., and 25° C./60% relative humidity (RH) (Table 21).

TABLE 21

Formulation development study plan.

| | Test Time Point | | | | | | |
|---|---|---|---|---|---|---|---|
| Condition | T = 0 | 2 wks | 1M | 3M | 6M | 9M | 12M |
| 25° C. /60% RH | X | X | X | X | X | — | — |
| 4° C. | | X | X | X | X | X | X |
| −20° C. in 2R vial | X | X | X | X | X | — | — |

X = time point to check the quality attributes of the protein.
Wks = weeks;
M = months;
T = time The results of the study indicated that 40 mg/mL Fusion Protein 1 was stable when stored at −20° C. for at least 12 months (Table 22). After 6 months in the storage condition at 4° C., there was a slight decrease in purity and increase of aggregate (Table 23). In terms of accelerated storage at 25° C., SEC-HPLC detected increased aggregate % through 6 months, however the main peak remained ≥95% and the molecule specific potency and integrity (i.e., data of capillary electrophoresis sodium dodecyl sulfate (CE-SDS)) were maintained with minimal changes (Table 24).

TABLE 22

Pilot drug product stability of Fusion Protein 1 stored at −20°C.

| Test Article | Time point (months) | Conc. (mg/mL) By A280 | SEC-HPLC (%) HMW[a] | Main Peak[b] | VEGF binding Relative Potency[@] %/EC$_{50}$ | CE-SDS Non-reducing (%) | Reducing (%) |
|---|---|---|---|---|---|---|---|
| Z19003[#] | 0 | 41 | 0.8 | 99.20 | 92/0.408 | 100 | 99.3 |
| | 1 | 41.6 | 0.94 | 99.06 | 96/0.368 | 100 | 100 |
| | 3 | 42.3 | 1.14 | 98.86 | 98/0.393 | 100 | 99.5 |
| | 6 | 41.0 | 0.72 | 99.28 | 97/0.397 | 100 | 99.3 |
| | 9 | 42.2 | 0.95 | 99.05 | 95/0.407 | 100 | 99.6 |
| | 12 | 43.4 | 0.71 | 99.29 | 93/0.370 | 100 | 99.4 |
| Z19003[#] (1x F/T cycle) | 0 | 41 | 0.87 | 99.13 | 92/0.408 | 100 | 99.3 |
| | 1 | 41.8 | 0.87 | 99.13 | 95/0.374 | 100 | |
| | 3 | 42.3 | 0.93 | 99.07 | 102/0.380 | 100 | 99.1 |
| | 6 | 42.0 | 0.76 | 99.24 | 96/0.401 | 100 | 98.8 |
| | 9 | 41.7 | 0.99 | 99.01 | 95/0.409 | 100 | 99.5 |
| | 12 | 42.3 | 0.72 | 99.28 | 93/0.372 | 100 | 99.5 |

[a]HMW: aggregate as high molecule weig it species with retention time at 8.3 ± 0.1 min.
[b]Main peak retention time is 9.5 ± 0.1 min, which represents non-aggregated dimeric form of Fusion Protein 1.
[@]Relative potency is calculated based on EC$_{50}$ value compared to the baseline (D0).
[#]Z19003 is Lot No. of the test article.

TABLE 23

Pilot drug product stability result of Fusion Protein 1 at 4° C.

| Test Article | Time-point (months) | Conc. (mg/mL) By A280 | SEC-HPLC HMW[a] | SEC-HPLC Main Peak[b] | VEGF binding Relative Potency[@] %/EC$_{50}$ | CE-SDS Non-reducing (%) | CE-SDS Reducing (%) |
|---|---|---|---|---|---|---|---|
| Z19003[#] | 0 | 41.0 | 0.8 | 99.20 | 92/0.408 | 100 | 99.3 |
| | 0.5 | 41.7 | 0.97 | 99.04 | 98/0.250 | 100 | 99.5 |
| | 1 | 42.4 | 1.15 | 98.85 | 93/0.381 | 100 | 99.8 |
| | 3 | 41.8 | 1.60 | 98.41 | 93/0.461 | 100 | 99.2 |
| | 6 | 41.0 | 1.41 | 98.59 | 89/0.431 | 100 | 99.4 |
| | 9 | 41.3 | 2.18 | 97.83 | 101/0.377 | 100 | 99.4 |
| | 12 | 42.0 | 1.80 | 98.20 | 95/0.365 | 100 | 99.4 |
| Z19003[#] (1x F/T cycle) | 0 | 41.0 | 0.87 | 99.13 | 92/0.408 | 100 | 99.3 |
| | 0.5 | 42.1 | 0.93 | 99.07 | 97/0.254 | 100 | 99.2 |
| | 1 | 42.3 | 1.12 | 98.88 | 91/0.389 | 100 | 99.4 |
| | 3 | 44.7 | 1.47 | 98.53 | 86/0.499 | 100 | 99.4 |
| | 6 | 41.6 | 1.43 | 98.57 | 89/0.432 | 100 | 99.3 |
| | 9 | 41.5 | 2.21 | 97.79 | 95/0.398 | 100 | 99.6 |
| | 12 | 41.4 | 1.94 | 98.06 | 97/0.357 | 100 | 99.4 |

[a]HMW: aggregate as high molecule weight species with retention time at 8.3 ± 0.1 min.
[b]Main peak retention time is 9.5 ± 0.1 min, which represents non-aggregated dimeric form of Fusion Protein 1.
[@]Relative potency is calculated based on EC$_{50}$ value compared to the baseline (D0).
[#]Z19003 is Lot No. of the test article.

TABLE 24

Pilot drug product stability result of Fusion Protein 1 at 25° C.

| Test Article | Timepoint (months) | Conc. By A280 (mg/mL) | SEC-HPLC HHMW[#] | SEC-HPLC HMW[a] | SEC-HPLC Main Peak[b] | VEGF binding Relative Potency[@]%/EC$_{50}$ | CE-SDS Non-reducing (%) | CE-SDS Reducing (%) |
|---|---|---|---|---|---|---|---|---|
| Z19003[#] | 0 | 41.0 | — | 0.8 | 99.20 | 92/0.408 | 100 | 99.3 |
| | 0.5 | 42.9 | — | 1.40 | 98.60 | 94/0.263 | 100 | 99.3 |
| | 1 | 42.6 | — | 1.85 | 98.15 | 99/0.370 | 100 | 99.1 |
| | 3 | 42.8 | 0.365 | 3.21 | 96.43 | 92/0.421 | 100 | 98.7 |
| | 6 | 41.8 | — | 3.30 | 96.70 | 78/0.494 | 100 | 98.7 |
| Z19003[#] (1x F/T cycle) | 0 | 41.0 | — | 0.87 | 99.13 | 92/0.408 | 100 | 99.3 |
| | 0.5 | 43.8 | — | 1.42 | 98.59 | 91/0.271 | 100 | 99.2 |
| | 1 | 40.9 | — | 1.89 | 98.11 | 95/0.373 | 100 | 99.3 |
| | 3 | 44.5 | 0.214 | 2.90 | 96.88 | 91/0.424 | 100 | 98.7 |
| | 6 | 41.3 | — | 3.49 | 96.51 | 80/0.480 | 100 | 86.8 |

[a]HMW: aggregate as high molecule weight species with retention time at 8.3 ± 0.1 min.
bMain peak retention time is 9.5 ± 0.1 min, which represents non-aggregated dimeric form of Fusion Protein 1.
[#]HHMW: aggregate as higher molecule weight species which refer to a peak that has retention time at 7.6 ± 0.1 min
[@]Relative potency is calculated based on EC$_{50}$ value compared to the baseline (D0).
[#]Z19003 is Lot No. of the test article.

According to the DLS analysis, sub-visible particles were not detected when the Test Articles were stored at −20° C. and 4° C. for at least 12 months, except for one sample stored at 4° C. which experienced one freeze/thaw cycle at the 12 month time point and formed larger size particles (radius 2208 nm) in a trace amount (2%). Larger size particles (radius 2195 and 2264 nm) were detected in 3 and 6-months samples stored at 25° C.

A backup of the sample stored at 4° C. was analyzed to confirm the presence of sub-visible particles observed at 12 months. This sample was also stored for 12 months and underwent a freeze/thaw cycle. Sub-visible particles were observed in the studied backup sample. Therefore, Fusion Protein 1 is sensitive to the freeze/thaw stress following storage for 12 months at 4° C. Consequently, without freeze/thaw cycle, Fusion Protein 1 can be stored at 4° C. for at least 12 months. However, if Fusion Protein 1 is to be stored longer than 6 months then storage at −20° C. is recommended.

Figure 9:
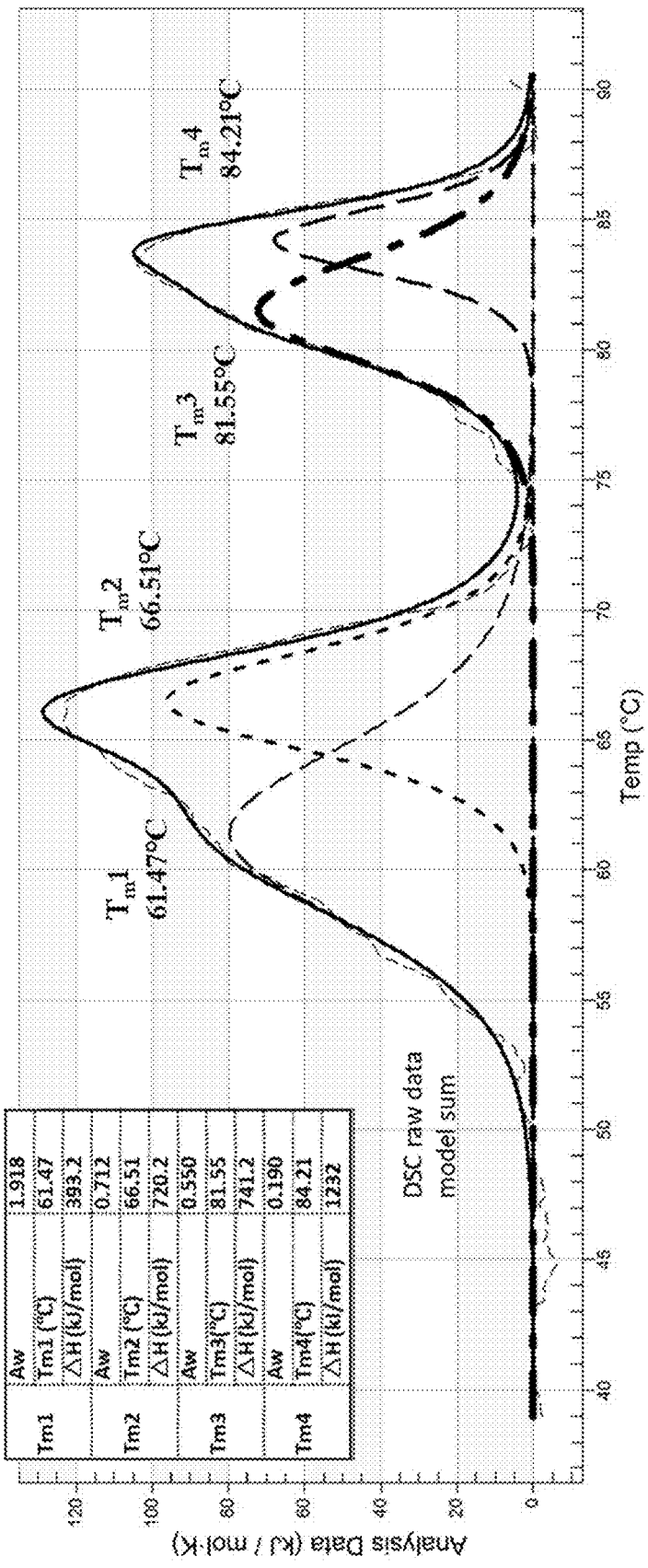
FIG. 9 is a graph of the thermal stability of Fusion Protein 1 at 1 mg/mL formulated in 25 mM histidine buffer, 190 mM trehalose, 0.03% PS20 at pH 6.0 and determined by Differential Scanning calorimeter (DSC).

The viscosity measurement of the formulation was obtained using a viscometer. The subject formulation (40 mg/mL Fusion Protein 1 in 25 mM histidine buffer solution with selected ingredients) had low viscosity with 5.402 cP (centipoise) (Table 25). The selected formulation has favorable thermal properties for the protein, as shown by the representative differential scanning calorimetry (DSC) thermogram in FIG. 9. The deconvoluted thermogram has 4 thermal transition peaks, with Tm values at 61.47° C., 66.51° C., 81.55° C., to 84.21° C.

TABLE 25

Viscosity of formulation solution
and Fusion Protein 1 in the solution at 4° C.

| Test Samples | Formulation solution (Fusion Protein 1, 0 mg/mL 25 mM histidine, 190 mM trehalose, 0.03% polysorbate 20, pH 6.0) | Protein Lot No. Z19003 (Fusion Protein 1, 40 mg/mL, 25 mM histidine, 190 mM trehalose, 0.03% polysorbate 20, pH 6.0) |
|---|---|---|
| Mean (n = 3 or 4)* | 4.495 cP | 5.402 cP |
| Standard deviation | 0.274 | 0.884 |

*Mean value captured from three or four individual test results.

Conclusion

In light of the results of this study, Fusion Protein 1 formulated at 40 mg/mL in 25 mM histidine, 190 mM trehalose and 0.03% PS20 pH 6.0 was compatible with the selected container closure system and remained stable for at least 12 months when stored at −20° C. and 2° C.-8° C.

Example 5. Long-Term Stability Study of Fusion Protein 1

A study was conducted to examine the long-term stability of Fusion Protein 1 formulated at 40 mg/mL in 25 mM histidine, 190 mM trehalose and 0.03% PS20, pH 6.0, at various temperatures. Fusion Protein 1 exhibited stability over two years following storage at −70° C. (Table 26). The variation of $EC_{50}$ was observed in αvβ3 and α5β1 binding at months 9, 18, and 24 (T9, T18, and T24) and months 9, 12, and 24 (T9, T12, and T24). This variation was investigated and indicated that this might be due to expired testing reagents.

TABLE 26

Summary of Stability Data of Fusion Protein 1 at −70° C. ± 10° C.

| Test Items | T0 | T1 | T3 | T6 | T9 | T12 | T18 | T24 |
|---|---|---|---|---|---|---|---|---|
| Appearance | BY6 | BY6 | BY6 | BY6 | BY6 | BY6 | BY5 | BY5 |
| PH | 6.2 | 6.2 | 6.2 | 6.2 | 6.1 | 6.1 | 6.1 | 6.1 |
| A280 (mg/mL) | 41 | 41 | 41 | 41 | 40 | 39 | 41 | 40 |
| SEC-HPLC/UV, main peak (%) | 98.8 | 99.2 | 99.1 | 99.2 | 99.1 | 99.2 | 99.1 | 99.2 |
| SEC-HPLC/UV, aggregate (%) | 1.2 | 0.8 | 0.9 | 0.8 | 0.9 | 0.8 | 0.9 | 0.8 |
| Non-reducing CE-SDS (%) | 100 | 100 | 100 | 100 | 100 | 100 | 100 | 100 |
| Reducing CE-SDS (%) | 99.3 | 99.3 | 99.4 | 99.4 | 99.3 | 99.3 | 99.3 | 99.3 |
| Capillary isoelectric focusing (cIEF) (%) | 99.78 | 99.68 | 99.82 | 99.78 | 99.82 | 99.66 | 99.55 | 99.74 |
| VEGF-$A_{165}$ ELISA binding affinity ($EC_{50}$) | 0.408 | 0.370 | 0.350 | 0.478 | 0.385 | 0.404 | 0.427 | 0.489 |
| αvβ3 ELISA binding affinity ($EC_{50}$) | 0.012 | 0.014 | 0.015 | 0.014 | 0.032 | 0.006 | 0.023 | 0.085 |
| α5β1 ELISA binding affinity ($EC_{50}$) | 0.251 | 0.086 | 0.088 | 0.090 | 0.180 | 0.031 | 0.047 | 0.112 |

T = monthly stability storage of material
BY = brownish-yellow
*α5β1 binding ELISA was further optimized after 0M, T1 data was used for the trend analysis of α5β1 binding ELISA stability.

A study examining the stability of Fusion Protein 1 formulated at 40 mg/mL in 25 mM histidine, 190 mM trehalose and 0.03% PS20, pH 6, following storage at −20° C. over 36 months is ongoing. A summary of the stability results following storage at 9 months at −20° C. is shown in Table 27.

TABLE 27

Stability of Fusion Protein 1 at −20° C. ± 5° C., Upright

| Test Items | T0 | T1 | T3 | T6 | T9 | T12 | T18 | T24 | T36 |
|---|---|---|---|---|---|---|---|---|---|
| Appearance | BY6, essentially free from visible particulates | BY5, essentially free from visible particulates | BY5, essentially free from visible particulates | BY6, essentially free from visible particulates | Between BY5 and BY6, essentially free from visible particulates | TBD | TBD | TBD | TBD |

TABLE 27-continued

Stability of Fusion Protein 1 at −20° C. ± 5° C., Upright

| Test Items | | T0 | T1 | T3 | T6 | T9 | T12 | T18 | T24 | T36 |
|---|---|---|---|---|---|---|---|---|---|---|
| pH | | 6.1 | 6.1 | 6.1 | 6.1 | 6.1 | TBD | TBD | TBD | TBD |
| Osmolality (Osmo/kg) | | 268 | 267 | 267 | 255 | 261.7* | TBD | TBD | TBD | TBD |
| cIEF (%) | | 99.97) | 99.89 | 99.92 | 99.78 | 99.85 | TBD | TBD | TBD | TBD |
| A280 (mg/mL) | | 38 | 39 | 38 | 37 | 37 | TBD | TBD | TBD | TBD |
| SEC-HPLC/UV, main peak (%) | | 99.2 | 99.2 | 97.8 | 99.2 | 99.1 | TBD | TBD | TBD | TBD |
| SEC-HPLC/UV, aggregate (%) | | 0.8 | 0.8 | 2.2 | 0.8 | 0.9 | TBD | TBD | TBD | TBD |
| Non-reducing CE-SDS (%) | | 100 | 100 | 100 | 100 | 100 | TBD | TBD | TBD | TBD |
| Reducing CE-SDS (%) | | 99.3 | 99.3 | 99.4 | 99.4 | 99.2 | TBD | TBD | TBD | TBD |
| VEGF-A$_{165}$ binding relative potency (%) | | 109 | 99 | 104 | 96 | 106 | TBD | TBD | TBD | TBD |
| αvβ3 binding relative potency (%) | | 129 | 114 | 125 | 88 | 101 | TBD | TBD | TBD | TBD |
| α5β1 binding relative potency (%) | | 129 | 100 | 112 | 113 | 104 | TBD | TBD | TBD | TBD |
| Sub-visible particulate matter | 10 μm | 1 | NT | NT | 17 | NT | TBD | NT | TBD | TBD |
| | 25 μm | 0 | NT | NT | 0 | NT | TBD | NT | TBD | TBD |
| | 50 μm | 0 | NT | NT | 0 | NT | TBD | NT | TBD | TBD |

T = monthly stability storage of material;
BY = brownish-yellow;
NT = not tested;
TBD = to be determined;
TO = Test omitted;
*data collected from osmolality investigation Additionally, a study examining the stability of Fusion Protein 1 formulated at 40 mg/mL in 25 mM histidine, 190 mM trehalose and 0.03% PS20, pH 6, following storage at 5° C. over 36 months is ongoing. A summary of the stability results following storage at 9 months at 5° C. either upright or inverted is shown in Table 28 and Table 29, respectively.

TABLE 28

Stability of Fusion Protein 1 at 5° C. ± 3° C., Upright

| Test Items | T0 | T1 | T3 | T6 | T9 | T12 | T18 | T24 | T36 |
|---|---|---|---|---|---|---|---|---|---|
| Appearance | BY6, essentially free from visible particulates | BY5, essentially free from visible particulates | BY5, essentially free from visible particulates | BY6, essentially free from visible particulates | Between BY5 and BY6, essentially free from visible particulates | TBD | TBD | TBD | TBD |
| pH | 6.1 | 6.1 | 6.1 | 6.1 | 6.1 | TBD | TBD | TBD | TBD |
| Osmolality (mOsmo/kg) | 268 | 267 | 267 | 267 | 266 | TBD | TBD | TBD | TBD |
| cIEF (%) | 99.97 | 99.93 | 99.78 | 99.89 | 99.92 | TBD | TBD | TBD | TBD |
| A280 (mg/mL) | 38 | 38 | 38 | 38 | 38 | TBD | TBD | TBD | TBD |
| SEC-HPLC/UV, main peak (%) | 99.2 | 99.0 | 99.3 | 98.7 | 98.5 | TBD | TBD | TBD | TBD |
| SEC-HPLC/UV, aggregate (%) | 0.8 | 1.0 | 0.7 | 1.3 | 1.5 | TBD | TBD | TBD | TBD |
| Non-reducing CE-SDS, (%) | 100 | 100 | 100 | 100 | 100 | TBD | TBD | TBD | TBD |
| Reducing CE-SDS, (%) | 99.3 | 99.3 | 99.3 | 99.3 | 99.1 | TBD | TBD | TBD | TBD |
| VEGF-A$_{165}$ binding relative potency (%) | 109 | 108 | 102 | 102 | 102 | TBD | TBD | TBD | TBD |
| αvβ3 binding relative potency (%) | 129 | 89 | 100 | 104 | 95 | TBD | TBD | TBD | TBD |

TABLE 28-continued

Stability of Fusion Protein 1 at 5° C. ± 3° C., Upright

| Test Items | T0 | T1 | T3 | T6 | T9 | T12 | T18 | T24 | T36 |
|---|---|---|---|---|---|---|---|---|---|
| α5β1 binding relative potency (%) | 129 | 103 | 103 | 105 | 102 | TBD | TBD | TBD | TBD |

T = monthly stability storage of material;
BY = brownish-yellow;
TBD = to be determined

TABLE 29

Stability of Fusion Protein 1 at 5° C. ± 3° C., Inverted

| Test Items | T0 | T1 | T3 | T6 | T9 | T12 | T18 | T24 | T36 |
|---|---|---|---|---|---|---|---|---|---|
| Appearance | BY6, essentially free from visible particulates | BY5, essentially free from visible particulates | BY5, essentially free from visible particulates | BY6, essentially free from visible particulates | Between BY5 and BY6, essentially free from visible particulates | TBD | TBD | TBD | TBD |
| pH | 6.1 | 6.1 | 6.1 | 6.1 | 6.1 | TBD | TBD | TBD | TBD |
| Osmolality (mOsmo/kg) | 268 | 268 | 267 | 267 | 267 | TBD | TBD | TBD | TBD |
| cIEF (%) | 99.97 | 99.89 | 99.80 | 99.85 | 99.98 | TBD | TBD | TBD | TBD |
| A280 (mg/mL) | 38 | 38 | 38 | 38 | 38 | TBD | TBD | TBD | TBD |
| SEC-HPLC/UV, main peak (%) | 99.2 | 99.0 | 98.8 | 98.6 | 98.5 | TBD | TBD | TBD | TBD |
| SEC-HPLC/UV, aggregate (%) | 0.8 | 1.0 | 1.2 | 1.4 | 1.5 | TBD | TBD | TBD | TBD |
| Non-reducing CE-SDS (%) | 100 | 100 | 100 | 100 | 100 | TBD | TBD | TBD | TBD |
| Reducing CE-SDS (%) | 99.3 | 99.4 | 99.3 | 99.3 | 99.2 | TBD | TBD | TBD | TBD |
| VEGF-A$_{165}$ binding relative potency (%) | 109 | 103 | 103 | 92 | 92 | TBD | TBD | TBD | TBD |
| αvβ3 binding relative potency (%) | 129 | 122 | 100 | 90 | 107 | TBD | TBD | TBD | TBD |
| α5β1 binding relative potency (%) | 129 | 101 | 127 | 94 | 99 | TBD | TBD | TBD | TBD |
| Sub-visible particulate matter 10 µm | 1 | NT | NT | 23 | NT | TBD | NT | TBD | TBD |
| Sub-visible particulate matter 25 µm | 0 | NT | NT | 4 | NT | TBD | NT | TBD | TBD |
| Sub-visible particulate matter 50 µm | 0 | NT | NT | 0 | NT | TBD | NT | TBD | TBD |

T = monthly stability storage of material;
BY = brownish-yellow;
NT = not tested;
TBD = to be determined.

Furthermore, a study was performed that examined the stability of Fusion Protein 1 formulated at 40 mg/mL in 25 mM histidine, 190 mM trehalose and 0.03% PS20, pH 6, following storage at 25° C. over 6 months. A summary of the stability results following storage at 6 months at 25° C. is shown in Table 30.

TABLE 30

Stability of Fusion Protein 1 at 25° C. ± 2° C./60% ± 5% RH, Upright

| Test Items | T0 | T1 | T3 | T6 |
|---|---|---|---|---|
| Appearance | BY6, essentially free from visible particulates | BY5, essentially free from visible particulates | BY5, essentially free from visible particulates | BY5, essentially free from visible particulates |
| PH | 6.1 | 6.1 | 6.1 | 6.1 |
| Osmolality (mOsm/kg) | 268 | 268 | 269 | 271 |
| cIEF (%) | 99.97 | 99.91 | 99.85 | 99.83 |
| A280 (mg/mL) | 38 | 38 | 38 | 38 |
| SEC-HPLC/UV, main peak (%) | 99.2 | 98.3 | 98.8 | 96.9 |
| SEC-HPLC/UV aggregate (%) | 0.8 | 1.7 | 1.2 | 3.1 |
| Non-reducing CE-SDS (%) | 100 | 100 | 100 | 100 |
| Reducing CE-SDS (%) | 99.3 | 99.4 | 98.9 | 98.5 |

TABLE 30-continued

Stability of Fusion Protein 1 at 25° C. ± 2° C./60% ± 5% RH, Upright

| Test Items | | T0 | T1 | T3 | T6 |
|---|---|---|---|---|---|
| VEGF-A$_{165}$ binding relative potency (%) | | 109 | 103 | 98 | 89 |
| αvβ3 binding relative potency (%) | | 129 | 116 | 125 | 111 |
| α5β1 binding ELISA (%) | | 129 | 108 | 126 | 89 |
| Sub-visible particulate matter | 10 µm | 1 | NT | NT | 18 |
| | 25 µm | 0 | NT | NT | 2 |
| | 50 µm | 0 | NT | NT | 2 |

T = monthly stability storage of material;
BY, brownish-yellow;
NT = not tested.

Example 6. Vascular Leakage Score in Rabbits Treated with the Formulation of Fusion Protein 1 Following Stimulation with VEGF-A$_{165}$ An in vivo study was conducted to test the efficacy of various doses of Fusion Protein 1 formulated in the above-described formulation of interest 9 (40 mg/mL of Fusion Protein 1 in 25 mM histidine, 190 mM trehalose and 0.03% PS20, pH 6). Human VEGF-induced retinal vascular leakage was examined in Dutch Belted rabbits by defined leakage score based on standardized fluorescence angiography (FA) scoring images. Leakage score was categorized from 0 to 4 (0, major vessel very straight, with some tortuosity of small vessels; 1, increased tortuosity of major vessels and/or vessel dilation; 2, leakage between major vessels; 3, leakage between major and minor vessels, minor vessel still visible; 4, leakage between major and minor vessels, minor vessel not visible).

Each rabbit received bilateral single intravitreal injection with 50 each group had a total of 3 rabbits and 6 eyes. On Day 0 Rabbits were administered 50 µL of vehicle control, Avastin® (1.25 mg/eye), Eylea® (0.625 mg/eye), and increasing concentrations of Fusion Protein 1 (i.e., 0.03 mg, 0.1 mg, 0.3 mg, and 1 mg per eye). The rabbits were then stimulated with 1000 ng of human VEGF-A$_{165}$ on Day 2 and FA was used to assess leakage score on Day 5.

Figure 10:
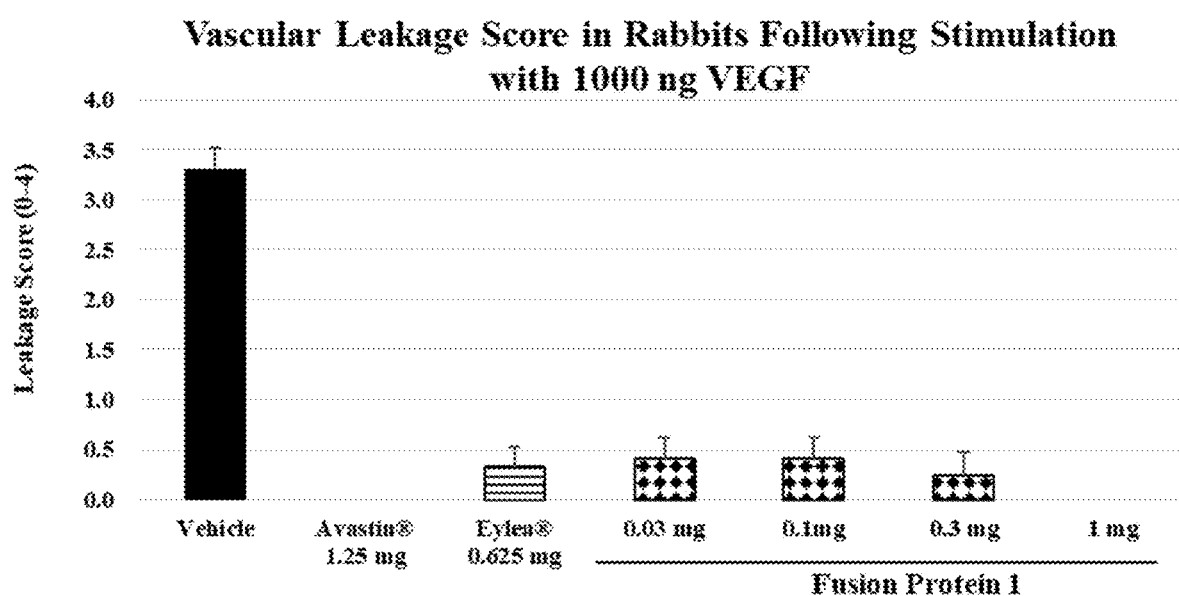
FIG. 10 is a graph of a single dose administration of Fusion Protein 1 at the indicated concentrations in Dutch Belted rabbits, which inhibits human VEGF-$A_{165}$ induced retinal vascular permeability.

Rabbits treated with as low as 0.03 mg of Fusion Protein 1 exhibited a decreased vascular leakage score (FIG. 10). Consequently, a dose as low as 0.03 mg of Fusion Protein 1 effectively reduces vascular leakage.

Fusion Protein 1 doses were comparable with Avastin® and Eylea® in its ability to inhibit VEGF-induced retinal leakage. These data support Fusion Protein 1 to be suitable in treating angiogenic retinal diseases such as DME, nAMD, and RVO.

We claim:

1. A pharmaceutical formulation, the formulation comprising:
   a) a fusion protein in a concentration of 40 mg/mL, wherein the fusion protein comprises the amino acid sequence of SEQ ID NO:15, SEQ ID NO:16, SEQ ID NO: 17, or SEQ ID NO: 18,
   b) 25 mM histidine,
   c) 190 mM trehalose or mannitol, and
   d) 0.03% polysorbate 20 or polysorbate 80,
wherein the formulation is at a pH of about 6.0.

2. The pharmaceutical formulation of claim 1, wherein the formulation is stable at −70° C., −20° C. and/or 5° C. for at least 24 months.

3. The pharmaceutical formulation of claim 1, wherein the formulation retains protein purity and potency after at least 6 months at −70° C., −20° C., and/or 2-8° C.

4. The pharmaceutical formulation of claim 1, wherein the formulation further comprises a salt in a concentration of about 10 mM to 50 mM.

5. The pharmaceutical formulation of claim 4, wherein the salt is selected from sodium chloride, magnesium chloride, calcium chloride, or potassium chloride.

6. The pharmaceutical formulation of claim 1, wherein the formulation further comprises at least one amino acid in a concentration of about 10 mM to 50 mM.

7. The pharmaceutical formulation of claim 6, wherein the amino acid is selected from the group consisting of arginine, methionine, proline, histidine, cysteine, lysine, glycine, aspartate, tryptophan, glutamate, and isoleucine.

* * * * *